(12) United States Patent
Masuda et al.

(10) Patent No.: US 10,646,123 B2
(45) Date of Patent: May 12, 2020

(54) BLOOD CIRCUIT HAVING PRESSURE MEASUREMENT PORTION

(71) Applicant: NIPRO CORPORATION, Osaka-shi, Osaka (JP)

(72) Inventors: Toshiaki Masuda, Osaka (JP); Takeshi Yamaguchi, Osaka (JP)

(73) Assignee: NIPRO CORPORATION, Osaka-Shi (JP)

( * ) Notice: Subject to any disclaimer, the term of this patent is extended or adjusted under 35 U.S.C. 154(b) by 384 days.

(21) Appl. No.: 15/522,642

(22) PCT Filed: Oct. 28, 2015

(86) PCT No.: PCT/JP2015/080456
§ 371 (c)(1),
(2) Date: Apr. 27, 2017

(87) PCT Pub. No.: WO2016/068213
PCT Pub. Date: May 6, 2016

(65) Prior Publication Data
US 2017/0319086 A1    Nov. 9, 2017

(30) Foreign Application Priority Data

Oct. 28, 2014    (JP) .................................. 2014-219469

(51) Int. Cl.
*A61B 5/022*    (2006.01)
*A61B 5/021*    (2006.01)
(Continued)

(52) U.S. Cl.
CPC .......... *A61B 5/02241* (2013.01); *A61B 5/026* (2013.01); *A61B 5/02141* (2013.01);
(Continued)

(58) Field of Classification Search
CPC .................................................. A61B 5/02141
See application file for complete search history.

(56) References Cited

U.S. PATENT DOCUMENTS 5,186,431 A     2/1993  Tamari
5,336,051 A *   8/1994  Tamari ................ A61M 1/3621
                                                    417/19
(Continued)

FOREIGN PATENT DOCUMENTS

JP          58-153841 U     10/1983
JP          61-143069 A      6/1986
(Continued)

OTHER PUBLICATIONS

Extended European Search Report, dated May 15, 2018, for European Application No. 15854357.9.
(Continued)

*Primary Examiner* — Scott Luan
(74) *Attorney, Agent, or Firm* — Birch, Stewart, Kolasch & Birch, LLP

(57) ABSTRACT

A blood circuit having a pressure measurement portion connected to a pressure measurement device includes: a first measurement portion provided downstream of a pumping segment; and a second measurement portion provided upstream of the pumping segment. The first measurement portion includes: a first housing having a tubular shape; and a first flexible membrane having a tubular shape and provided in the first housing. The second measurement portion includes: a second housing having a tubular shape; and a second flexible membrane having a tubular shape and provided in the second housing. A space between the first flexible membrane and the first housing is larger than a space (Continued)

between the second flexible membrane and the second housing in an initial state before permitting the blood to flow.

10 Claims, 44 Drawing Sheets

(51) Int. Cl.
    *A61B 5/026*       (2006.01)
    *A61M 1/36*        (2006.01)
    *A61B 5/02*        (2006.01)

(52) U.S. Cl.
    CPC ....... *A61M 1/3639* (2013.01); *A61B 5/02007* (2013.01); *A61M 2205/3331* (2013.01)

(56) References Cited

U.S. PATENT DOCUMENTS

| | | | |
|---|---|---|---|
| 5,813,842 A * | 9/1998 | Tamari | A61M 1/3621 417/477.1 |
| 6,526,357 B1 | 2/2003 | Soussan et al. | |
| 8,092,414 B2 | 1/2012 | Schnell et al. | |

FOREIGN PATENT DOCUMENTS

| | | |
|---|---|---|
| JP | 61-106252 U | 7/1986 |
| JP | H01-147330 A | 6/1989 |
| JP | S63-001538 U | 6/1989 |
| JP | 5-23393 A | 2/1993 |
| JP | 8-500252 A | 1/1996 |
| JP | 8-510812 A | 11/1996 |
| JP | 9-24026 A | 1/1997 |
| JP | 2010-121964 A | 6/2010 |
| JP | 2010-125131 A | 6/2010 |
| WO | WO 93/18324 A1 | 9/1993 |
| WO | WO 94/28309 A1 | 12/1994 |
| WO | WO 2009/061608 A1 | 5/2009 |

OTHER PUBLICATIONS

Japanese Office Action, dated Mar. 17, 2020, for Japanese Application No. 2016-556609.

* cited by examiner (A)

(B)

(C)

1120

1120

126
127
1120

FIG.83
(A) 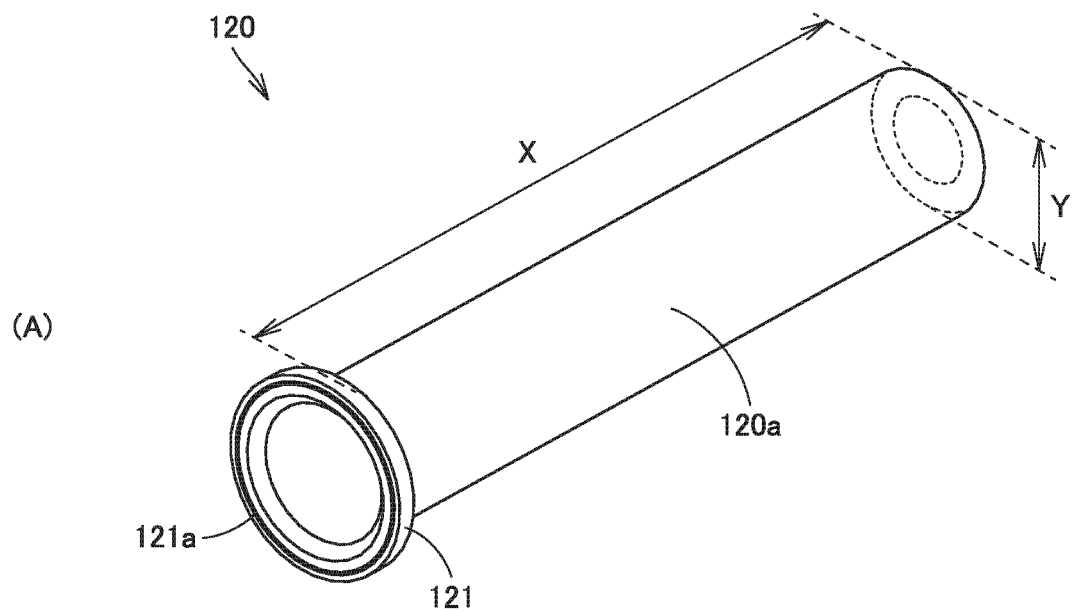
(B) 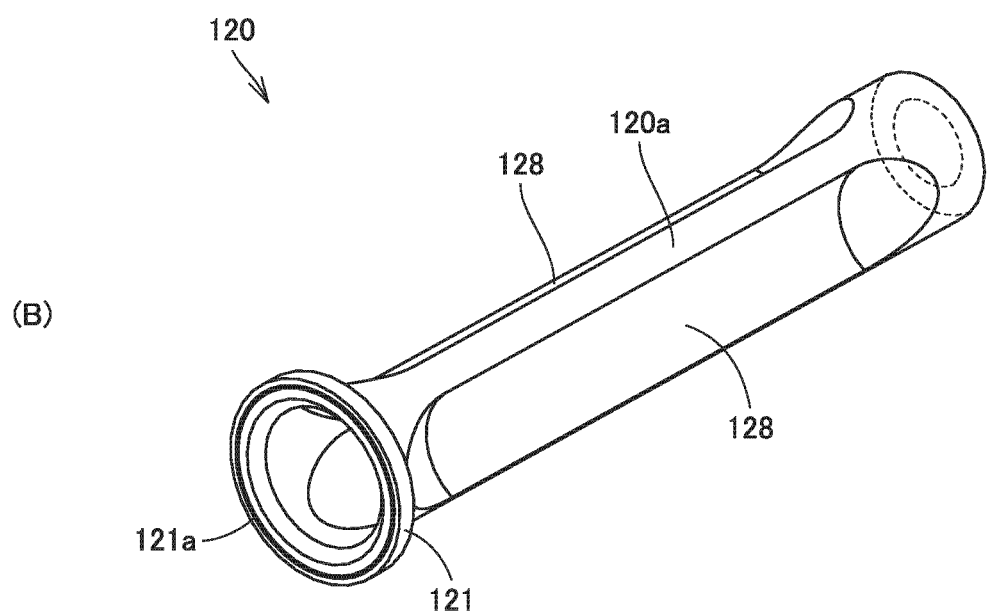

FIG.85

| RATIO X/Y | 3.0 | 4.0 | 5.0 | 6.0 | 7.0 | 8.0 | 9.0 | 10.0 |
|---|---|---|---|---|---|---|---|---|
| DEFORMABILITY | LOW | HIGH | HIGH | HIGH | HIGH | HIGH | HIGH | HIGH |
| DEFORMED SHAPE | SUBSTANTIALLY TRIANGULAR SHAPE | SUBSTANTIALLY TRIANGULAR SHAPE | SUBSTANTIALLY TRIANGULAR SHAPE | SUBSTANTIALLY TRIANGULAR SHAPE | SUBSTANTIALLY TRIANGULAR SHAPE | SUBSTANTIALLY TRIANGULAR SHAPE | STRAIGHT LINE SHAPE | STRAIGHT LINE SHAPE |
| COMPREHENSIVE EVALUATION | NON-APPLICABLE | APPLICABLE | APPLICABLE | APPLICABLE | APPLICABLE | APPLICABLE | NON-APPLICABLE | NON-APPLICABLE |

FIG.93
(A)
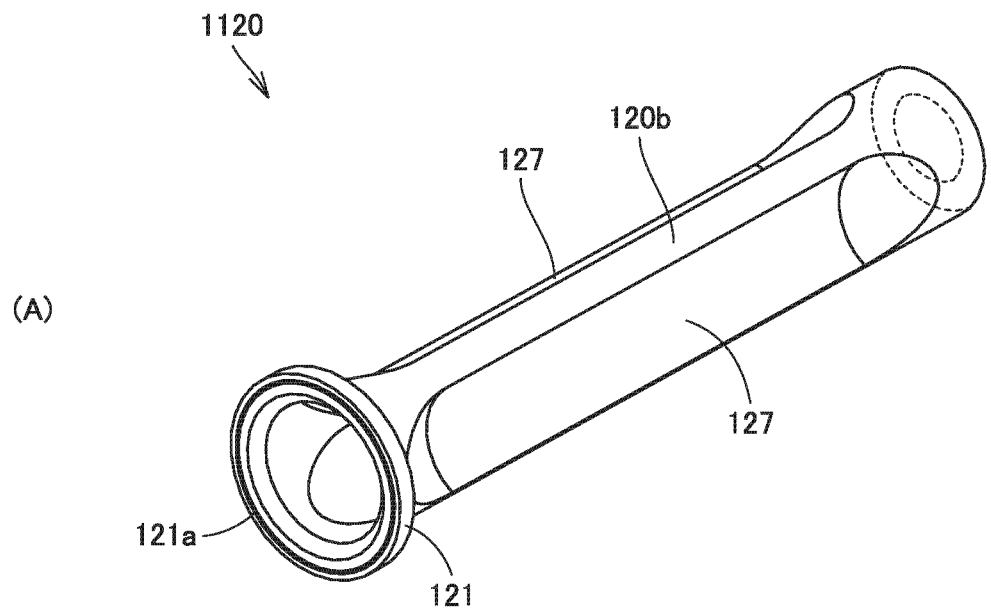
(B)
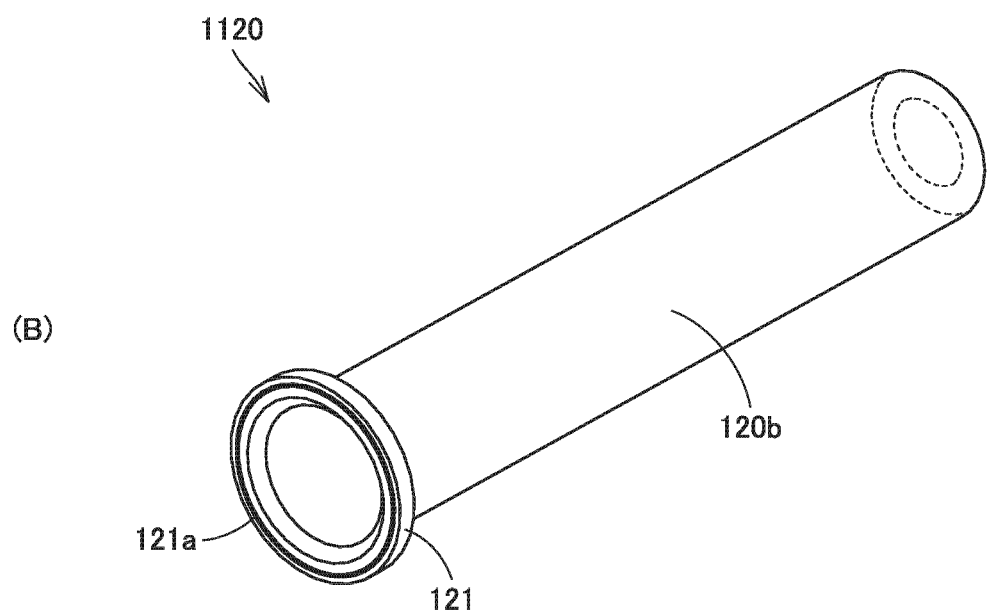

BLOOD CIRCUIT HAVING PRESSURE MEASUREMENT PORTION

TECHNICAL FIELD

The present invention relates to a blood circuit having a pressure measurement portion, more particularly, a blood circuit having a pressure measurement portion using a flexible membrane.

BACKGROUND ART

Conventionally, blood circuits are disclosed in, for example, Japanese Utility Model Laying-Open No. 58-153841 (Patent Document 1), Japanese Patent Laying-Open No. 61-143069 (Patent Document 2), U.S. Pat. No. 6,526,357 (Patent Document 3), Japanese Patent Laying-Open No. 5-23393 (Patent Document 4), Japanese Patent Laying-Open No. 9-24026 (Patent Document 5) and U.S. Pat. No. 8,092,414 (Patent Document 6).

CITATION LIST

Patent Document

PTD 1: Japanese Utility Model Laying-Open No. 58-153841
PTD 2: Japanese Patent Laying-Open No. 61-143069
PTD 3: U.S. Pat. No. 6,526,357
PTD 4: Japanese Patent Laying-Open No. 5-23393
PTD 5: Japanese Patent Laying-Open No. 9-24026
PTD 6: U.S. Pat. No. 8,092,414

SUMMARY OF INVENTION

Technical Problem

The blood circuit described in Patent Document 1 is provided with a pressure detection chamber. The pressure detection chamber has a flexible membrane, and the flexible membrane divides the inside of the chamber into two spaces. A fluid tube path communicates with one space, which is isolated from the other space. The other space is connected to a pressure measurement device.

If positive pressure and negative pressure are measured using one membrane as in Patent Document 1, a variable volume of the membrane becomes large inevitably, thus resulting in a large size of the pressure measurement portion, disadvantageously.

In view of this, the present invention has been made to solve the above-described problem, and has an object to provide a blood circuit capable of measuring blood pressure with high precision.

Solution to Problem

A blood circuit according to one aspect of the present invention is a blood circuit having a pressure measurement portion connected to a pressure measurement device, the blood circuit including: a first measurement portion provided downstream of a pumping segment for applying pressure to blood; and a second measurement portion provided upstream of the pumping segment, the first measurement portion including: a first housing having a tubular shape; and a first flexible membrane having a tubular shape and provided in the first housing having the tubular shape, pressure fluctuation of the blood being able to be measured by permitting the blood to flow in a tube of the first flexible membrane to displace the first flexible membrane according to pressure of the blood, the second measurement portion including: a second housing having a tubular shape; and a second flexible membrane having a tubular shape and provided in the second housing having the tubular shape, the pressure fluctuation of the blood being able to be measured by permitting the blood to flow in a tube of the second flexible membrane to displace the second flexible membrane according to the pressure of the blood, a space between the first flexible membrane and the first housing being larger than a space between the second flexible membrane and the second housing in an initial state before permitting the blood to flow.

By using each flexible membrane having the tubular shape in this way, the deformable portion of the flexible membrane can be made long in the axial direction, whereby retention of blood is unlikely to occur. Moreover, by configuring such that the space volume of the pressure measurement portion for measurement of positive pressure is different from the space volume of the pressure measurement portion for measurement of negative pressure, each of the pressure measurement portions can be reduced in size.

The size reduction of the pressure measurement portion is expected to lead to improvement in handling as well as cost effects such as reduction of transportation cost and resin.

Moreover, the size reduction of the flexible membrane having the tubular shape leads to a small contact area between the flexible membrane and the blood, thereby decreasing pressure loss resulting from friction. Pressure fluctuation can be measured more precisely as compared with conventional structures. It should be noted that when pressure loss is large, pressure on a line becomes different from pressure on the measurement portion. This may result in a large difference between the worst pressure value, i.e., pressure value on the line in the vicinity of the pump and a pressure value measured by the pressure measurement portion, or may result in a decreased rate of flow returning to the patient.

Further, since the cross sectional area of the flexible membrane having the tubular shape is smaller than those in the conventional structures, retention of blood can be decreased.

Preferably, the first flexible membrane is provided to have the tubular shape with the space being formed between the first flexible membrane and the first housing, and has a cross section at least a portion of which has a non-circular portion, the pressure fluctuation of the blood is able to be measured by permitting the blood to flow in the tube of the first flexible membrane to deform the non-circular portion of the first flexible membrane in a tube outward direction according to the pressure of the blood to decrease the space between the first flexible membrane and the first housing, and the second flexible membrane is provided close to the second housing.

In the blood circuit having the pressure measurement portion thus configured, positive pressure is measured by the first measurement portion having the first flexible membrane having the non-circular cross section, and negative pressure is measured by the second measurement portion having the second flexible membrane close to the second housing. By forming the respective flexible membranes to have shapes suitable for positive pressure measurement and negative pressure measurement, pressure fluctuation can be measured more precisely than that in a case where positive pressure and negative pressure are measured using one flexible membrane. A flexible membrane having a tubular shape and having a circular cross section can be expanded only through elastic deformation. Hence, elastic force absorbs part of pressure in the fluid chamber, thus resulting in a pressure error. Such a pressure error can be suppressed using a flexible membrane at least partially including a non-circular cross section. Further, since the flexible membrane having the tubular shape is close to the housing in the pressure measurement portion for measuring negative pressure, the size of the pressure measurement portion can be made as small as possible. The term "pressure error" refers to output of pressure different from actual pressure due to pressure absorption by elastic force. The term "pressure loss" refers to a difference caused between a pressure on a line and pressure on a pressure measurement portion due to interference between fluid and a certain object in the flow path.

A blood circuit according to another aspect of the present invention is a blood circuit having a pressure measurement portion connected to a pressure measurement device, the blood circuit including: a housing having a tubular shape; and a flexible membrane having a tubular shape and provided within the housing having the tubular shape, the flexible membrane being provided close to the housing, pressure fluctuation of blood being able to be measured by permitting the blood to flow in a tube of the flexible membrane to deform the flexible membrane in a tube inward direction according to pressure of the blood to increase a space between the flexible membrane and the housing.

In the blood circuit having the pressure measurement portion thus configured, since the flexible membrane is close to the housing, the housing can be compact. The term "close" indicates a state of intimate contact or separation with a slight distance. Further, in the negative pressure measurement, negative pressure can be measured precisely.

Preferably, the flexible membrane has a cylindrical shape to have an inner diameter and an outer diameter each constant in an axial direction in an initial state before permitting the blood to flow.

In the blood circuit having the pressure measurement portion thus configured, flow resistance to blood becomes small, thereby preventing retention of blood.

Preferably, in the initial state before permitting the blood to flow, the flexible membrane has a cross section with a substantially exactly circular shape, and the housing has a cylindrical shape to have a cross section with a substantially exact circluar shape to have an inner diameter and an outer diameter each constant in the axial direction.

In the blood circuit having the pressure measurement portion thus configured, the pressure measurement portion is reduced in size as much as possible while preventing retention of blood.

Preferably, when X represents an axial length of a deformable portion of the flexible membrane in the initial state before permitting the blood to flow and Y represents an outer diameter of the deformable portion of the flexible membrane in the initial state before permitting the blood to flow, the axial length X and the outer diameter Y satisfy $4.0 \leq X/Y \leq 8.0$, when T represents a thickness of the deformable portion of the flexible membrane in the initial state before permitting the blood to flow, the thickness T satisfies $0.2 \text{ mm} \leq T \leq 0.6 \text{ mm}$, and the flexible membrane has a Shore A hardness of not less than 20 and not more than 60.

In the blood circuit having the pressure measurement portion thus configured, the flexible membrane having the cylindrical shape is displaced in the tube inward direction when the blood flows in the flexible membrane, whereby the cross section thereof is deformed into a substantially triangular shape in which respective sides are recessed. Accordingly, a large variable volume can be secured. Moreover, since the flexible membrane is deformed to have the cross section with the triangular shape, a space surely remains at the central portion in the cross section, thereby preventing the flexible membrane from being closed. Accordingly, flow of blood can be secured.

Preferably, the blood circuit further includes: a first joint component attached to one end of the housing in the axial direction; and a second joint component attached to the other end of the housing in the axial direction, wherein an end portion of the flexible membrane having the tubular shape is fixed by sandwiching the end portion of the flexible membrane between the housing and at least one of the first joint component and the second joint component in the axial direction.

In the blood circuit having the pressure measurement portion thus configured, since at least one end portion of the flexible membrane is compressed in the axial direction, sealing property can be secured at that portion. Moreover, as compared with a case where the end portion of the flexible membrane is compressed in the radial direction for the purpose of fixation, forceful engagement does not need to be made at least at the end portion, thereby reducing risk of positional deviation of an attachment position of the flexible membrane relative to the housing, the first joint component, and the second joint component.

Preferably, one end portion of the flexible membrane having the tubular shape is fixed by sandwiching the one end portion of the flexible membrane between the first joint component and the housing in the axial direction, and the other end portion of the flexible membrane having the tubular shape is fixed by sandwiching the other end portion of the flexible membrane between the second joint component and the housing in a radial direction.

During manufacturing of the blood circuit having the pressure measurement portion thus configured, the blood circuit can be assembled using the following simple method: the first joint component is attached to one end portion of the flexible membrane, they are pressed into the housing, and then the second joint component is attached to the housing. Accordingly, manufacturing cost can be reduced.

A blood circuit having a pressure measurement portion according to still another aspect of the present invention is a blood circuit having a pressure measurement portion connected to a pressure measurement device, the blood circuit including: a housing having a tubular shape; and a flexible membrane having a tubular shape and provided in the housing having the tubular shape with a space being formed between the housing and the flexible membrane, the flexible membrane having a cross section at least a portion of which is non-circular, pressure fluctuation of blood being able to be measured by permitting the blood to flow in a tube of the flexible membrane to deform a non-circular portion of the flexible membrane in a tube outward direction according to pressure of the blood to decrease the space between the housing and the flexible membrane.

In the blood circuit thus configured, since the flexible membrane has the cross section with the non-circular shape, the non-circular portion is deformed in the tube outward direction into a substantially circular shape. In this case, by employing this configuration, the flexible membrane can be facilitated to be deformed in the tubular outward direction because strength is decreased as compared with a flexible membrane having a cylindrical shape having a cross section with an exactly circular shape. As a result, the flexible membrane can be readily deformed in the tube outward direction, whereby a slight change in pressure can be measured precisely.

Preferably, a plurality of recesses are formed in a surface of the flexible membrane and extend in parallel with one another.

In the blood circuit having the pressure measurement portion thus configured, flow resistance to blood becomes small, thereby preventing retention of blood.

Preferably, in an initial state before permitting the blood to flow, in an appropriate cross section orthogonal to an axial direction of the housing and including a deformable portion of the flexible membrane, an outer circumferential edge of the deformable portion of the flexible membrane has a length equal to or less than a length of an inner circumferential edge of the housing.

In the blood circuit having the pressure measurement portion thus configured, when the blood flows in the flexible membrane, the deformable portion of the flexible membrane is deformed in the tube outward direction into a substantially cylindrical shape. Accordingly, a large variable volume can be secured. Moreover, the deformation of the flexible membrane can be prevented from being blocked by the flexible membrane itself and the housing. Hence, the flexible membrane is smoothly deformed into the substantially cylindrical shape, with the result that retention of blood can be prevented.

Preferably, the number of the recesses extending in parallel with one another is 2 to 4.

In the blood circuit having the pressure measurement portion thus configured, a particularly large variable volume is secured.

Preferably, the flexible membrane is configured to have an inner circumferential surface not contacted at any portion in the initial state before permitting the blood to flow.

The blood circuit having the pressure measurement portion thus configured does not have a narrow blood flow path otherwise caused due to a contact between portions of the inner circumferential surface of the flexible membrane even in the initial state. Accordingly, retention of blood can be prevented.

Preferably, in the initial state before permitting the blood to flow, each of cross sectional areas in the tube of the flexible membrane at both end portions of a deformable portion of the flexible membrane is larger than a cross sectional area in the tube of the flexible membrane at a central portion of the deformable portion of the flexible membrane.

Preferably, in the initial state before permitting the blood to flow, a cross sectional area in the tube of the flexible membrane becomes gradually smaller in a direction from each of the both end portions of the deformable portion of the flexible membrane to the central portion of the deformable portion of the flexible membrane.

In the blood circuit having the pressure measurement portion thus configured, particularly between the pair of end portions of the flexible membrane, there is no portion having a flow path larger than that in the pair of end portions. Hence, retention of blood can be prevented more securely.

Preferably, the blood circuit further includes: a first joint component attached to one end of the housing in an axial direction; and a second joint component attached to the other end of the housing in the axial direction, wherein an end portion of the flexible membrane having the tubular shape is fixed by sandwiching the end portion of the flexible membrane between the housing and at least one of the first joint component and the second joint component in the axial direction.

In the blood circuit having the pressure measurement portion thus configured, since at least one end portion of the flexible membrane is compressed in the axial direction, a sealing property can be secured at that portion. Moreover, as compared with a case where the end portion of the flexible membrane is compressed in the radial direction for the purpose of fixation, forceful engagement does not need to be made at least at the end portion, thereby reducing risk of positional deviation of an attachment position of the flexible membrane relative to the housing, the first joint component, and the second joint component.

Preferably, one end portion of the flexible membrane having the tubular shape is fixed by sandwiching the one end portion of the flexible membrane between the first joint component and the housing in the axial direction, and the other end portion of the flexible membrane having the tubular shape is fixed by sandwiching the other end portion of the flexible membrane between the second joint component and the housing in a radial direction.

During manufacturing of the blood circuit having the pressure measurement portion thus configured, the blood circuit can be assembled using the following simple method: the first joint component is attached to one end portion of the flexible membrane, they are pressed into the housing, and then the second joint component is attached to the housing. Accordingly, manufacturing cost can be reduced.

A blood circuit having a pressure measurement portion according to yet another aspect of the present invention is a blood circuit having a pressure measurement portion connected to a pressure measurement device, the blood circuit including: a housing having a tubular shape and having one end and the other end in an axial direction; a flexible membrane having a tubular shape and provided in the housing having the tubular shape; a first joint component attached to the one end of the housing; and a second joint component attached to the other end of the housing, pressure fluctuation of blood being able to be measured by permitting the blood to flow in a tube of the flexible membrane to displace the flexible membrane according to pressure of the blood, an end portion of the flexible membrane having the tubular shape being fixed by sandwiching the end portion of the flexible membrane between the housing and at least one of the first joint component and the second joint component in the axial direction.

In the blood circuit having the pressure measurement portion thus configured, since at least one end portion of the flexible membrane is compressed in the axial direction, a sealing property can be secured at that portion. Moreover, as compared with a case where the end portion of the flexible membrane is compressed in the radial direction for the purpose of fixation, forceful engagement does not need to be made at least at the end portion, thereby reducing risk of positional deviation of an attachment position of the flexible membrane relative to the housing, the first joint component, and the second joint component.

Preferably, one end portion of the flexible membrane having the tubular shape is fixed by sandwiching the one end portion of the flexible membrane between the first joint component and the housing in the axial direction, and the other end portion of the flexible membrane having the tubular shape is fixed by sandwiching the other end portion of the flexible membrane between the second joint component and the housing in a radial direction.

During manufacturing of the blood circuit having the pressure measurement portion thus configured, the blood circuit can be assembled using the following simple method: the first joint component is attached to one end portion of the flexible membrane, they are pressed into the housing, and then the second joint component is attached to the housing. Accordingly, manufacturing cost can be reduced.

Advantageous Effects of Invention

According to the present invention, there can be provided a blood circuit capable of measuring blood pressure with high precision.

BRIEF DESCRIPTION OF DRAWINGS

FIG. 83 (A) is a perspective view of the flexible membrane in the state shown in FIG. 82 (A), and FIG. 83 (B) is a perspective view of the flexible membrane in the state shown in FIG. 82 (B).

FIG. 85 is a graph showing a result of a verification test.

FIG. 93 (A) is a perspective view of the flexible membrane in the state shown in FIG. 92 (A), and FIG. 93 (B) is a perspective view of the flexible membrane in the state shown in FIG. 92 (B).

DESCRIPTION OF EMBODIMENTS

First Embodiment

Figure 1:
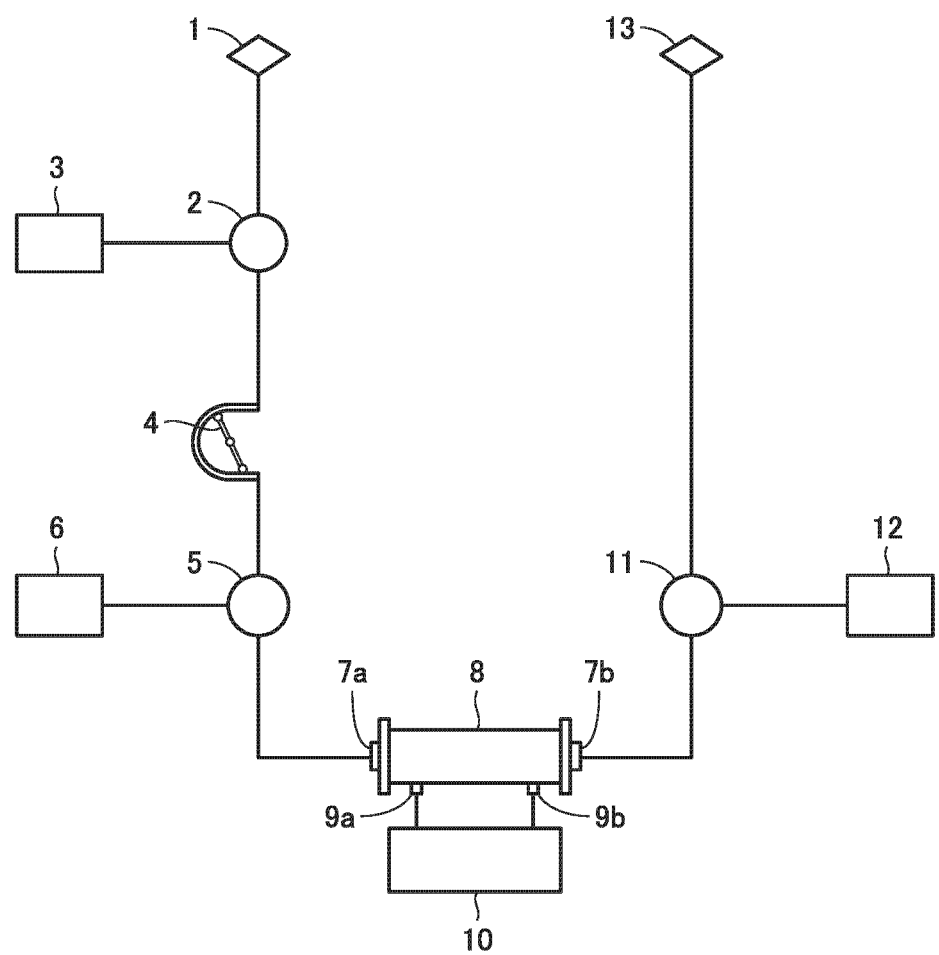
FIG. 1 is a schematic view of a blood circuit provided with a pressure measurement portion according to an embodiment of the present invention.

With reference to FIG. 1, a blood circuit includes: a blood inlet 1 for extracting blood from a patient; an extracted blood pressure measurement site 2 connected to blood inlet 1; a pressure transducer 3 that measures the blood pressure at extracted blood pressure measurement site 2; a blood pump 4 that applies pressure to the blood discharged from extracted blood pressure measurement site 2; a PD pressure measurement site 5 located downstream of blood pump 4; a pressure transducer 6 that measures blood pressure at PD (Pre-dialyzer) pressure measurement site 5; a dialyzer 8 that receives the blood from PD pressure measurement site 5 through a dialyzer blood inlet 7a; a venous pressure measurement site 11 located downstream of a dialyzer blood outlet 7b of dialyzer 8; a pressure transducer 12 that measures blood pressure at venous pressure measurement site 11; and a blood outlet 13 for returning the blood to the patient.

Dialyzer 8 is connected to a dialyzing device body 10 via a dialyzing fluid outlet 9a and a dialyzing fluid inlet 9b, removes wastes in blood using a dialyzing fluid, and adjusts water content in the blood.

Figure 2:
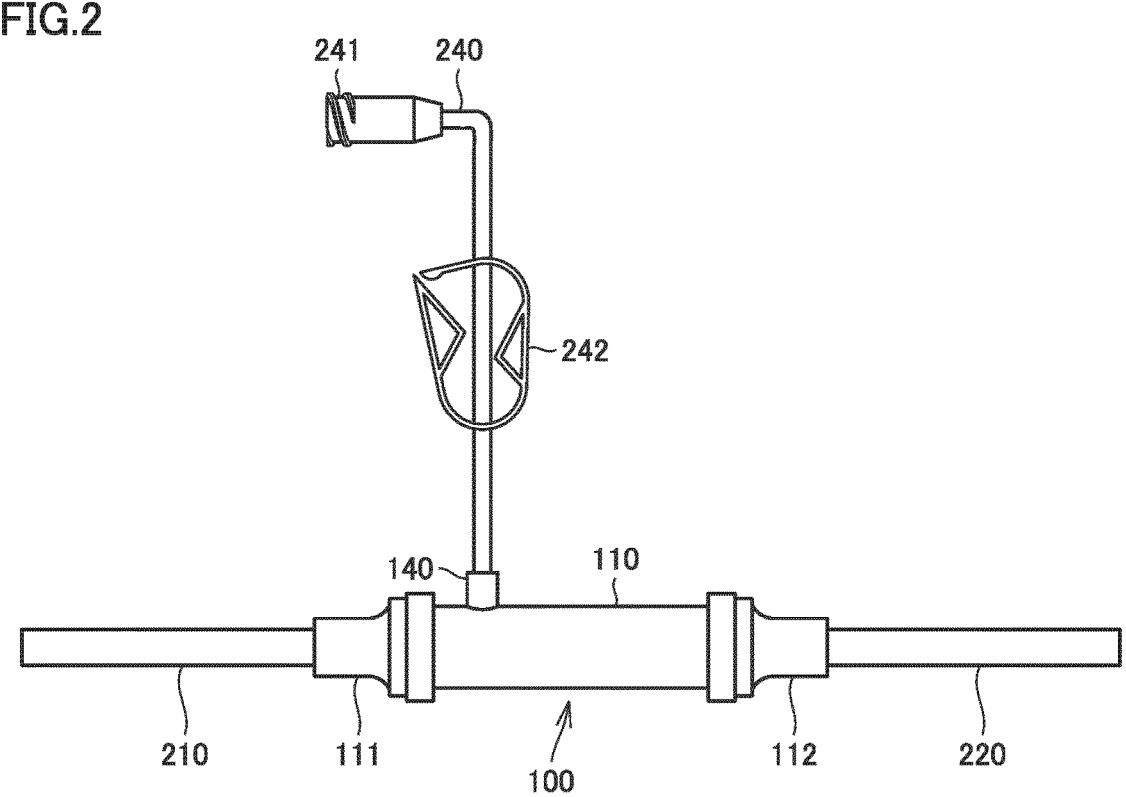
FIG. 2 is a front view of a pressure measurement portion for measuring negative pressure according to a first embodiment.

With reference to FIG. 2, a pressure measurement portion 100 is provided at extracted blood pressure measurement site 2 shown in FIG. 1 and serving as a negative pressure site. Pressure measurement portion 100 includes a housing 110 and blood lines 210, 220 connected to housing 110.

An inlet side joint component 111 via which blood is introduced and an outlet side joint component 112 via which blood is discharged are connected to housing 110. Blood line 210 is inserted in inlet side joint component 111, and blood line 220 is inserted in outlet side joint component 112. It should be noted that although the housing is constituted of one member in the embodiment, the housing may be constituted of a combination of two halved members.

Housing 110 is provided with a pressure measurement port 140, and a pressure monitor line 240 is connected to pressure measurement port 140. A connector 241 at the tip of pressure monitor line 240 is connected to the pressure transducer. A clip 242 is attached to pressure monitor line 240 to close pressure monitor line 240.

Figure 3:
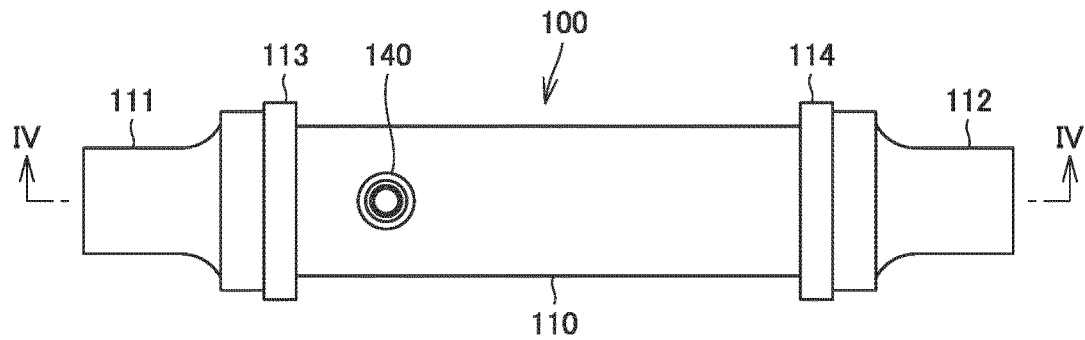
FIG. 3 is a plan view of the pressure measurement portion for measuring negative pressure according to the first embodiment.

With reference to FIG. 3, inlet side joint component 111 and outlet side joint component 112 provided in housing 110 are provided on the same straight line to allow for smooth flow of blood from inlet side joint component 111 to outlet side joint component 112.

Housing 110, which has a cylindrical shape, has a longitudinal side along a direction from inlet side joint component 111 to outlet side joint component 112. Housing 110 is provided with pressure measurement port 140 extending orthogonal to the direction from inlet side joint component 111 to outlet side joint component 112. Pressure measurement port 140 are disposed not in parallel with inlet side joint component 111 and outlet side joint component 112.

Figure 4:
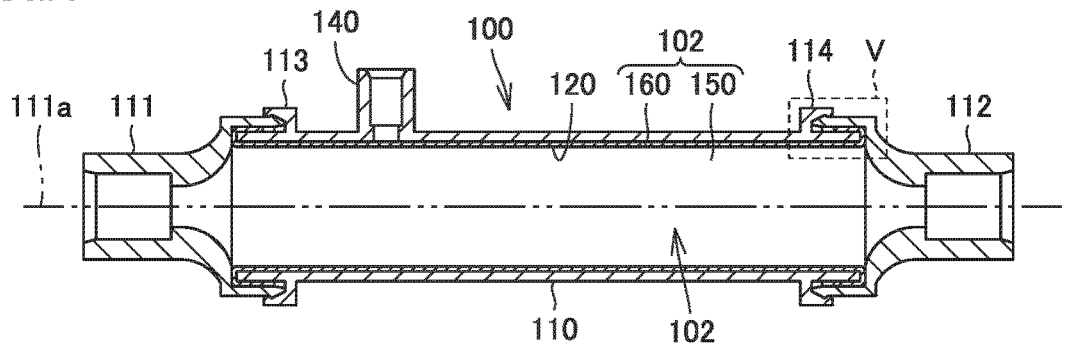
FIG. 4 is a cross sectional view taken along a IV-IV line in FIG. 3.

With reference to FIG. 4, housing 110 is hollow. The hollow space of housing 110 extends from inlet side joint component 111 to outlet side joint component 112. At the both ends of housing 110, engagement portions 113, 114 are provided to be engaged with inlet and outlet side joint components 111, 112.

A distance between the inner circumferential surface of housing 110 and a flexible membrane 120 is about between 0 to 2 mm. Flexible membrane 120 divides chamber 102 of the housing into two spaces. Chamber 102 is divided into: a blood chamber 150 through which blood passes; and an air chamber 160 including air for measuring pressure.

Blood is introduced from inlet side joint component 111 into blood chamber 150. Blood in blood chamber 150 is discharged from outlet side joint component 112. Since flexible membrane 120 is elastic and is deformable, the volume of blood chamber 150 is variable.

Air chamber 160 is formed in a small space between flexible membrane 120 and housing 110 in FIG. 4. Since flexible membrane 120 is deformable in the tube inward direction, the volume of air chamber 160 is also variable.

Flexible membrane 120 having the cylindrical shape has a central axis in parallel with a line 111a extending from inlet side joint component 111 to outlet side joint component 112.

Pressure measurement port 140 communicates with air chamber 160, but does not communicate with blood chamber 150. When flexible membrane 120 is displaced according to flow of blood in blood chamber 150 to change the volume of air chamber 160, this change in volume is notified to the transducer, whereby blood pressure can be measured by the transducer.

A plurality of ribs may be provided in the inner circumferential surface of housing 110. Each of these ribs has a function of increasing strength of housing 110 to stabilize the posture of housing 110.

Further, the rib thus provided facilitates insertion of flexible membrane 120 into housing 110. Flexible membrane 120 is located close to, but not in intimate contact with, the inner circumferential surface of housing 110.

Figure 5:
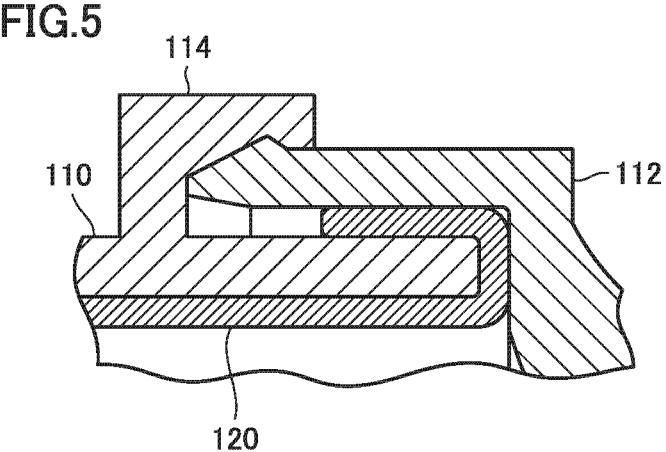
FIG. 5 is an enlarged cross sectional view showing a portion surrounded by V in FIG. 4.

With reference to FIG. 5, outlet side joint component 112 is engaged with engagement portion 114 of housing 110. Between outlet side joint component 112 and the tubular portion of housing 110, flexible membrane 120 is sandwiched. Accordingly, flexible membrane 120 is fixed to housing 110. An advantage of the fixing method of FIG. 5 lies in a large sealing surface and small leak risk.

Figure 6:
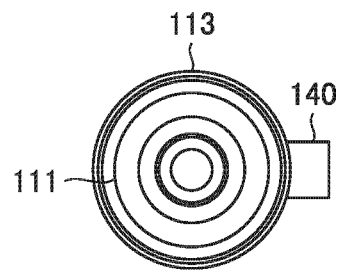
FIG. 6 is a side view of the pressure measurement portion for measuring negative pressure according to the first embodiment.

With reference to FIG. 6, inlet side joint component 111 is engaged with engagement portion 113. Pressure measurement port 140 projects toward the outer circumferential side relative to engagement portion 113. In this figure, engagement portion 113 has a circular outer shape; however, engagement portion 113 may have a polygonal outer shape.

Figure 7:
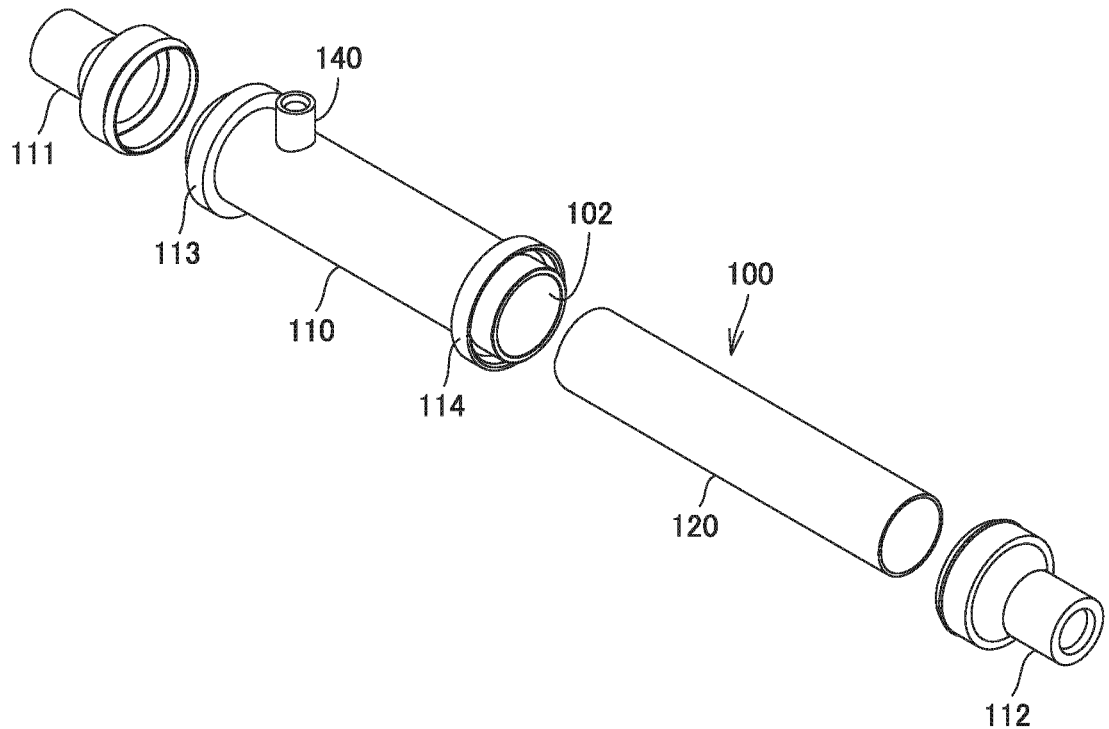
FIG. 7 is an exploded perspective view of the pressure measurement portion for measuring negative pressure according to the first embodiment.

With reference to FIG. 7, flexible membrane 120 is inserted into chamber 102 in housing 110. The natural length of flexible membrane 120 is longer than the length of housing 110, the end portions of flexible membrane 120 are folded and are fixed between engagement portion 113 and inlet side joint component 111 and between engagement portion 114 and outlet side joint component 112.

Figure 8:
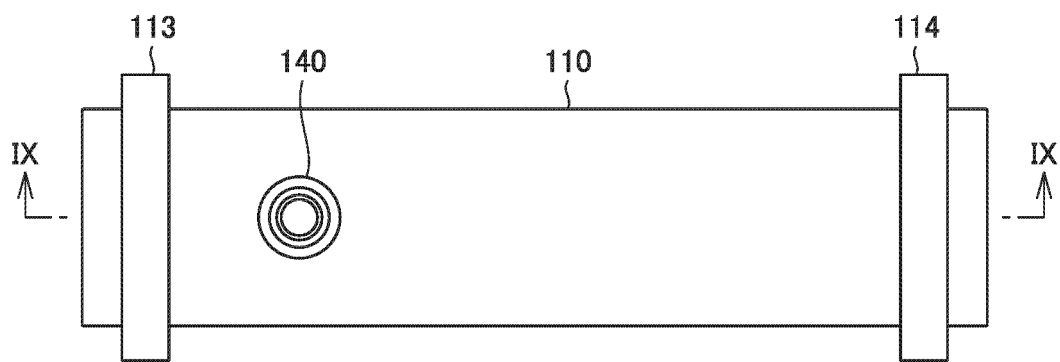
FIG. 8 is a plan view of a housing of the pressure measurement portion for measuring negative pressure according to the first embodiment.
Figure 9:
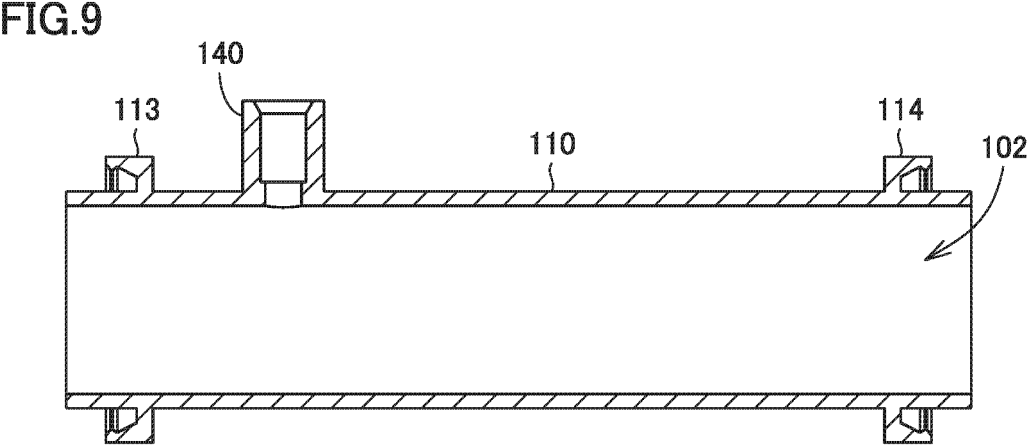
FIG. 9 is a cross sectional view taken along a IX-IX line in FIG. 8.
Figure 10:
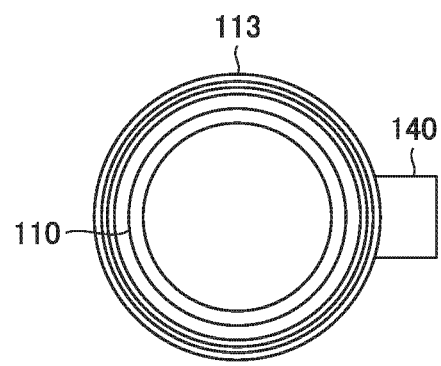
FIG. 10 is a side view of the housing of the pressure measurement portion for measuring negative pressure according to the first embodiment.

With reference to FIGS. 8 to 10, housing 110 has such a shape that ring-like engagement portions 113, 114 are attached to the both end sides of the tubular member. Moreover, pressure measurement port 140 is disposed between engagement portion 113 and engagement portion 114. Pressure measurement port 140 having the tubular shape communicates with chamber 102 of housing 110, and pressure in chamber 102 can be measured from pressure measurement port 140.

Figure 11:
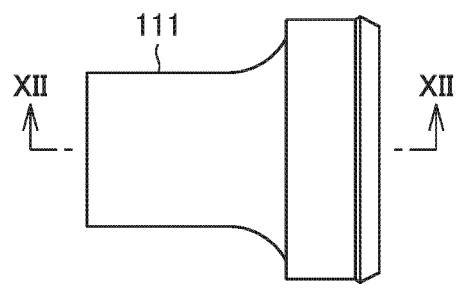
FIG. 11 is a front view of a joint component of the pressure measurement portion for measuring negative pressure according to the first embodiment.
Figure 12:
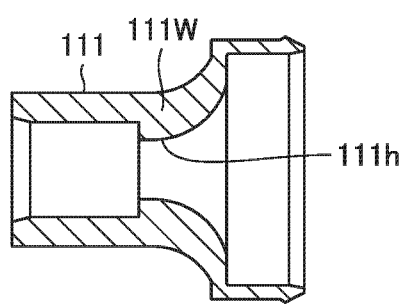
FIG. 12 is a cross sectional view taken along a XII-XII line in FIG. 11.
Figure 13:
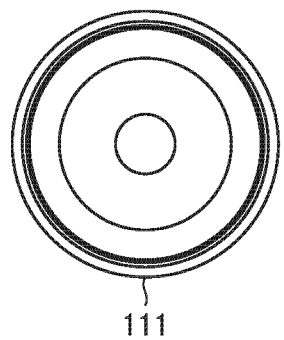
FIG. 13 is a side view of the joint component of the pressure measurement portion for measuring negative pressure according to the first embodiment.

With reference to FIGS. 11 to 13, a separation wall 111w is provided in inlet side joint component 111, and is provided with a through hole 111h. Inlet side joint component 111 communicates with the blood chamber via through hole 111h. Similar separation wall and through hole are also provided in the outlet side joint component.

Figure 14:
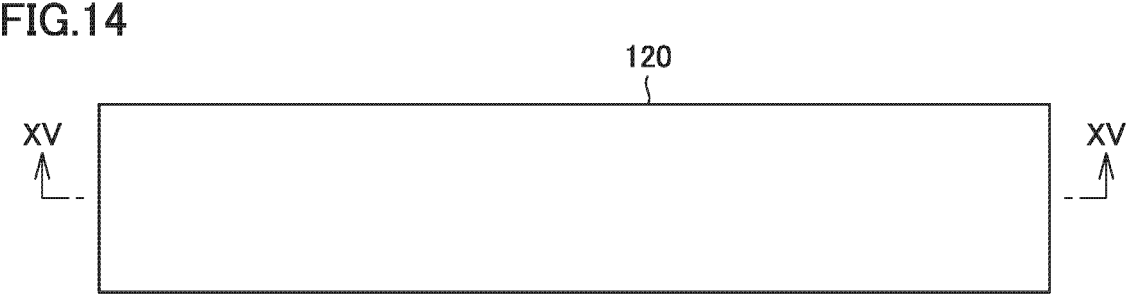
FIG. 14 is a front view of a flexible membrane of the pressure measurement portion for measuring negative pressure according to the first embodiment.
Figure 15:
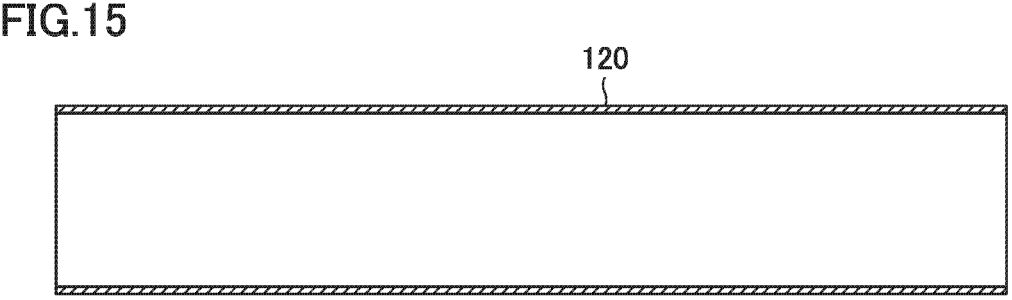
FIG. 15 is a cross sectional view taken along a XV-XV line in FIG. 14.

With reference to FIGS. 14 and 15, flexible membrane 120 has a substantially cylindrical shape in which blood flows. In the present embodiment, flexible membrane 120 has a cylindrical shape; however, the shape of flexible membrane 120 does not need to be the cylindrical shape and may be a quadrangular tubular shape. Alternatively, the shape of flexible membrane 120 may be an elliptic tubular shape.

Further, in the present embodiment, the outer diameter and inner diameter of flexible membrane 120 are constant but do not need to be constant. The outer diameter and the inner diameter of flexible membrane 120 may be non-uniform.

Second Embodiment

Figure 16:
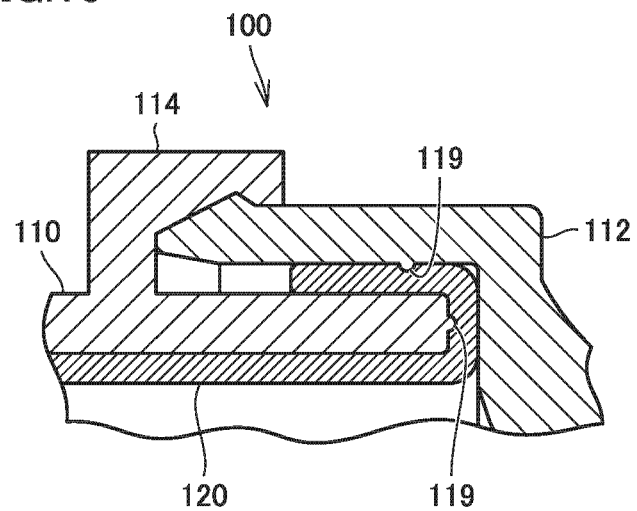
FIG. 16 is an enlarged cross sectional view showing an engagement portion of a housing, a flexible membrane, and a joint component in a pressure measurement portion for measuring negative pressure according to a second embodiment.
Figure 17:
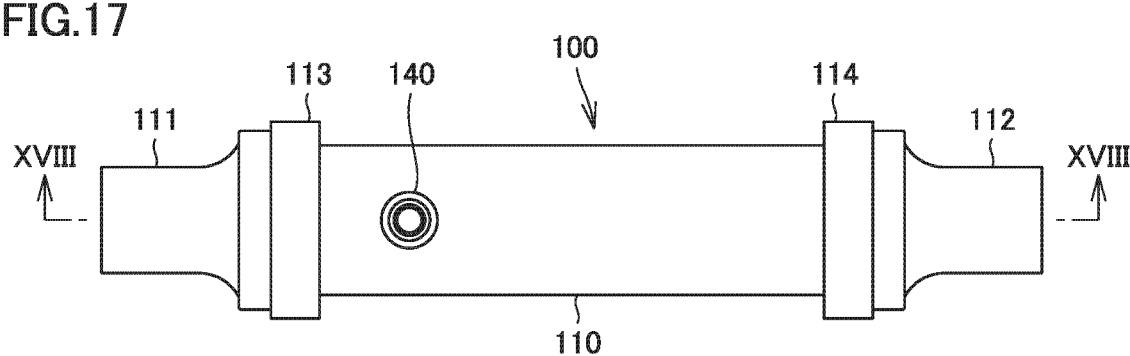
FIG. 17 is a plan view of a pressure measurement portion for measuring negative pressure according to a third embodiment.
Figure 18:
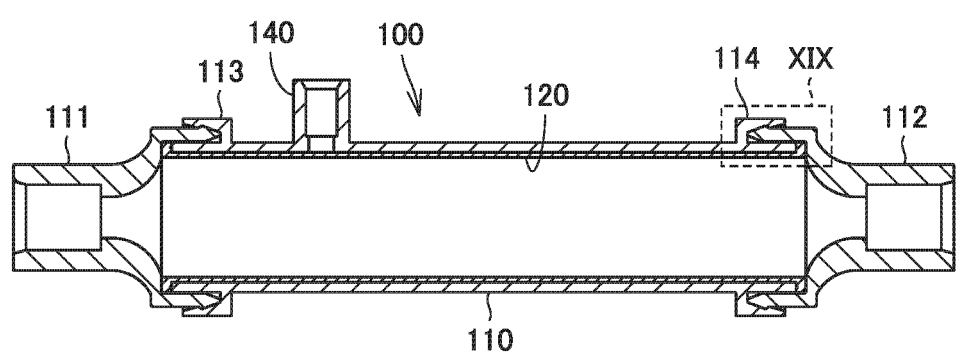
FIG. 18 is a cross sectional view taken along a XVIII-XVIII line in FIG. 17.
Figure 19:
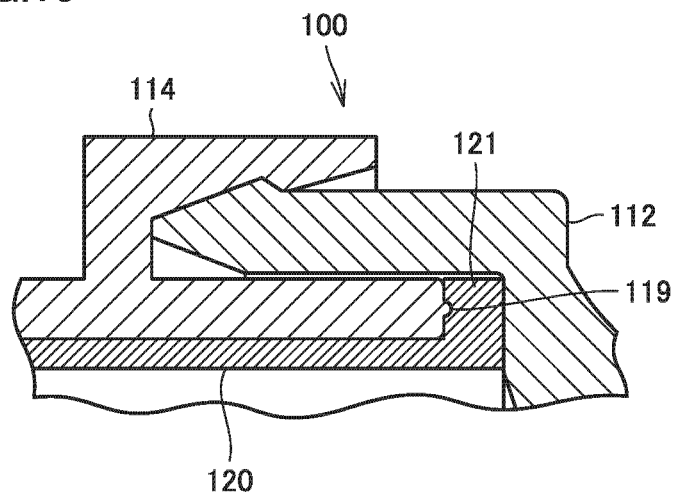
FIG. 19 is a cross sectional view taken along a XIX-XIX line in FIG. 18.
Figure 20:
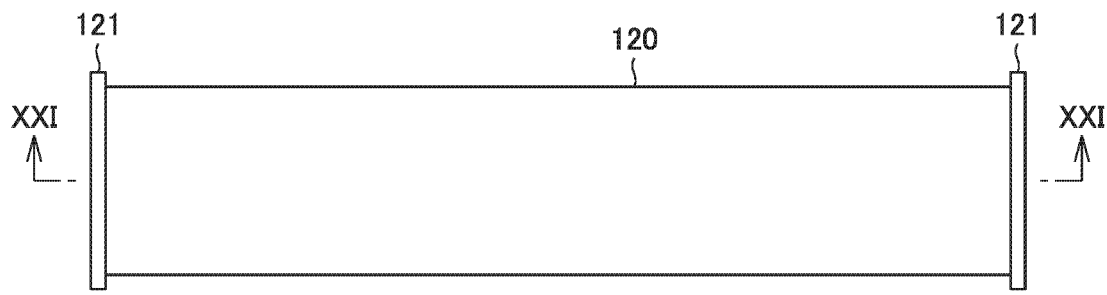
FIG. 20 is a front view of a flexible membrane of the pressure measurement portion for measuring negative pressure according to the third embodiment.
Figure 21:
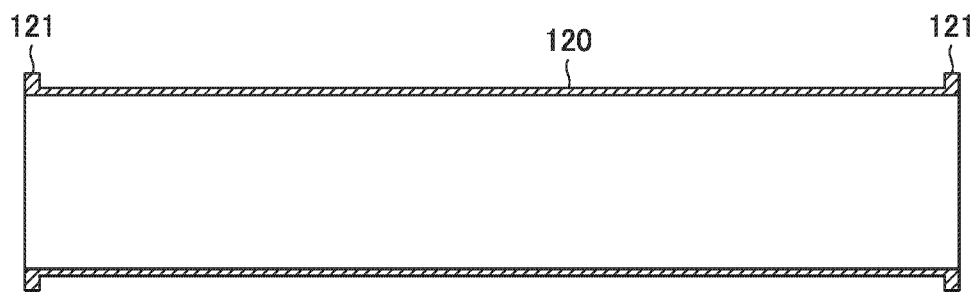
FIG. 21 is a cross sectional view taken along a XXI-XXI line in FIG. 20.

With reference to FIG. 16, each of a housing 110 and an outlet side joint component 112 according to a second embodiment is provided with a rib 119 for securely fixing and holding flexible membrane 120 to improve a sealing property.

In the present embodiment, rib 119 is provided in each of housing 110 and outlet side joint component 112; however, rib 119 may be provided only in housing 110 or only in outlet side joint component 112. It should be noted that rib 119 may be provided in an inlet side joint component 111.

Third Embodiment

With reference to FIGS. 17 to 21, a pressure measurement portion 100 according to a third embodiment is provided with a thick membrane portion 121 obtained by forming an end portion of flexible membrane 120 in a non-planar manner. The thickness of thick membrane portion 121 is thicker than the thicknesses of the other portions. Presence of thick membrane portion 121 facilitates engagement of the end portions of flexible membrane 120 with inlet and outlet side joint components 111, 112 and housing 110. As a result, sealing property at each of the end portions can be improved. An advantage of the fixing method of FIG. 17 lies in that assembling is facilitated as compared with that in FIG. 5.

It should be noted that in the present embodiment, a rib 119 is provided in housing 110 to press thick membrane portion 121, thereby further improving the sealing property. Rib 119 may be provided in each of the inlet and outlet side joint components 111, 112.

Fourth Embodiment

Figure 22:
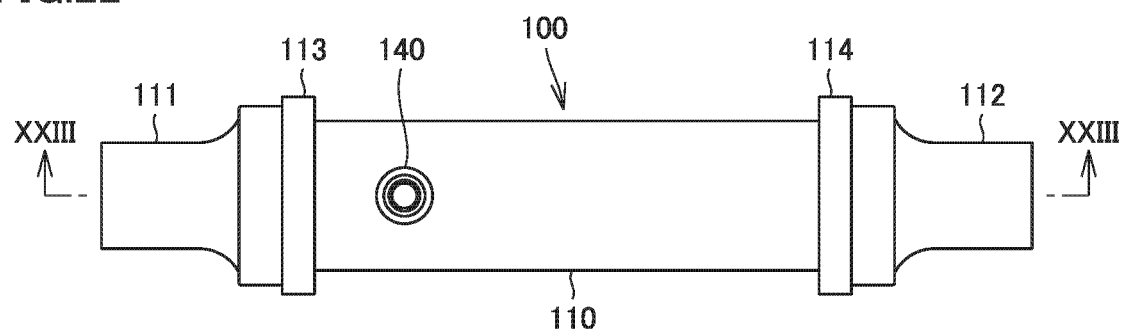
FIG. 22 is a plan view of a pressure measurement portion for measuring negative pressure according to a fourth embodiment.
Figure 23:
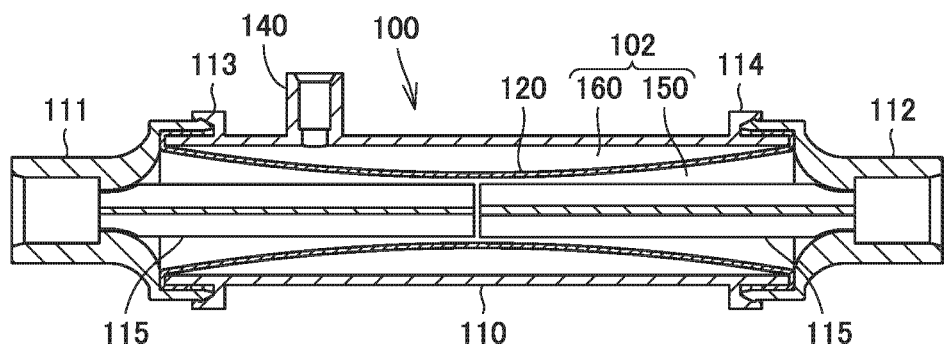
FIG. 23 is a cross sectional view taken along a XXIII-XXIII line in FIG. 22.

With reference to FIGS. 22 and 23, in a pressure measurement portion 100 according to a fourth embodiment, a flexible membrane 120 is provided with closure suppression members 115.

In housing 110, closure suppression members 115 extend from inlet side joint component 111 to outlet side joint component 112. Each of closure suppression members 115 is configured to prevent flexible membrane 120 from blocking flow of blood. Since closure suppression members 115 exist inside flexible membrane 120, a space is generated between portions of flexible membrane 120 facing each other. Blood flows in this space, thereby preventing retention of blood therein. It is necessary to suppress the retention of blood because the retention of blood causes destruction of platelets.

As shown in FIG. 23, a closure suppression member 115 is provided in inlet side joint component 111 and is inserted in flexible membrane 120, and a closure suppression member 115 is provided in outlet side joint component 112 and is inserted in flexible membrane 120.

Figure 24:
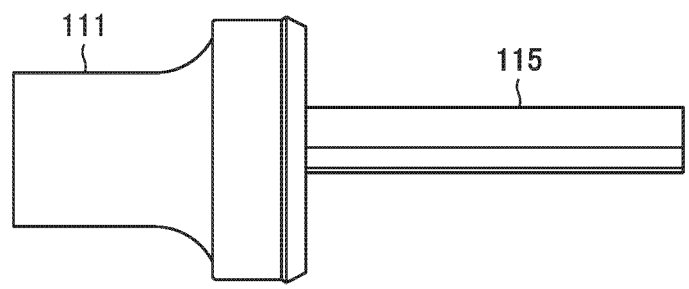
FIG. 24 is a front view of a joint component of the pressure measurement portion for measuring negative pressure according to the fourth embodiment.
Figure 25:
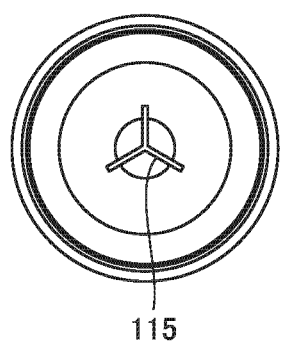
FIG. 25 is a side view of the joint component of the pressure measurement portion for measuring negative pressure according to the fourth embodiment.
Figure 26:
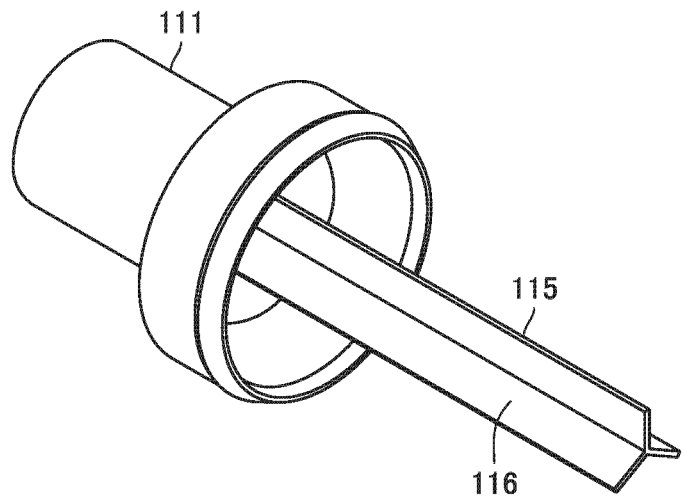
FIG. 26 is a perspective view of the joint component of the pressure measurement portion for measuring negative pressure according to the fourth embodiment.

With reference to FIGS. 24 to 26, in each closure suppression member 115 according to the present embodiment, three plate-like members 116 extend radially from the central portion, thereby forming blood flow paths between plate-like members 116.

Although two closure suppression members 115 are inserted in flexible membrane 120, only one closure suppression member 115 may be provided inside flexible membrane 120 by extending one closure suppression member 115.

Further, although FIG. 23 illustrates that closure suppression member 115 provided in inlet side joint component 111 has a length equal to the length of closure suppression member 115 provided in the outlet side joint component, the lengths are not limited to these and one closure suppression member 115 may be formed to be longer than the other closure suppression member 115. Although each plate-like member 116 has a flat shape, plate-like member 116 may have a curved shape.

Fifth Embodiment

Figure 27:
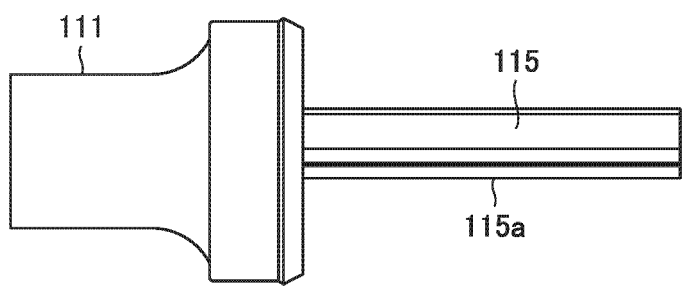
FIG. 27 is a front view of a joint component of a pressure measurement portion for measuring negative pressure according to a fifth embodiment.
Figure 28:
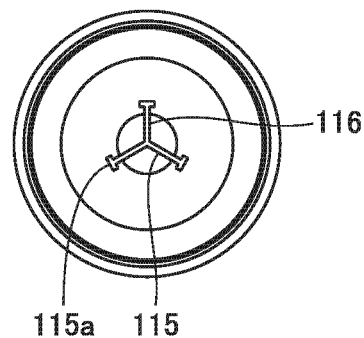
FIG. 28 is a side view of the joint component of the pressure measurement portion for measuring negative pressure according to the fifth embodiment.
Figure 29:
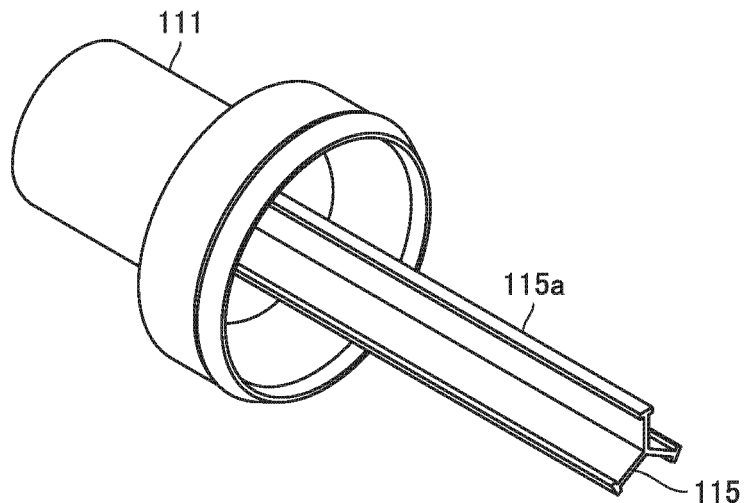
FIG. 29 is a perspective view of the joint component of the pressure measurement portion for measuring negative pressure according to the fifth embodiment.

With reference to FIGS. 27 to 29, in an inlet side joint component 111 used in a fifth embodiment, a wall surface 115a extending in the circumferential direction is provided at the outer circumferential end of a plate-like member 116 of a closure suppression member 115.

Wall surface 115a may be a flat surface or a curved surface. Because wall surface 115a is configured to come into abutment with flexible membrane 120 to secure a blood flow path, wall surface 115a is shaped not to damage flexible membrane 120. It should be noted that wall surface 115a shown in FIGS. 27 to 29 may be employed for outlet side joint component 112.

Sixth Embodiment

Figure 30:
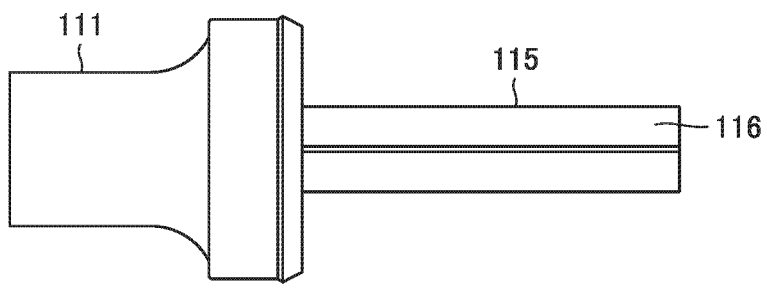
FIG. 30 is a front view of a joint component of a pressure measurement portion for measuring negative pressure according to a sixth embodiment.
Figure 31:
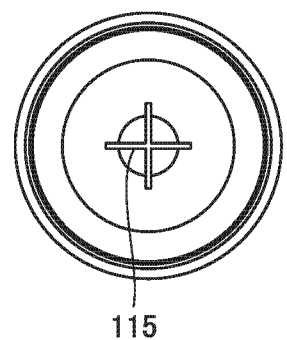
FIG. 31 is a side view of the joint component of the pressure measurement portion for measuring negative pressure according to the sixth embodiment.
Figure 32:
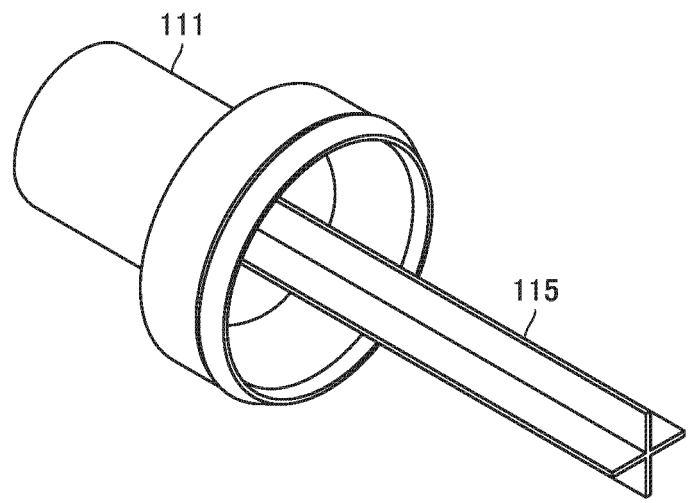
FIG. 32 is a perspective view of the joint component of the pressure measurement portion for measuring negative pressure according to the sixth embodiment.

With reference to FIGS. 30 to 32, in an inlet side joint component 111 used in a sixth embodiment, a closure suppression member 115 has four plate-like members 116, which are disposed at an interval of 90° in angle.

Each of plate-like members 116 may have a flat shape or a curved shape. It should be noted that plate-like member 116 shown in FIGS. 30 to 32 may be employed for outlet side joint component 112. Further, a plate-like member 116 having a different shape from that of FIGS. 30 to 32 may be employed for the outlet side joint component.

Seventh Embodiment

Figure 33:
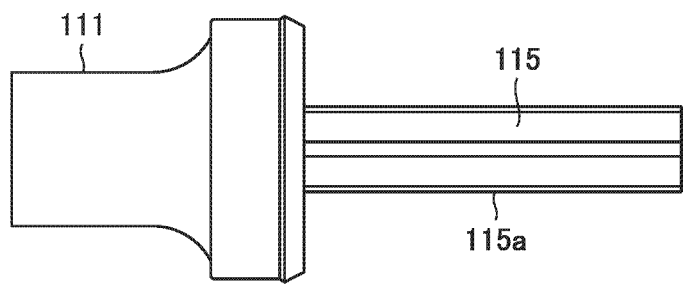
FIG. 33 is a front view of a joint component of a pressure measurement portion for measuring negative pressure according to a seventh embodiment.
Figure 34:
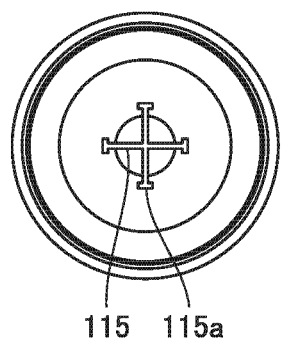
FIG. 34 is a side view of the joint component of the pressure measurement portion for measuring negative pressure according to the seventh embodiment.
Figure 35:
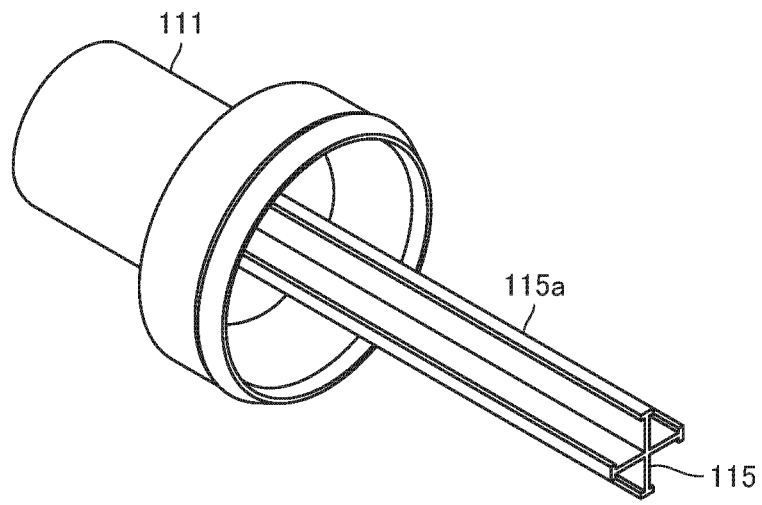
FIG. 35 is a perspective view of the joint component of the pressure measurement portion for measuring negative pressure according to the seventh embodiment.

With reference to FIGS. 33 to 35, in an inlet side joint component 111 used in a seventh embodiment, a wall surface 115a is provided at the outer circumferential end of a plate-like member 116 of a closure suppression member 115 to extend in the circumferential direction.

Wall surface 115a may be a flat surface or a curved surface. Because wall surface 115a is configured to come into abutment with flexible membrane 120 to secure a blood flow path, wall surface 115a is shaped not to damage flexible membrane 120. It should be noted that wall surface 115a shown in FIGS. 33 to 35 may be employed for outlet side joint component 112.

Eighth Embodiment

Figure 36:
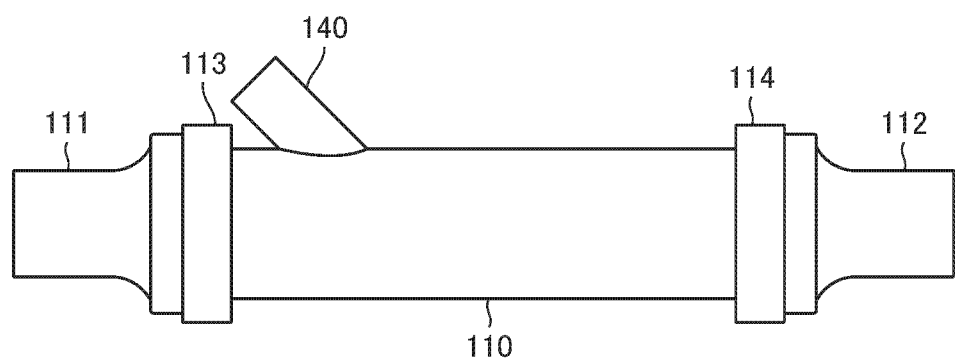
FIG. 36 is a front view of a pressure measurement portion for measuring negative pressure according to an eighth embodiment.
Figure 37:
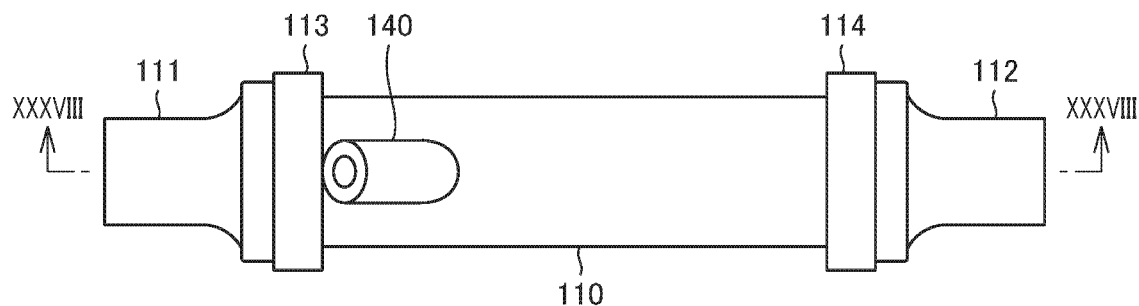
FIG. 37 is a plan view of the pressure measurement portion for measuring negative pressure according to the eighth embodiment.
Figure 38:
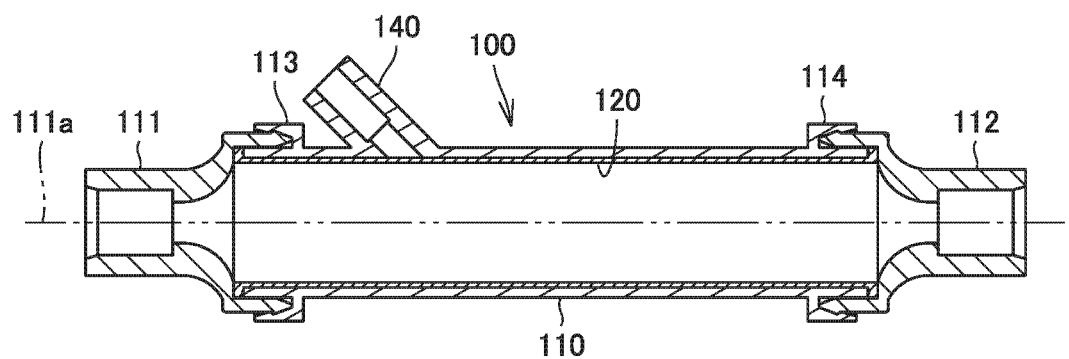
FIG. 38 is a cross sectional view taken along a XXXVIII-XXXVIII line in FIG. 37.

With reference to FIGS. 36 to 38, in a pressure measurement portion 100 according to an eighth embodiment, a pressure measurement port 140 forms an acute angle relative to a line 111a connecting an inlet side joint component 111 to an outlet side joint component 112. Since pressure measurement port 140 is provided to be inclined, pressure measurement port 140 can be made small in size.

Ninth Embodiment

Figure 39:
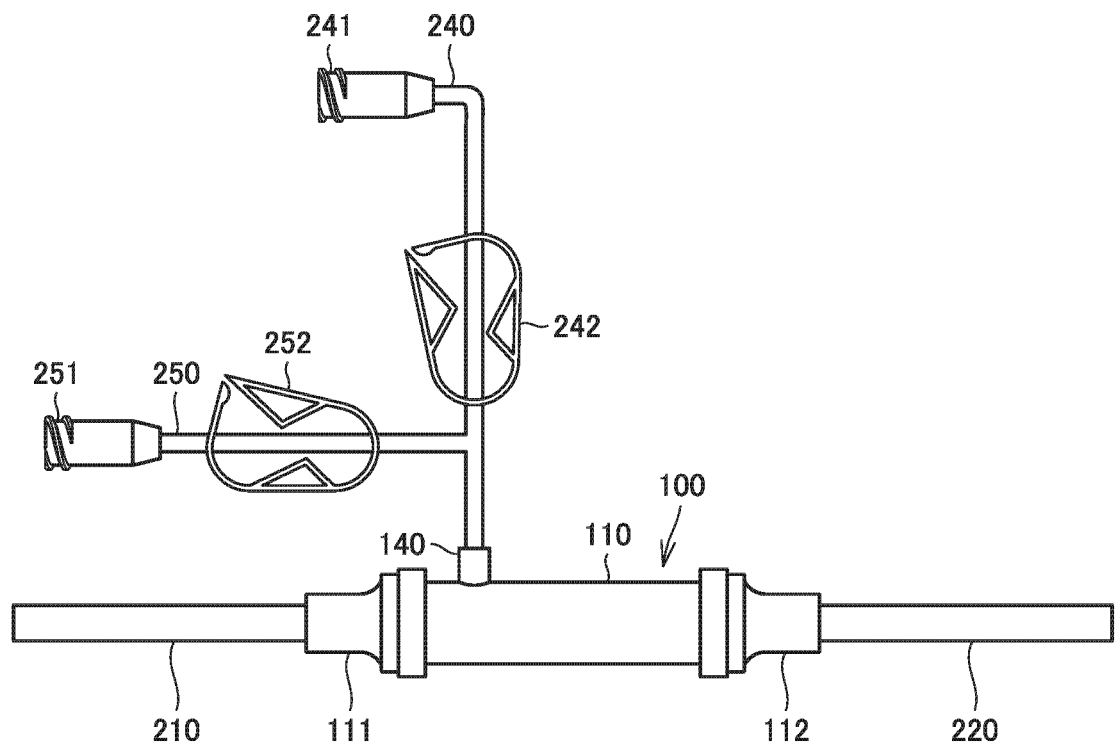
FIG. 39 is a front view of a pressure measurement portion for measuring negative pressure according to a ninth embodiment.

With reference to FIG. 39, in a pressure measurement portion 100 according to a ninth embodiment, a fluid level adjustment line 250 is connected to a pressure monitor line 240 to adjust a fluid level in pressure monitor line 240. Fluid level adjustment line 250 is provided with a clip 252 and a connector 251.

Tenth Embodiment

Figure 40:
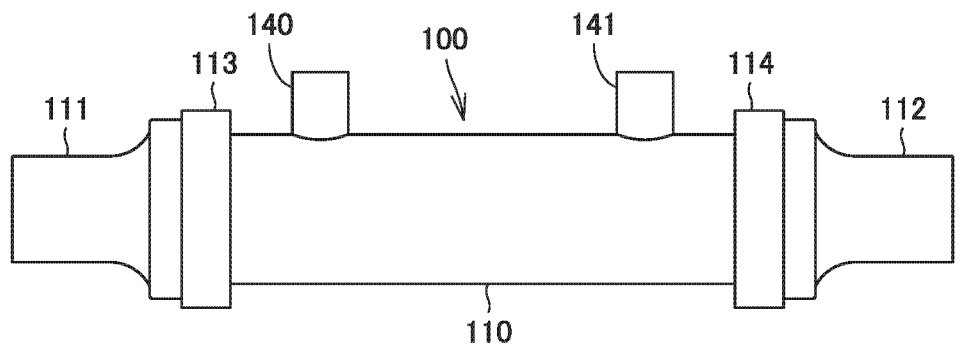
FIG. 40 is a front view of a pressure measurement portion for measuring negative pressure according to a tenth embodiment.
Figure 41:
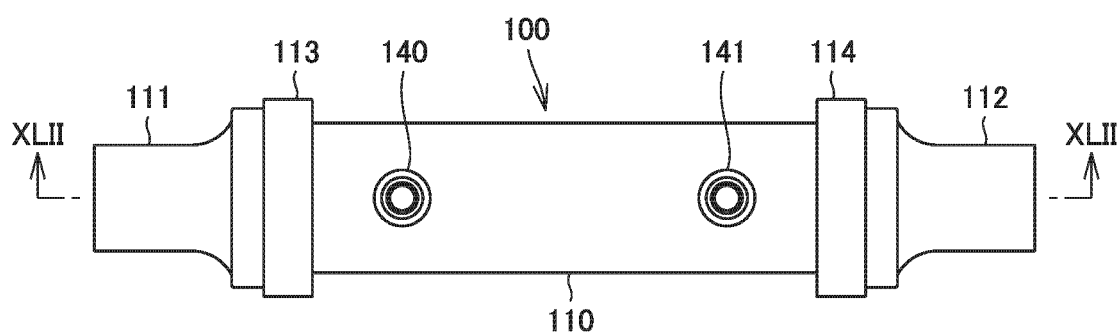
FIG. 41 is a plan view of the pressure measurement portion for measuring negative pressure according to the tenth embodiment.
Figure 42:
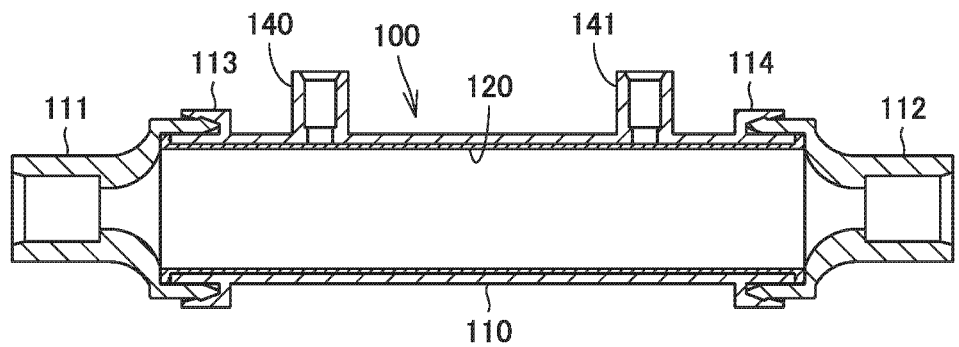
FIG. 42 is a cross sectional view taken along a XLII-XLII line in FIG. 41.

With reference to FIGS. 40 to 42, in a pressure measurement portion 100 according to a tenth embodiment, a fluid level adjustment port 141 is provided in a housing 110. Fluid level adjustment line 250 shown in FIG. 39 is connected to fluid level adjustment port 141 to adjust the fluid level in pressure monitor line 240, and clip 252 and connector 251 are provided in fluid level adjustment line 250.

Eleventh Embodiment

Figure 43:
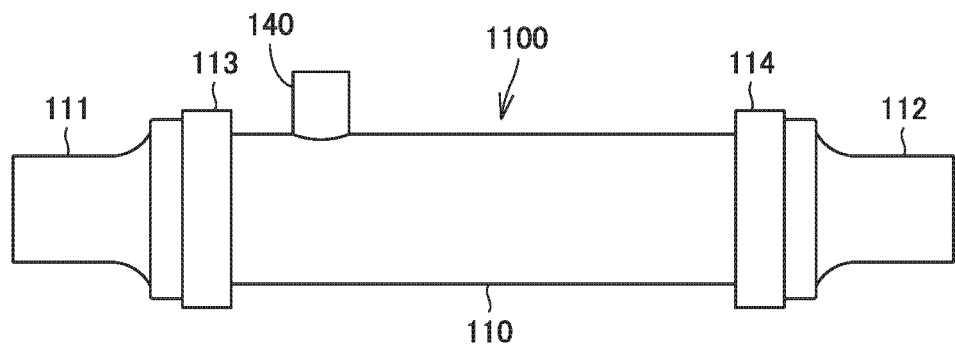
FIG. 43 is a front view of a pressure measurement portion for measuring positive pressure according to a comparative example.
Figure 44:
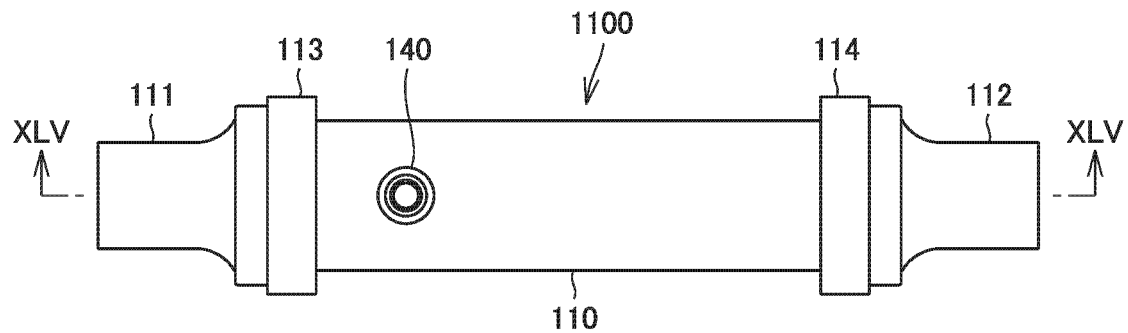
FIG. 44 is a plan view of the pressure measurement portion for measuring positive pressure according to the comparative example.
Figure 45:
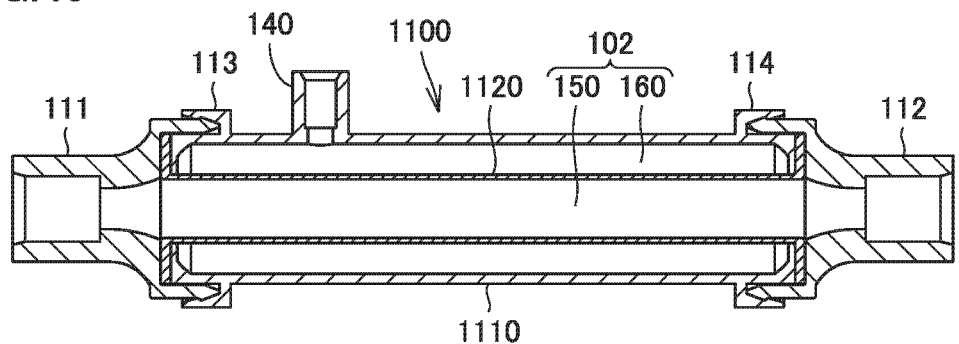
FIG. 45 is a cross sectional view taken along a XLV-XLV line in FIG. 44.

With reference to FIGS. 43 to 45 illustrating a comparative example, in a pressure measurement portion 1110 for measuring positive pressure, a flexible membrane 1120 having a cylindrical shape and having a circular cross section is expanded, so that a large space is formed between flexible membrane 1120 and housing 1110 to provide an air chamber 160. In order to expand flexible membrane 1120, it is necessary to extend flexible membrane 1120. When the positive pressure is large, flexible membrane 1120 can be extended using this positive pressure. However, since part of the positive pressure is used to extend flexible membrane 1120, positive pressure cannot be measured correctly without correction.

Figure 46:
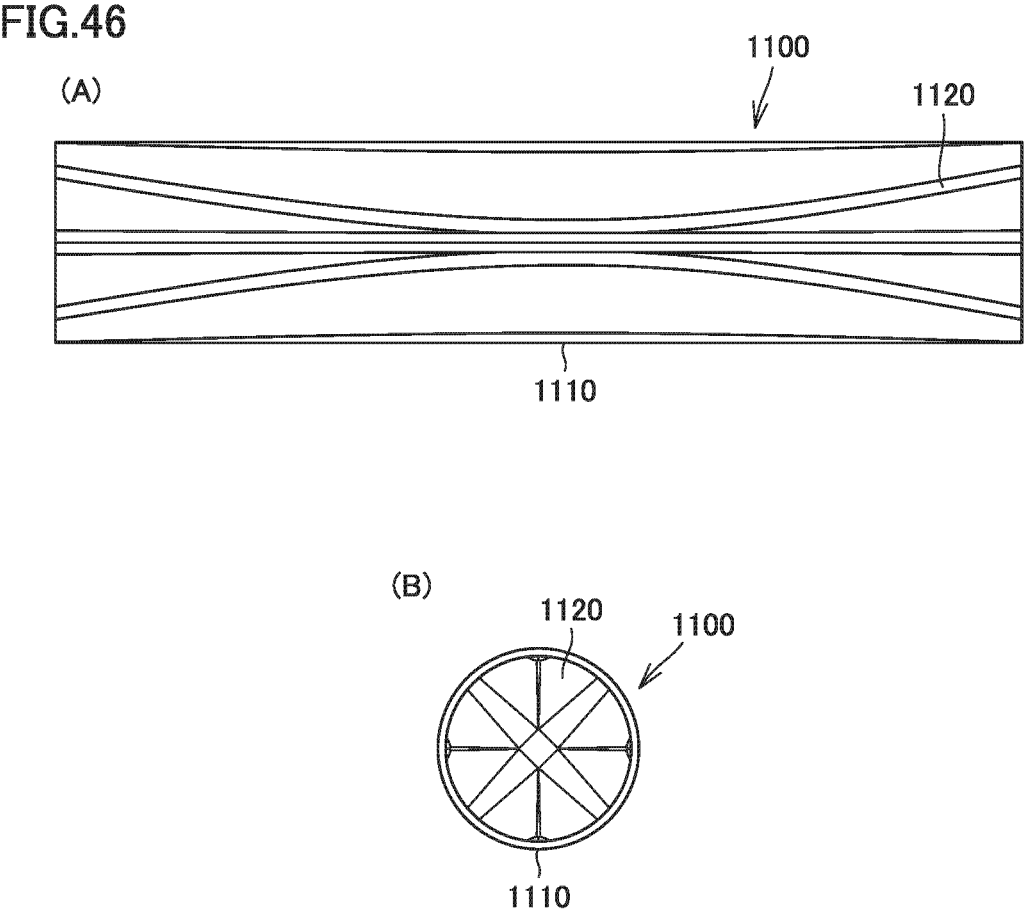
FIG. 46 (A) is a front view of a flexible membrane of a pressure measurement portion for measuring positive pressure according to an eleventh embodiment, and FIG. 46 (B) is a side view of the flexible membrane of the pressure measurement portion for measuring positive pressure according to the eleventh embodiment.
Figure 47:
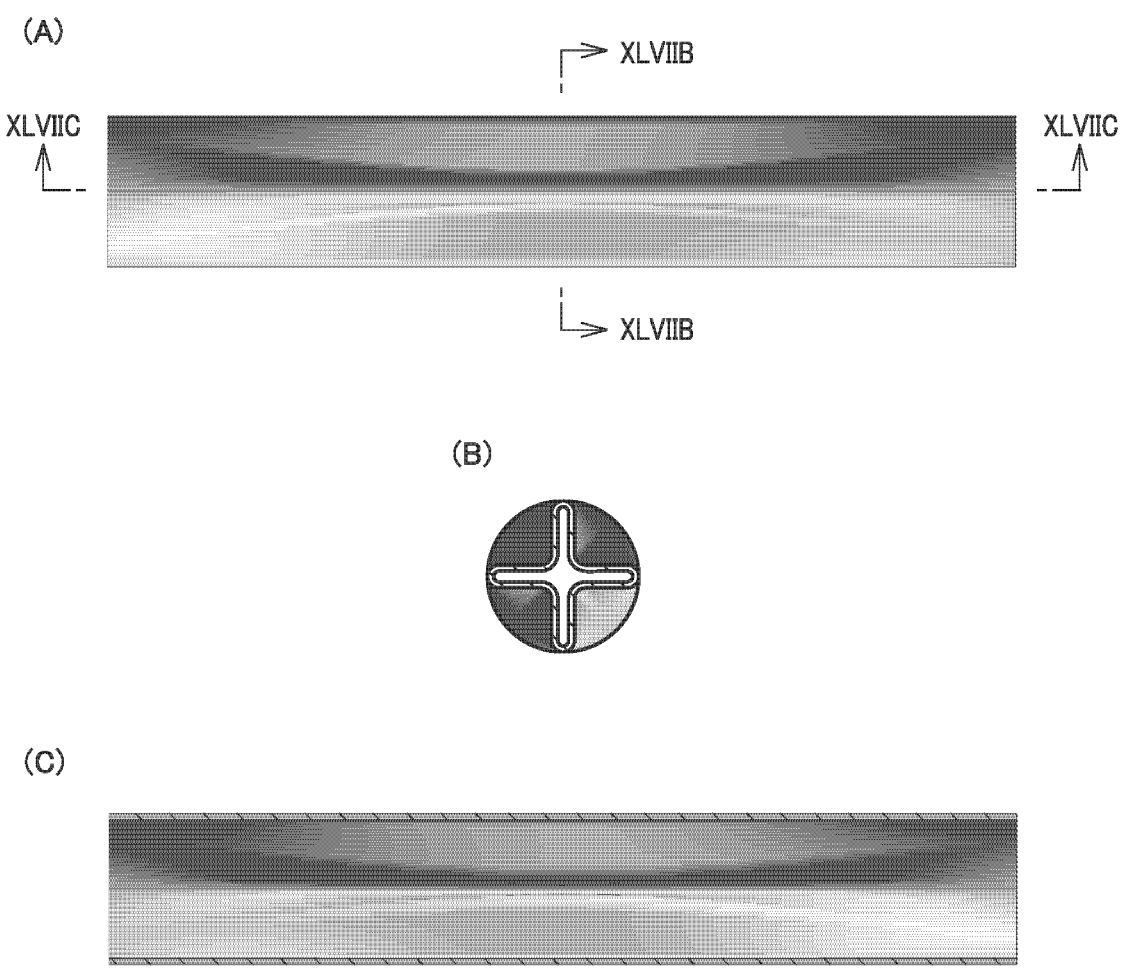
FIG. 47 (A) is a plan view of the flexible membrane of the pressure measurement portion for measuring positive pressure according to the eleventh embodiment, FIG. 47 (B) is a cross sectional view taken along a XLVIIB-XLVIIB line in FIG. 47 (A), and FIG. 47 (C) is a cross sectional view taken along a XLVIIC-XLVIIC line in FIG. 47 (A).

With reference to FIGS. 46 and 47, the central portion of flexible membrane 1120 is in the form of a cross. Flexible membrane 1120 is deformed under application of pressure, but is reverted to its original shape when the application of pressure is ended. It should be noted that flexible membrane 1120 may be configured not to be reverted to the original shape once deformed.

It should be noted that a flexible membrane 1120 longer than housing 1110 may be attached to housing 1110 instead of previously deforming flexible membrane 1120. The flexible membrane longer than housing 1110 is deformed when flexible membrane 1120 is positioned in housing 1110. Since flexible membrane 1120 is deformed when positioned therein, flexible membrane 1120 can be readily deformed using positive pressure.

Figure 48:
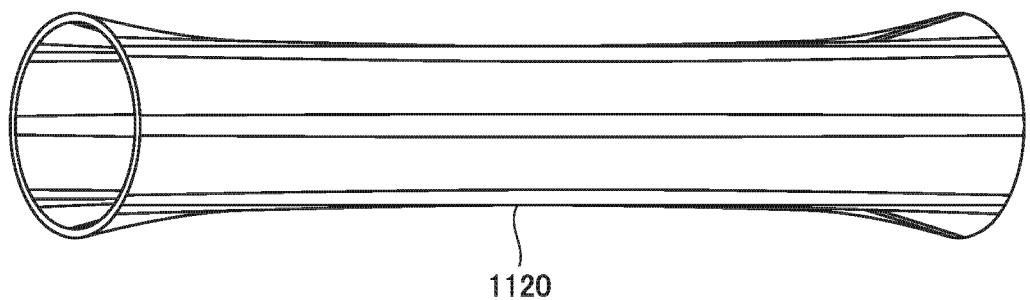
FIG. 48 is a perspective view of the flexible membrane of the pressure measurement portion for measuring positive pressure according to the eleventh embodiment.

With reference to FIG. 48, the diameter of the cross portion of flexible membrane 1120 is constant at the central portion and end portions of flexible membrane 1120. It should be noted that flexible membrane 1120 may be configured to have such a shape that the diameter thereof is small at the central portion and is large at the end portions. The shape of flexible membrane 1120 is not limited to this, and flexible membrane 1120 may be configured to have such a shape that the diameter thereof is large at the central portion and the diameter thereof is large at the end portions.

Further, in order to facilitate flexible membrane 1120 longer than housing 1110 to be stored in housing 1110, flexible membrane 1120 may be twisted and stored in housing 1110. In this case, the length of flexible membrane 1120 can be adjusted based on an angle of twisting.

Pressure measurement portion 11100 for measuring positive pressure is provided at PD (Pre-dialyzer) pressure measurement site 5 or venous pressure measurement site 11 illustrated in FIG. 1 and serving as a positive pressure site.

Twelfth Embodiment

Figure 49:
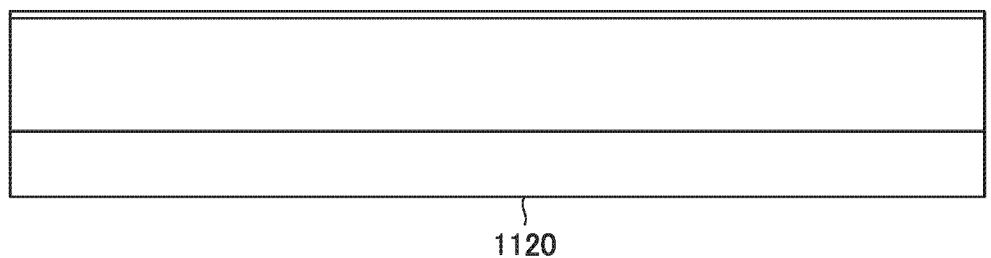
FIG. 49 is a front view of a flexible membrane of a pressure measurement portion for measuring positive pressure according to a twelfth embodiment.
Figure 50:
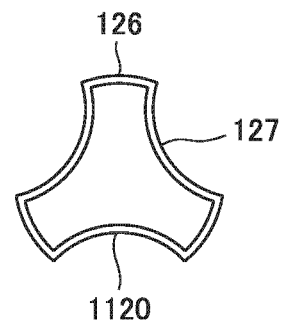
FIG. 50 is a side view of the flexible membrane of the pressure measurement portion for measuring positive pressure according to the twelfth embodiment.
Figure 51:
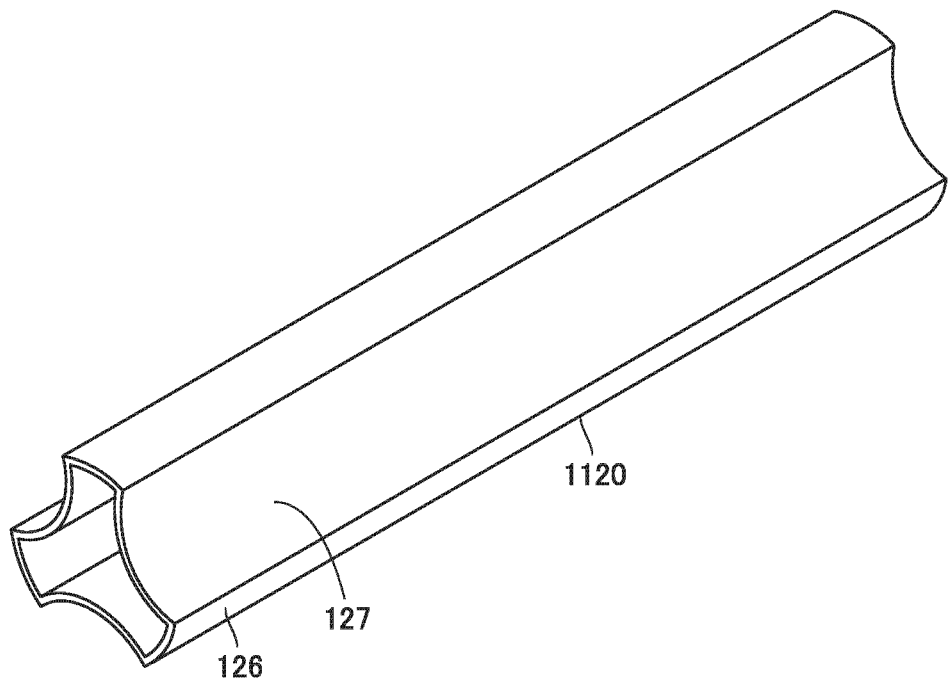
FIG. 51 is a perspective view of the flexible membrane of the pressure measurement portion for measuring positive pressure according to the twelfth embodiment.

With reference to FIGS. 49 to 51, a flexible membrane 1120 in a pressure measurement portion according to a twelfth embodiment is provided with projections 126 and recesses 127, and each recess 127 of flexible membrane 1120 can be deformed in the tube outward direction readily due to positive pressure in flexible membrane 1120. As a result, the positive pressure can be measured with high precision. In the present embodiment, recess 127 and projection 126 extend from the one end to the other end of flexible membrane 1120 along the axial direction; however, recess 127 and projection 126 do not necessarily need to extend to the end portions as long as recess 127 and projection 126 are provided in at least a portion of flexible membrane 1120.

When the apex of projection 126 is located close to housing 1110, the volume of the air chamber does not become large, thus attaining a compact pressure measurement portion.

Thirteenth Embodiment

Figure 52:
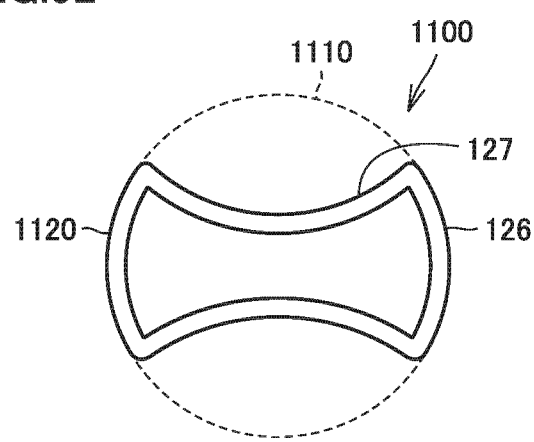
FIG. 52 is a side view of a flexible membrane of a pressure measurement portion for measuring positive pressure according to a thirteenth embodiment.

With reference to FIG. 52, a flexible membrane 1120 in a pressure measurement portion according to a thirteenth embodiment is different from flexible membrane 1120 according to the twelfth embodiment in that flexible membrane 1120 in the pressure measurement portion according to the thirteenth embodiment is provided with two projections 126 and two recesses 127.

Fourteenth Embodiment

Figure 53:
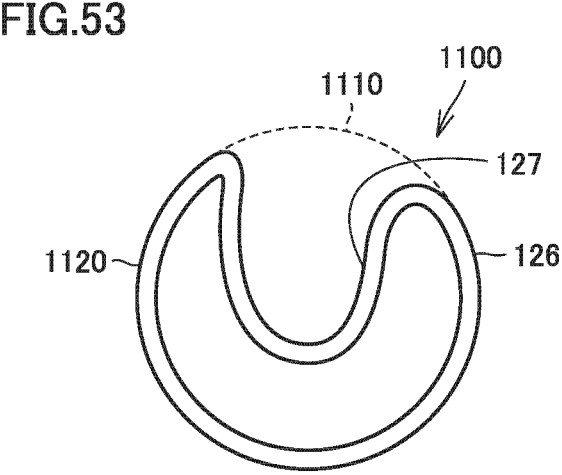
FIG. 53 is a side view of a flexible membrane of a pressure measurement portion for measuring positive pressure according to a fourteenth embodiment.

With reference to FIG. 53, a flexible membrane 1120 in a pressure measurement portion according to a fourteenth embodiment is different from flexible membrane 1120 according to the twelfth embodiment in that flexible membrane 1120 in the pressure measurement portion according to the fourteenth embodiment is provided with one projection 126 and one recess 127.

Fifteenth Embodiment

Figure 54:
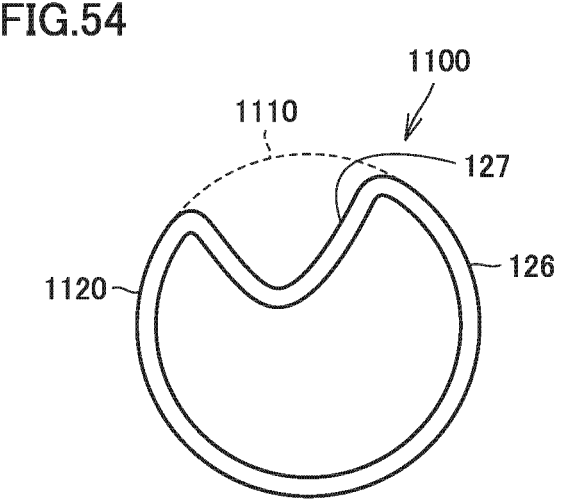
FIG. 54 is a side view of a flexible membrane of a pressure measurement portion for measuring positive pressure according to a fifteenth embodiment.

With reference to FIG. 54, a flexible membrane 1120 in a pressure measurement portion according to a fifteenth embodiment is provided with two projections 126 and two recesses 127 as with the fourteenth embodiment; however, flexible membrane 1120 in the pressure measurement portion according to the fifteenth embodiment is different from flexible membrane 1120 according to the fourteenth embodiment in that a shallower recess 127 is formed than that in the fourteenth embodiment.

Sixteenth Embodiment

Figure 55:
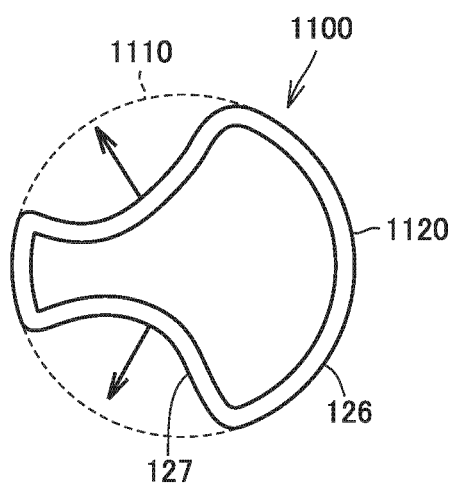
FIG. 55 is a side view of a flexible membrane of a pressure measurement portion for measuring positive pressure according to a sixteenth embodiment.

With reference to FIG. 55, a flexible membrane 1120 in a pressure measurement portion according to a sixteenth embodiment is provided with two projections 126 and two recesses 127 as with the fifteenth embodiment, but is different from flexible membrane 1120 according to the thirteenth embodiment in that two recesses 127 have different widths.

Seventeenth Embodiment

Figure 56:
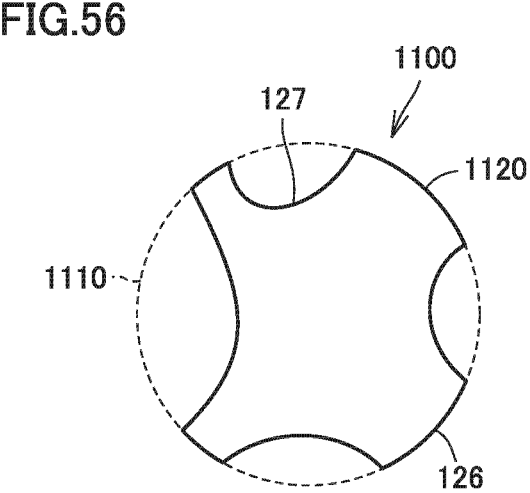
FIG. 56 is a side view of a flexible membrane of a pressure measurement portion for measuring positive pressure according to a seventeenth embodiment.
Figure 57:
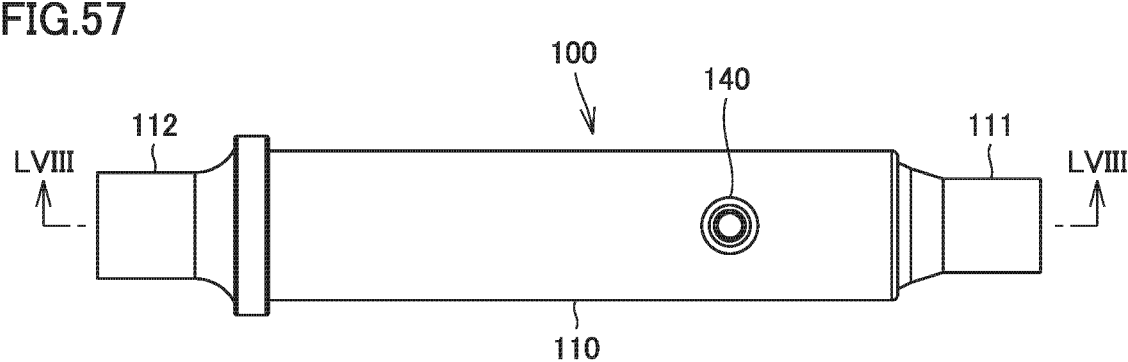
FIG. 57 is a plan view of a pressure measurement portion for measuring negative pressure according to an eighteenth embodiment.
Figure 58:
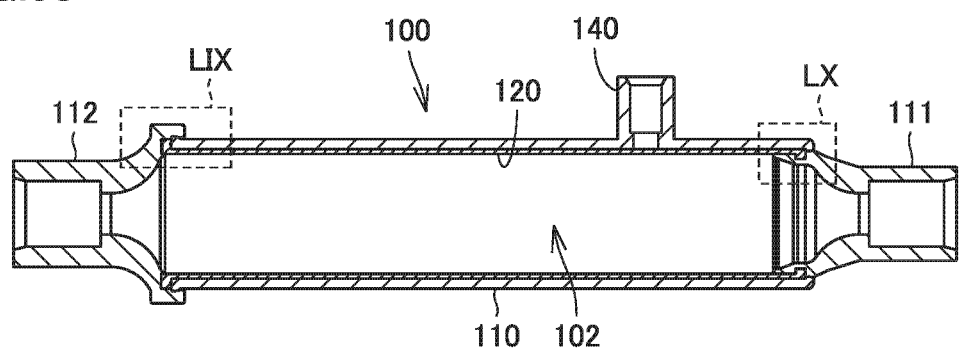
FIG. 58 is a cross sectional view taken along a LVIII-LVIII line in FIG. 57.
Figure 59:
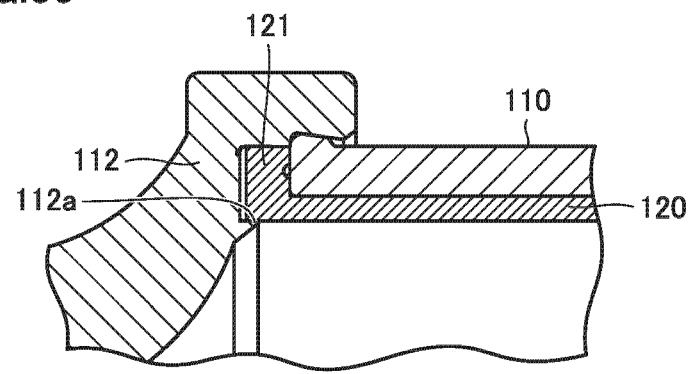
FIG. 59 is an enlarged cross sectional view of a portion surrounded by LIX in each of FIGS. 58 and 76.
Figure 60:
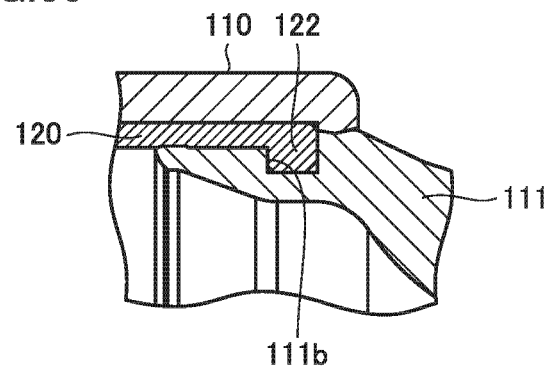
FIG. 60 is an enlarged cross sectional view of a portion surrounded by LX in FIG. 58.
Figure 61:
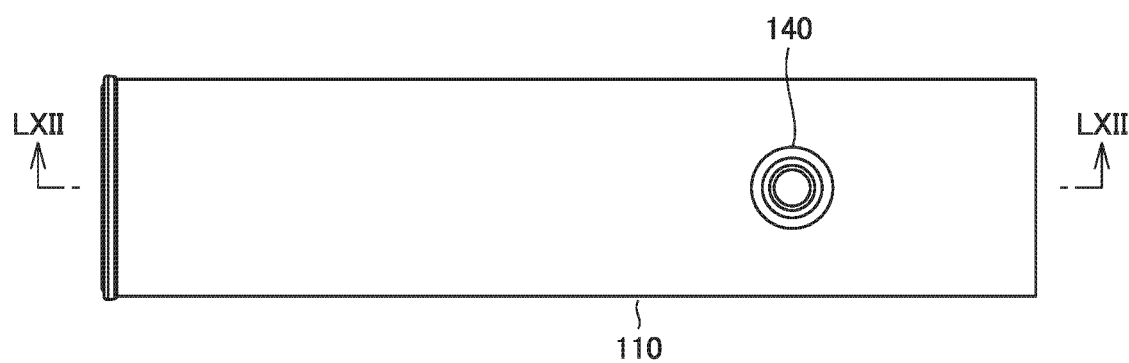
FIG. 61 is a plan view of a housing of the pressure measurement portion for measuring negative pressure according to the eighteenth embodiment.
Figure 62:
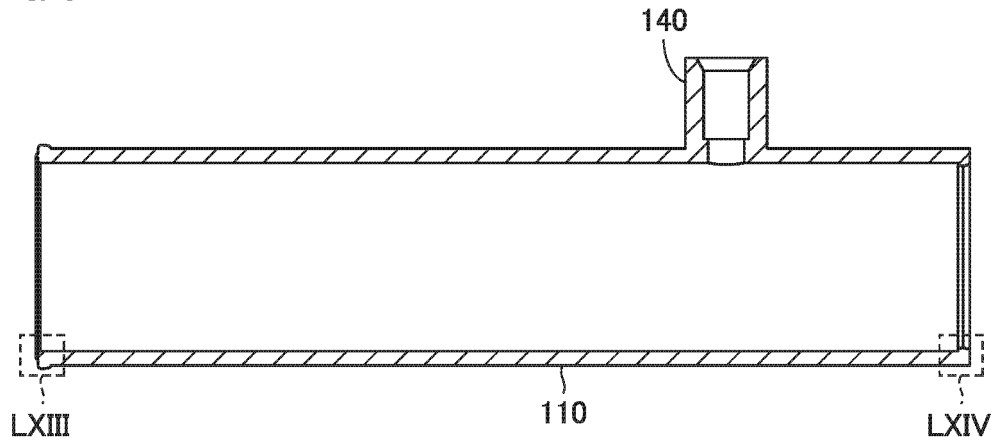
FIG. 62 is a cross sectional view taken along a LXII-LXII line in FIG. 61.
Figure 63:
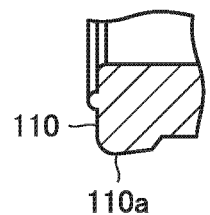
FIG. 63 is an enlarged cross sectional view of a portion surrounded by LXIII in FIG. 62.
Figure 64:
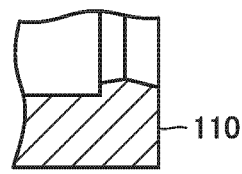
FIG. 64 is an enlarged cross sectional view of a portion surrounded by LXIV in FIG. 62.
Figure 65:
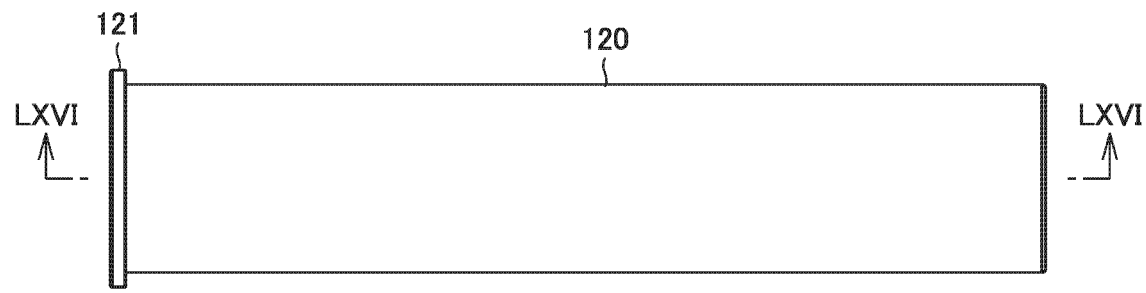
FIG. 65 is a plan view of the flexible membrane of the pressure measurement portion for measuring negative pressure according to the eighteenth embodiment.
Figure 66:
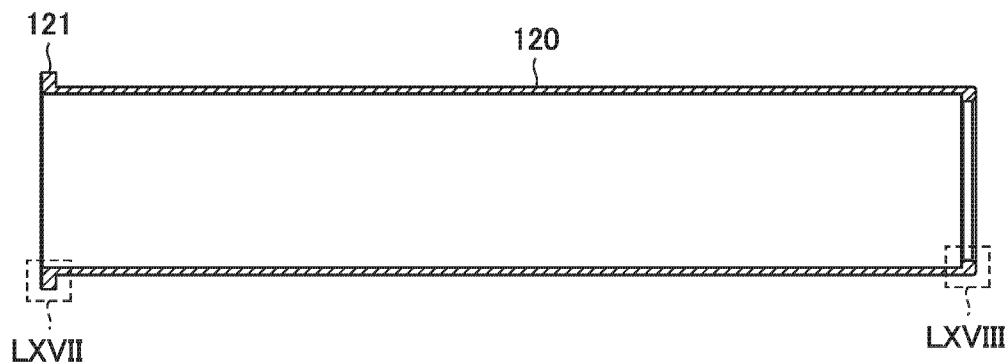
FIG. 66 is a cross sectional view taken along a LXVI-LXVI line in FIG. 65.
Figure 67:
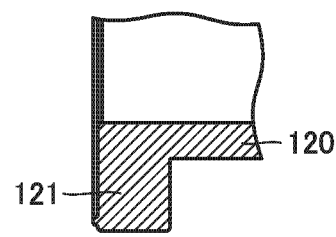
FIG. 67 is an enlarged cross sectional view of a portion surrounded by LXVII in FIG. 66.
Figure 68:
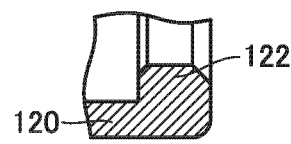
FIG. 68 is an enlarged cross sectional view of a portion surrounded by LXVIII in FIG. 66.

With reference to FIG. 56, a flexible membrane 1120 in a pressure measurement portion according to a seventeenth embodiment is provided with four projections 126 and four recesses 127 unevenly.

The most preferable one among the twelfth to seventeenth embodiments is the twelfth embodiment (triangular type) in consideration of volume variation and retention. Also in the thirteenth embodiment, the variation ratio tends to be the best. An advantage thereof is compactness (shortness) due to the large variation ratio. Moreover, as shown in FIG. 50 or 52, a bilaterally symmetrical cross section facilitates flow of blood and provides a retention prevention effect.

Eighteenth Embodiment

With reference to FIGS. 57 to 60, in a pressure measurement portion 100 for measuring negative pressure according to an eighteenth embodiment, an inlet side joint component 111 has a shape different from that of an outlet side joint component 112. In order to facilitate assembly, inlet side joint component 111 (first joint component) has such a shape that joint component 111 can be inserted into a housing 110 after inserting a rib 122 of a flexible membrane 120 into a groove 111*b* of joint component 111. On the other hand, outlet side joint component 112 (second joint component) is provided with a rib 112*a* for supporting flexible membrane 120. Furthermore, since thick membrane portion 121 of flexible membrane 120 exists, flexible membrane 120 is prevented from being positionally deviated to result in a decreased sealing property.

With reference to FIGS. 61 to 64, housing 110 is provided with a projection 110*a* for engagement with joint component 112. Projection 110*a* is engaged with joint component 112, thus preventing joint component 112 from being separated therefrom. No projection is provided at the side at which inlet side joint component 111 is engaged.

With reference to FIGS. 65 to 68, in flexible membrane 120, a rib 122 is provided in inlet side joint component 111, and a thick membrane portion 121 is provided in outlet side joint component 112. Rib 122 projects toward the inner circumferential side, and thick membrane portion 121 projects toward the outer circumferential side.

Figure 69:
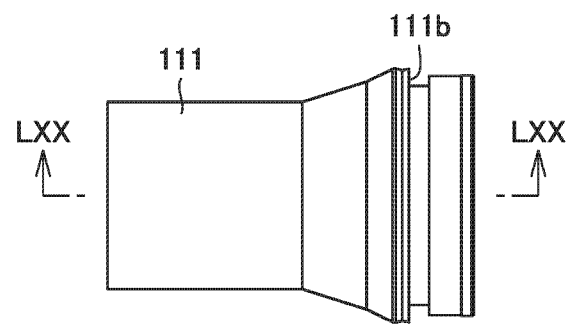
FIG. 69 is a plan view of an inlet side joint component of the pressure measurement portion for measuring negative pressure according to the eighteenth embodiment.
Figure 70:
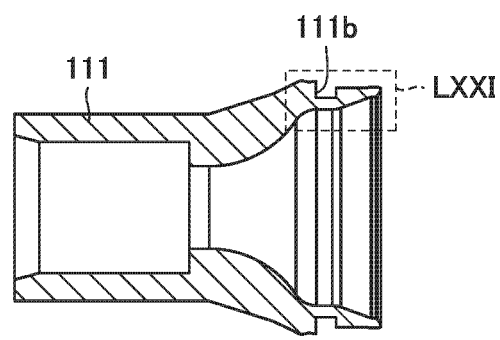
FIG. 70 is a cross sectional view taken along a LXX-LXX line in FIG. 69.
Figure 71:
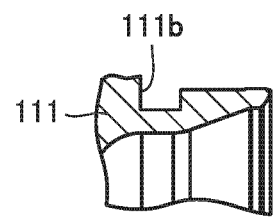
FIG. 71 is an enlarged cross sectional view of a portion surrounded by LXXI in FIG. 70.

With reference to FIGS. 69 to 71, inlet side joint component 111 is provided with an annular groove 111*b* for engagement with rib 122 of flexible membrane 120. Since rib 122 of flexible membrane 120 is engaged with annular groove 111*b*, flexible membrane 120 can be prevented from being detached from joint component 111.

Figure 72:
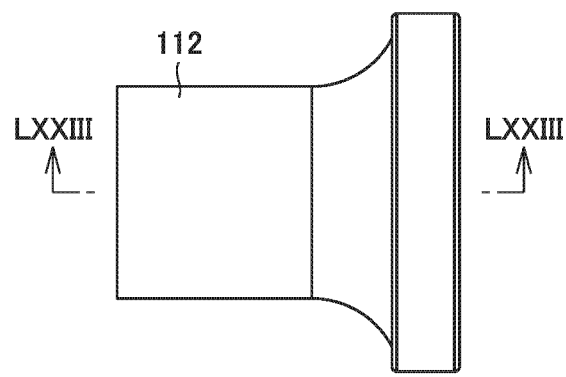
FIG. 72 is a plan view of an outlet side joint component of the pressure measurement portion for measuring negative pressure according to the eighteenth embodiment.
Figure 73:
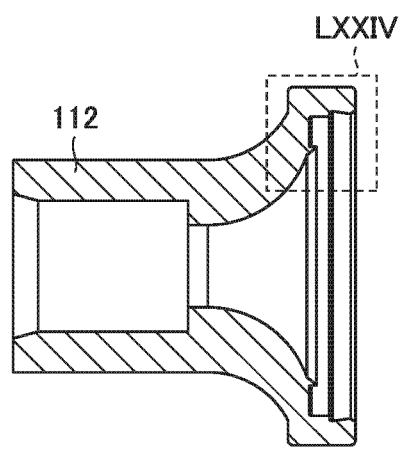
FIG. 73 is a cross sectional view taken along a LXXIII-LXXIII line in FIG. 72.
Figure 74:
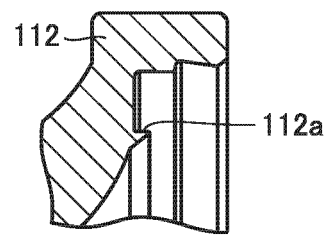
FIG. 74 is an enlarged cross sectional view of a portion surrounded by LXXIV in FIG. 73.

With reference to FIGS. 72 to 74, a rib 112*a* is provided in outlet side joint component 112. Rib 112*a* is provided to have an annular shape and come into abutment with thick membrane portion 121, thus preventing thick membrane portion 121 from falling down to the inner circumferential side.

It should be noted that in the present embodiment, inlet side joint component 111 corresponds to the first joint component and the outlet side joint component corresponds to the second joint component; however, the inlet side joint component may correspond to the second joint component, and the outlet side joint component may correspond to the first joint component.

Nineteenth Embodiment

Figure 75:
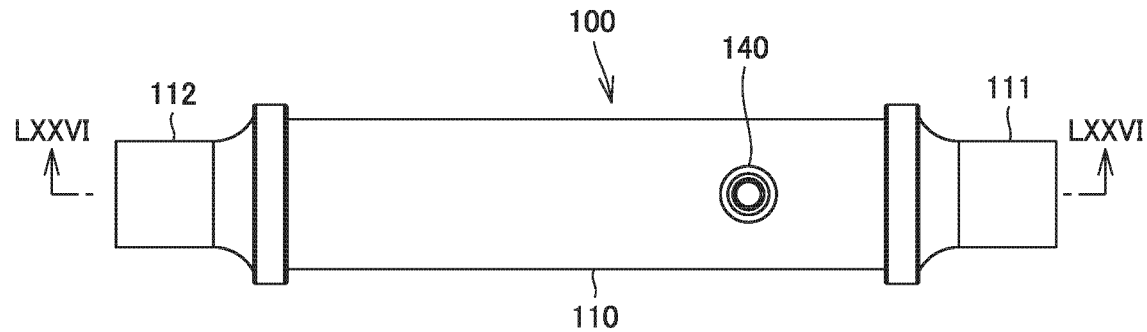
FIG. 75 is a plan view of a pressure measurement portion for measuring negative pressure according to a nineteenth embodiment.
Figure 76:
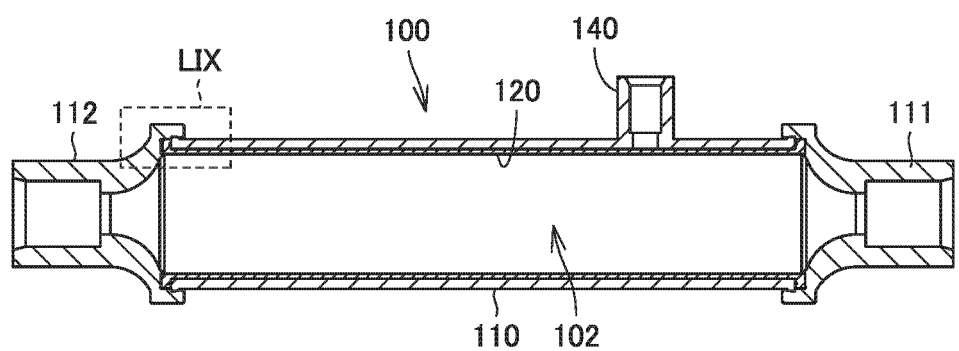
FIG. 76 is a cross sectional view taken along a LXXVI-LXXVI line in FIG. 75.

With reference to FIGS. 75 and 76, in a nineteenth embodiment, each of an inlet side joint component 111 and an outlet side joint component 112 corresponds to the second joint component. In this case, it is difficult to insert a tube into each of the joint components; however, the number of types of joint components can be reduced by employing only the second joint components. It should be noted that each of inlet side joint component 111 and outlet side joint component 112 may correspond to the first joint component.

Twentieth Embodiment

Figure 77:
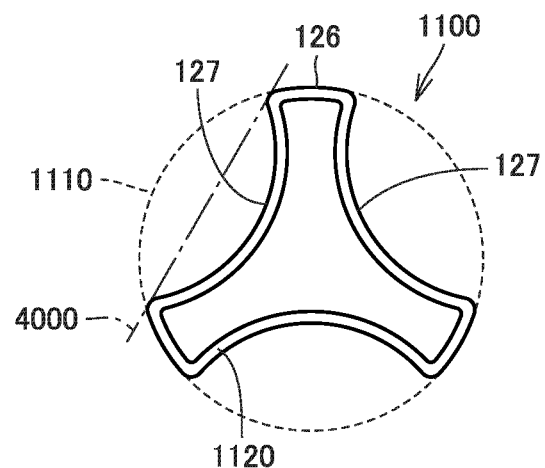
FIG. 77 is a side view of a flexible membrane of a pressure measurement portion for measuring positive pressure according to a twentieth embodiment.

With reference to FIG. 77, in a pressure measurement portion 1100 for measuring positive pressure, the arc of a recess 127 is symmetrical to the arc of a housing 1110 with respect to a straight line 4000. Straight line 4000 connects one end portion of recess 127 to the other end portion of recess 127. Since the arc of recess 127 is symmetrical to the arc of housing 1110 with respect to straight line 4000, flexible membrane 1120 constituting recess 127 can be spread smoothly toward the outer circumferential side.

Figure 78:
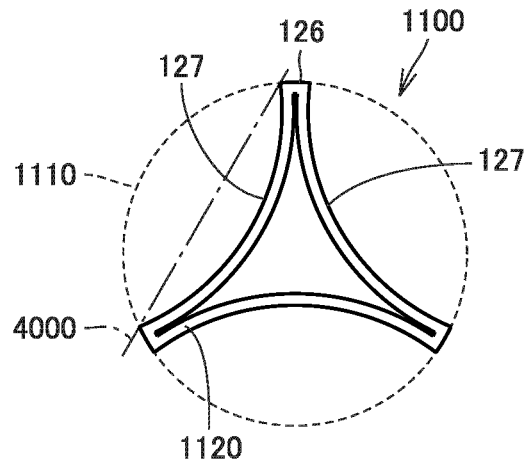
FIG. 78 is a side view of a flexible membrane of a pressure measurement portion for measuring positive pressure according to a modification of the twentieth embodiment.

With reference to FIG. 78, in a pressure measurement portion 1100 for measuring positive pressure, the arc of a recess 127 is asymmetrical to the arc of a housing 1110 with respect to a straight line 4000. Straight line 4000 connects one end portion of recess 127 to the other end portion of recess 127. Since the arc of recess 127 is asymmetrical to the arc of housing 1110 with respect to straight line 4000 and an area at the housing 1110 side relative to straight line 4000 is wide, recess 127 cannot be brought into contact with housing 1110 even if recess 127 is spread toward the housing 1110 side. Moreover, since a blood flow path in flexible membrane 1120 is narrow, blood retention is likely to occur.

Figure 79:
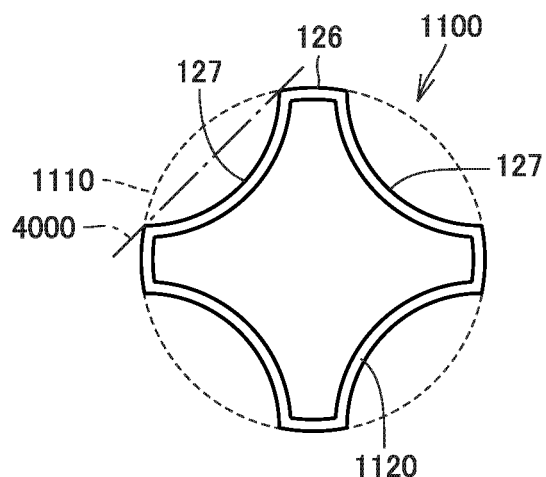
FIG. 79 is a side view of a flexible membrane of a pressure measurement portion for measuring positive pressure according to another modification of the twentieth embodiment.

With reference to FIG. 79, in a pressure measurement portion 1100 for measuring positive pressure, the arc of a recess 127 is symmetrical to the arc of a housing 1110 with respect to a straight line 4000. Straight line 4000 connects one end portion of recess 127 to the other end portion of recess 127. Since the arc of recess 127 is symmetrical to the arc of housing 1110 with respect to straight line 4000, a flexible membrane 1120 constituting recess 127 can be spread smoothly toward the outer circumferential side. The length of the arc of recess 127 to be deformed is short, whereby excessive stress is unlikely to act thereon. However, tube length needs to be long since the volume variation ratio of a blood flow path constituted of flexible membrane 1120 is small. When the width of projection 126 of flexible membrane 1120 is wide as shown in FIGS. 77 and 79, retention of blood is unlikely to occur.

Figure 80:
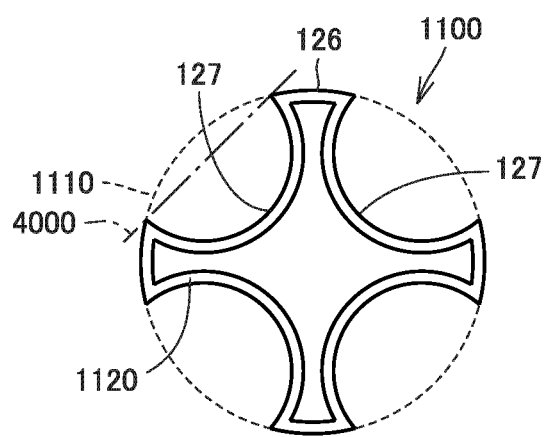
FIG. 80 is a side view of a flexible membrane of a pressure measurement portion for measuring positive pressure according to still another modification of the twentieth embodiment.

With reference to FIG. 80, in a pressure measurement portion 1100 for measuring positive pressure, the arc of a recess 127 is asymmetrical to the arc of a housing 1110 with respect to a straight line 4000. Straight line 4000 connects one end portion of recess 127 to the other end portion of recess 127. Since the arc of recess 127 is asymmetrical to the arc of housing 1110 with respect to straight line 4000 and an area at the housing 1110 side relative to straight line 4000 is narrow, recess 127 is spread toward the housing 1110 side to come into contact with housing 1110. On this occasion, housing 1110 may interfere with flexible membrane 1120 to result in generation of excessive stress.

Since flexible membrane 1120 for measuring positive pressure is shaped to be recessed, flexible membrane 1120 is not elastically deformed up to such a level that affects the measurement until flexible membrane 1120 is brought into contact with housing 1110 as shown in FIGS. 77, 79, and 80. Accordingly, pressure error is unlikely to occur. This allows for precise measurement. The thickness of each of flexible membranes 120, 1120 is suitably not more than 2 mm, more preferably, 1 mm in order not to affect the pressure measurement.

Modification of First to Twentieth Embodiments

A mount may be provided at the lower surface side of the pressure measurement portion for the purpose of stability. The blood circuit may only include a pressure measurement portion for measuring positive pressure or a pressure measurement portion for measuring negative pressure. In assembling the joints, the housing, and the flexible membrane, the joints and the housing may be fixed to each other through engagement therebetween, or may be fixed to each other through bonding therebetween using ultrasonic welding or adhesive agent.

Twenty-First Embodiment

A pressure measurement portion in the present embodiment is suitably provided at extracted blood pressure measurement site 2 illustrated in FIG. 1 and serving as a negative pressure site.

Figure 81:
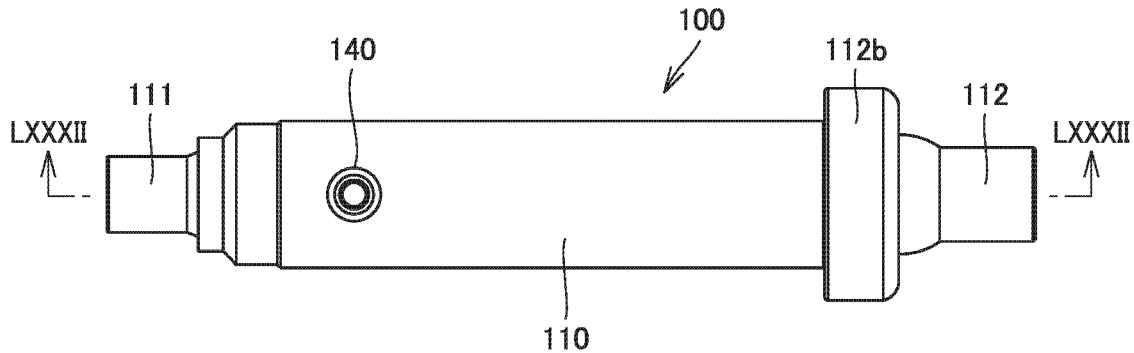
FIG. 81 is a plan view of a pressure measurement portion for measuring negative pressure according to a twenty-first embodiment.
Figure 82:
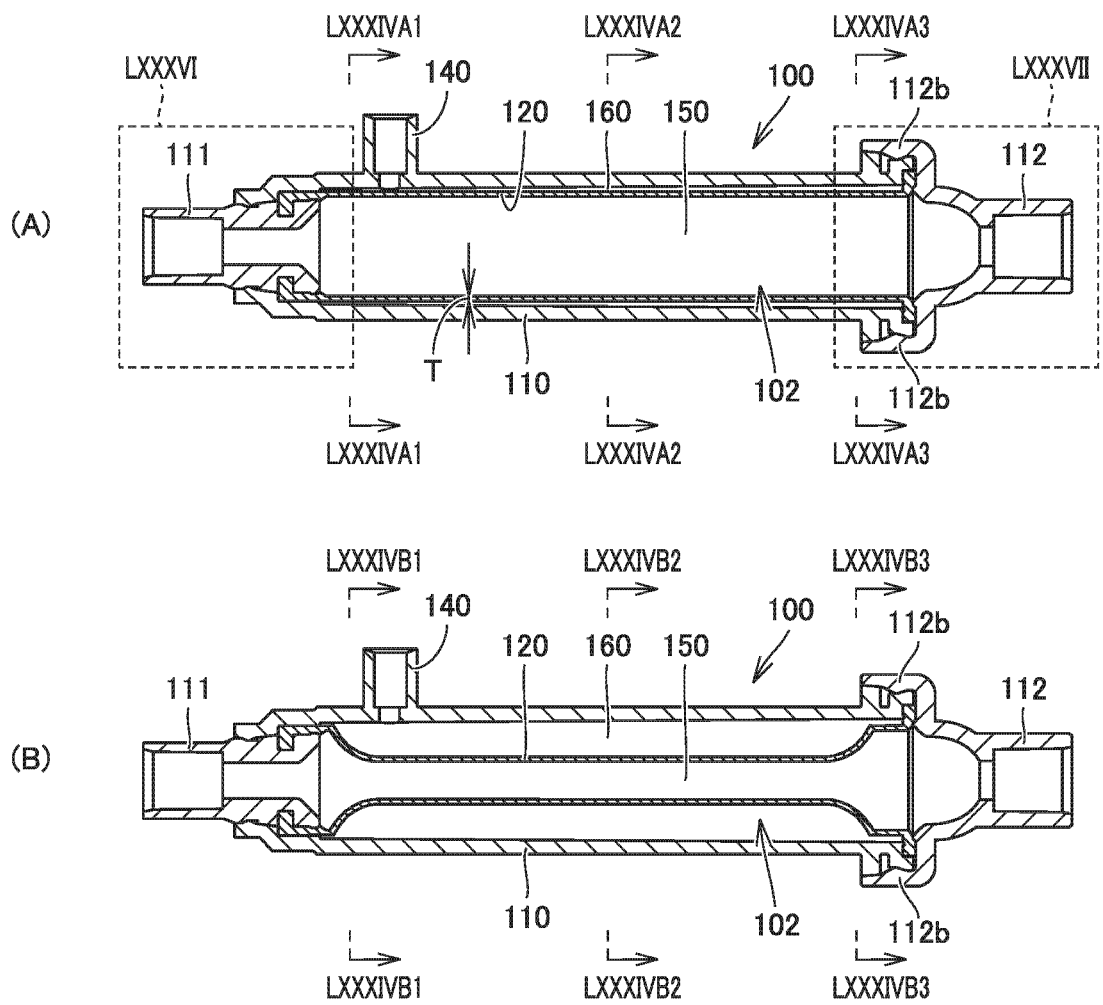
FIG. 82 (A) is a cross sectional view taken along a LXXXII-LXXXII line in FIG. 81 in an initial state, and FIG. 82 (B) is a cross sectional view taken along a LXXXII-LXXXII line in FIG. 81 during measurement of pressure.

As shown in FIG. 81 and FIG. 82, a pressure measurement portion 100 includes a housing 110, a joint component 111 serving as the first joint component, a joint component 112 serving as the second joint component, and a flexible membrane 120. Housing 110 is provided with a pressure measurement port 140. Joint component 111 is attached to one end of housing 110 in the axial direction, i.e., an end portion thereof via which blood is introduced. Joint component 112 is attached to the other end of housing 110 in the axial direction, i.e., an end portion thereof via which blood is discharged.

Also in the present embodiment, as with the first embodiment described above, housing 110 has a substantially cylindrical shape and flexible membrane 120 also has a substantially cylindrical shape. Particularly, flexible membrane 120 has a deformable portion having inner and outer diameters constant in the axial direction, and has a cylindrical shape with a substantially exactly circular cross section. Also, housing 110 at a portion corresponding to the deformable portion of flexible membrane 120 has inner and outer diameters constant in the axial direction, and has a cylindrical shape with a substantially exactly circular cross section.

As shown in FIG. 82, housing 110 is hollow. The hollow space of housing 110 extends from inlet side joint component 111 to outlet side joint component 112. Flexible membrane 120 is disposed in the space within housing 110. Flexible membrane 120 is provided close to housing 110 such that the outer circumferential surface of flexible membrane 120 faces the inner circumferential surface of housing 110.

Here, a distance between the inner circumferential surface of housing 110 and the outer circumferential surface of flexible membrane 120 is in the range of about 0 to 2 mm. Suitably, the distance is in the range of not less than 0.5 mm and not more than 1 mm. In the present embodiment, the distance is 1 mm. Here, since the distance between the inner circumferential surface of housing 110 and the outer circumferential surface of flexible membrane 120 satisfies the above-described range, it is possible to secure a large range in which flexible membrane 120 can be deformed in the tube inward direction.

Flexible membrane 120 has one end portion sandwiched between housing 110 and joint component 111, and has the other end portion sandwiched between housing 110 and joint component 112. Accordingly, flexible membrane 120 divides the inside of housing 110 into a blood chamber 150 and an air chamber 160, and can be deformed in the tube inward direction according to pressure of blood flowing in blood chamber 150.

As shown in FIG. 82 (A) and FIG. 83 (A), flexible membrane 120 has a substantially cylindrical shape as described above in an initial state before permitting blood to flow, and includes: a cylindrical portion 120a that can be deformed when blood flows therein; a rib 122 (see FIG. 86) provided at one end portion thereof; and a thick membrane portion 121 provided at the other end portion thereof. Thick membrane portion 121 has an end surface provided with an annular protrusion 121a protruding along the axial direction of flexible membrane 120. It should be noted that flexible membrane 120 can be formed using various types of materials as described below; however, flexible membrane 120 is suitably formed through injection molding using a resin material. As the resin material, a styrene-based elastomer can be used particularly suitably.

As shown in FIG. 82 (B) and FIG. 83 (B), flexible membrane 120 is deformed in the tube inward direction due to such a pressure difference that the pressure of blood chamber 150 becomes lower than the pressure of air chamber 160 due to a function of blood pump 4 (see FIG. 1) serving as a pumping segment when blood pump 4 operates to cause blood to flow into blood chamber 150, which is an inner space of flexible membrane 120. On this occasion, the shape of cylindrical portion 120*a* is changed to form three depression portions 128 extending in parallel with one another.

These three depression portions 128 are formed substantially equally along the circumferential direction of cylindrical portion 120*a*. Each of these three depression portions 128 is formed to extend along the axial direction of cylindrical portion 120*a*. Here, these three depression portions 128 are spontaneously formed due to a pressure difference between blood chamber 150 and air chamber 160 when a condition derived from a verification test described below is satisfied.

Figure 84:
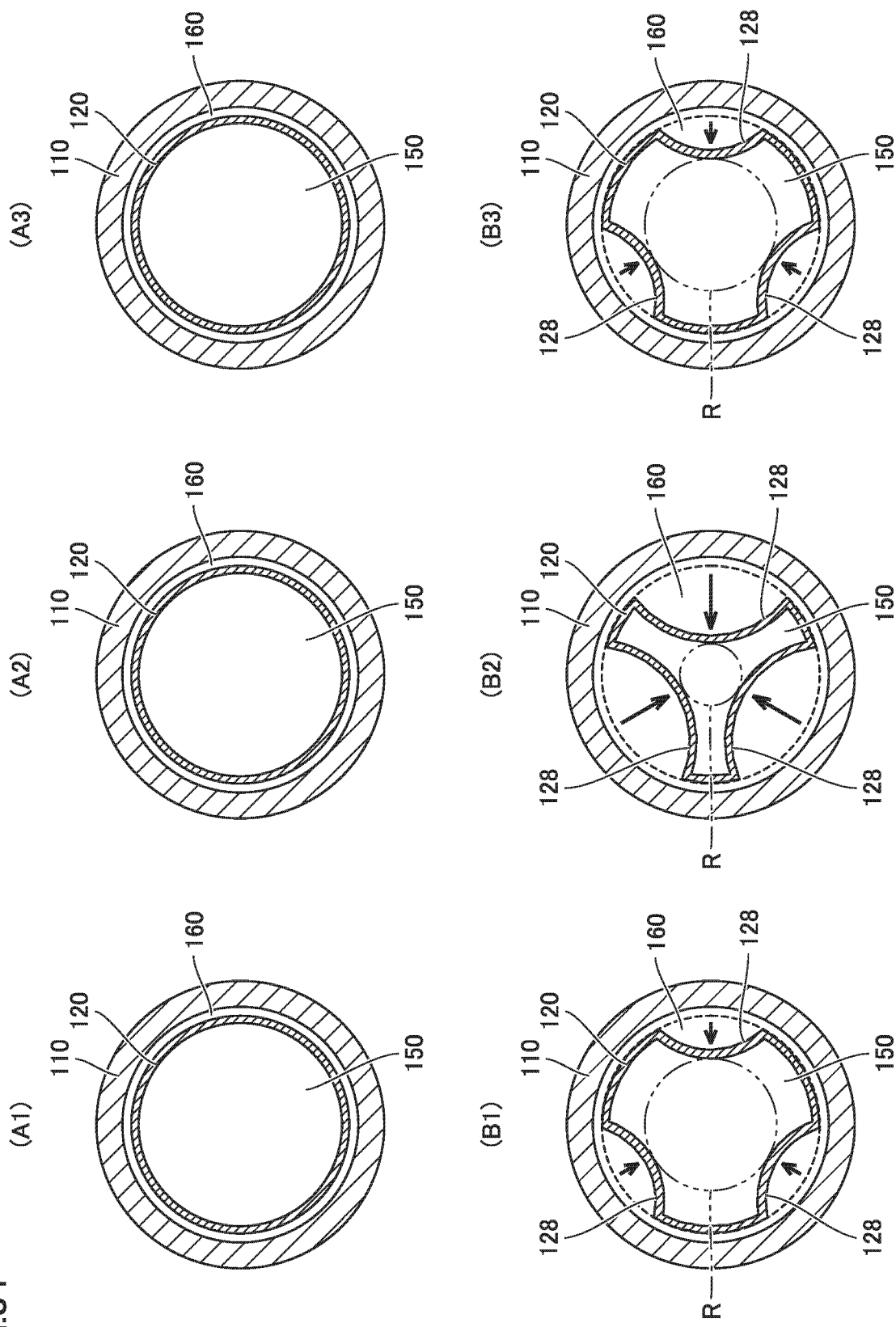
FIGS. 84 (A1) to (A3) are respective cross sectional views taken along a LXXXIVA1-LXXXIVA1 line to a LXXXIVA3-LXXXIVA3 line in FIG. 82 (A), and FIGS. 84 (B1) to (B3) are respective cross sectional views taken along a LXXXIVB1-LXXXIVB1 line to a LXXXIVB3-LXXXIVB3 line in FIG. 82 (B).

Due to three depression portions 128 thus formed, the shape of flexible membrane 120 is changed as shown in FIG. 84. Here, FIGS. 84 (A1) and (B1) show a change in shape in the vicinity of the one end portion of the flexible membrane (i.e., in the vicinity of the blood introduction side) before and after blood flows therein. FIGS. 84 (A2) and (B2) show a change in shape at the central portion of the flexible membrane in the axial direction before and after blood flows therein. FIGS. 84 (A3) and (B3) show a change in shape in the vicinity of the other end portion of the flexible membrane (i.e., in the vicinity of the blood discharging side) before and after blood flows therein.

Flexible membrane 120 having the cylindrical shape in the initial state before permitting blood to flow therein as shown in FIGS. 84 (A1) to (A3) is deformed to be depressed in the tube inward direction (i.e., in an arrow direction shown in the figures) at the three positions in the circumferential direction during measurement of pressure after blood flows therein as shown in FIGS. 84 (B1) to (B3). Accordingly, the volume of blood chamber 150 is decreased and the volume of air chamber 160 is increased. On this occasion, large margin for the deformation of flexible membrane 120 can be secured because flexible membrane 120 is disposed close to the inner circumferential surface of housing 110 in the initial state before permitting blood to flow therein. Accordingly, a large variable volume of blood chamber 150 can be secured.

It should be noted that the deformation of flexible membrane 120 is the maximum at the central portion of flexible membrane 120 in the axial direction, is the minimum at the both end portions of flexible membrane 120, and becomes gradually larger in a direction from each of the end portions of flexible membrane 120 in the axial direction to the central portion of flexible membrane 120. Accordingly, no excessive change occurs in a cross sectional area within flexible membrane 120 along the axial direction, thereby preventing occurrence of retention of blood.

Here, as shown in FIGS. 84 (B1) to (B3), depression portions 128 are formed substantially equally along the circumferential direction of flexible membrane 120. Accordingly, flexible membrane 120 is deformed to have a substantially triangular cross section in which respective sides are recessed. Accordingly, in the central portion in the cross section, a space (portion indicated by a reference character R in the figures) surely remains, whereby flexible membrane 120 can be prevented from being closed and the flow of blood can be secured.

In the verification test, it was checked how deformability and deformed shape of the flexible membrane became different when the size of the flexible membrane was changed variously. Based on this, a condition was derived with which the above-described three depression portions appeared with good reproducibility. In the verification test, as the flexible membrane, there were prepared samples having different ratios between axial length X and outer diameter Y of cylindrical portion 120*a* as shown in FIG. 83 (A). It should be noted that each of the samples is composed of a styrene-based elastomer.

As shown in FIG. 85, it was confirmed that when ratio X/Y is 3.0, the deformability of the flexible membrane becomes low, and when ratio X/Y is not less than 4.0 and not more than 10.0, the deformability of the flexible membrane becomes high. Moreover, it was confirmed that when ratio X/Y is not less than 3.0 and not more than 8.0, the flexible membrane is deformed to have the above-described substantially triangular cross section in which each side is recessed (i.e., shape with three depression portions 128 described above), and when ratio X/Y is not less than 8.0 and not more than 10.0, the flexible membrane is deformed to have a straight line shape, i.e., is deformed to be substantially completely closed.

It should be noted that in the above-described verification test, similar verification was performed with regard to the membrane thickness (i.e., thickness indicated by a reference character T in FIG. 82 (A)) of the flexible membrane and Shore A hardness of the flexible membrane by variously changing the membrane thickness and Shore A hardness, although details thereof are not provided here. As a result, it was confirmed that: three depression portions 128 described above appear with good reproducibility when membrane thickness T satisfies a condition of 0.2 mm≤T≤0.6 mm; and three depression portions 128 described above appear with good reproducibility when the Shore A hardness is not less than 20 and not more than 60.

Based on the above result, it is understood that as shown as a comprehensive evaluation in FIG. 85, three depression portions 128 appear with good reproducibility when ratio X/Y satisfies a condition of 4.0≤X/Y≤8.0. Therefore, when the condition is satisfied, it is understood that a large variable volume of the blood chamber can be secured, occurrence of retention of blood can be prevented, and the flow of blood can be secured.

Figure 86:
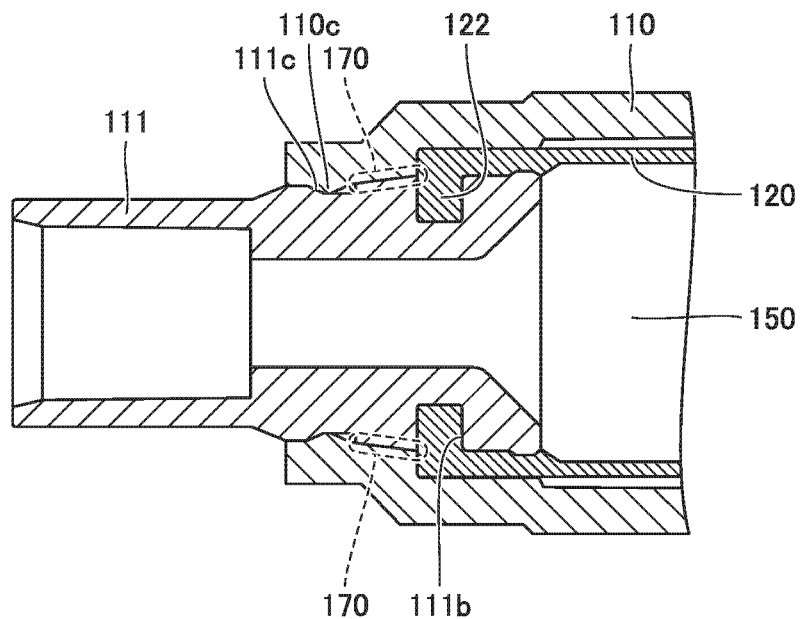
FIG. 86 is an enlarged cross sectional view showing a portion surrounded by LXXXVI in FIG. 82 (A).
Figure 87:
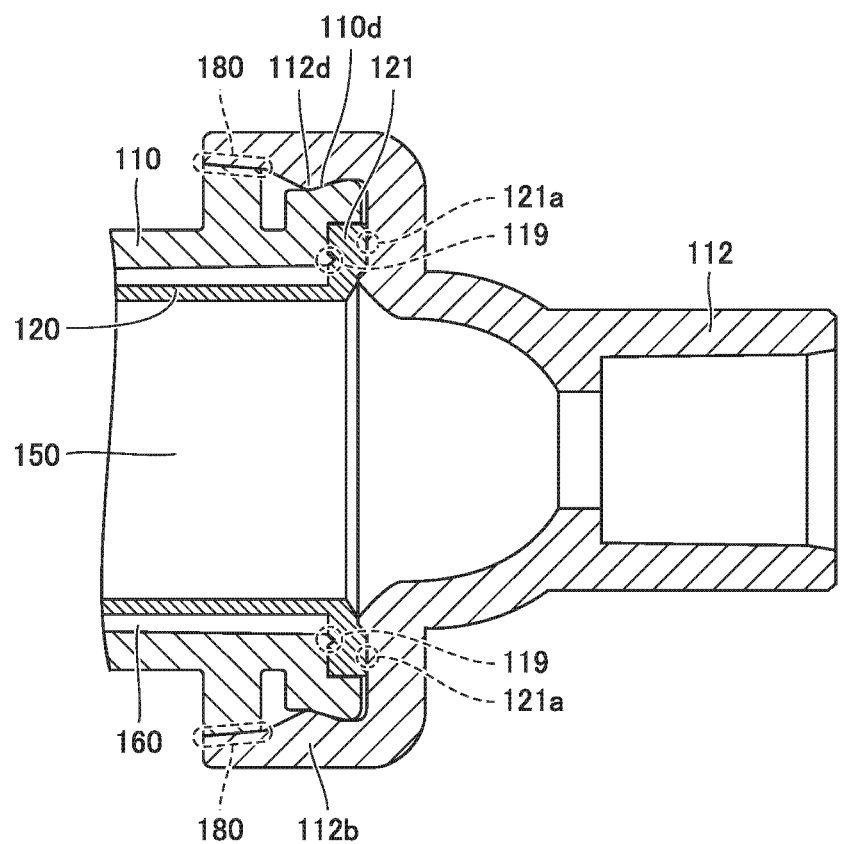
FIG. 87 is an enlarged cross sectional view showing a portion surrounded by LXXXVII in FIG. 82 (A).

As shown in FIG. 86 and FIG. 87, in the pressure measurement portion in the present embodiment, a below-described attachment structure is employed.

As shown in FIG. 86, an annular groove 111*b* is provided at a predetermined position of the outer circumferential surface of inlet side joint component 111 to extend along the circumferential direction, and an annular rib 122 is provided at the one end portion (i.e., end portion at the blood introduction side) of flexible membrane 120 to project in the tube inward direction and extend along the circumferential direction. Rib 122 of flexible membrane 120 is engaged with groove 111*b* of joint component 111.

Here, joint component 111 is engaged with the one end of housing 110 (i.e., end portion at the blood introduction side). Accordingly, the vicinity of the one end portion of flexible membrane 120 is in abutment with the inner circumferential surface of housing 110 and the outer circumferential surface of joint component 111, and is sandwiched between housing 110 and joint component 111.

Moreover, a projection 110c having an annular shape is provided at a predetermined position of the inner circumferential surface of housing 110 to project radially inwardly. A recess 111c having an annular shape is provided at a predetermined position of the outer circumferential surface of inlet side joint component 111. Projection 110c having the annular shape and provided in housing 110 is engaged with recess 111c having the annular shape and provided in joint component 111. Accordingly, housing 110 and joint component 111 are restricted from being relatively moved in the axial direction, thereby preventing detachment thereof.

Further, a rotation prevention mechanism 170 is provided at a portion axially inwardly of a portion at which the engagement portion including projection 110c having the annular shape and recess 111c having the annular shape is located. Rotation prevention mechanism 170 is constituted of knurling including: an irregularity provided at the inner circumferential surface of housing 110; and an irregularity provided at the outer circumferential surface of joint component 111 to be engaged with the foregoing irregularity. In each of these irregularities, recesses and projections extend along the axial direction and are disposed alternately along the circumferential direction, whereby the irregularities are engaged with each other to restrict relative rotation of housing 110 and joint component 111.

Moreover, as shown in FIG. 87, outlet side joint component 112 is provided with a covering portion 112b that overlaps with the outer circumferential surface of the other end of housing 110 (i.e., end portion at the blood discharging side) and that covers the end surface of the other end of housing 110. Thick membrane portion 121 having an annular shape is provided at the other end portion of flexible membrane 120 (i.e., end portion at the blood discharging side) to project radially outwardly and extend along the circumferential direction.

Here, covering portion 112b of joint component 112 is engaged with the other end of housing 110. Accordingly, thick membrane portion 121 of flexible membrane 120 is in abutment with the end surface of the other end of housing 110 and the inner surface of covering portion 112b of joint component 112, and is sandwiched between housing 110 and joint component 112.

Moreover, a projection 110d having an annular shape is provided at a predetermined position of the inner circumferential surface of housing 110 to project radially inwardly. A recess 112d having an annular shape is provided at a predetermined position of the outer circumferential surface of outlet side joint component 112. Projection 110d having the annular shape and provided in housing 110 is engaged with recess 112d having the annular shape and provided in joint component 112. Accordingly, housing 110 and joint component 112 are restricted from being relatively moved in the axial direction, thereby preventing detachment thereof.

Further, a rotation prevention mechanism 180 is provided at a portion axially inwardly of a portion at which the engagement portion including projection 110d having the annular shape and recess 112d having the annular shape is located. Rotation prevention mechanism 180 is constituted of knurling including: an irregularity provided at the inner circumferential surface of housing 110; and an irregularity provided at the outer circumferential surface of joint component 112 to be engaged with the foregoing irregularity. In each of these irregularities, recesses and projections extend along the axial direction and are disposed alternately along the circumferential direction, whereby the irregularities are engaged with each other to restrict relative rotation of housing 110 and joint component 112.

As described above, the one end portion of flexible membrane 120 is fixed by sandwiching the one end portion of flexible membrane 120 between housing 110 and joint component 111 in the radial direction, and the other end portion of flexible membrane 120 is fixed by sandwiching the other end portion of flexible membrane 120 between housing 110 and joint component 112 in the axial direction.

It should be noted that annular protrusion 121a (see FIG. 83) provided in thick membrane portion 121 of flexible membrane 120 is pressed to be collapsed by the inner surface of covering portion 112b of joint component 112. Accordingly, the sealing property of this portion is secured. Moreover, as shown in FIG. 87, rib 119 having the annular shape is provided at the end surface of the other end of housing 110 to project axially outwardly. Rib 119 fits in thick membrane portion 121 of flexible membrane 120, thereby securing the sealing property of this portion.

By employing the attachment structure described above, there is provided an effect of facilitating an assembly operation as describe below.

Figure 88:
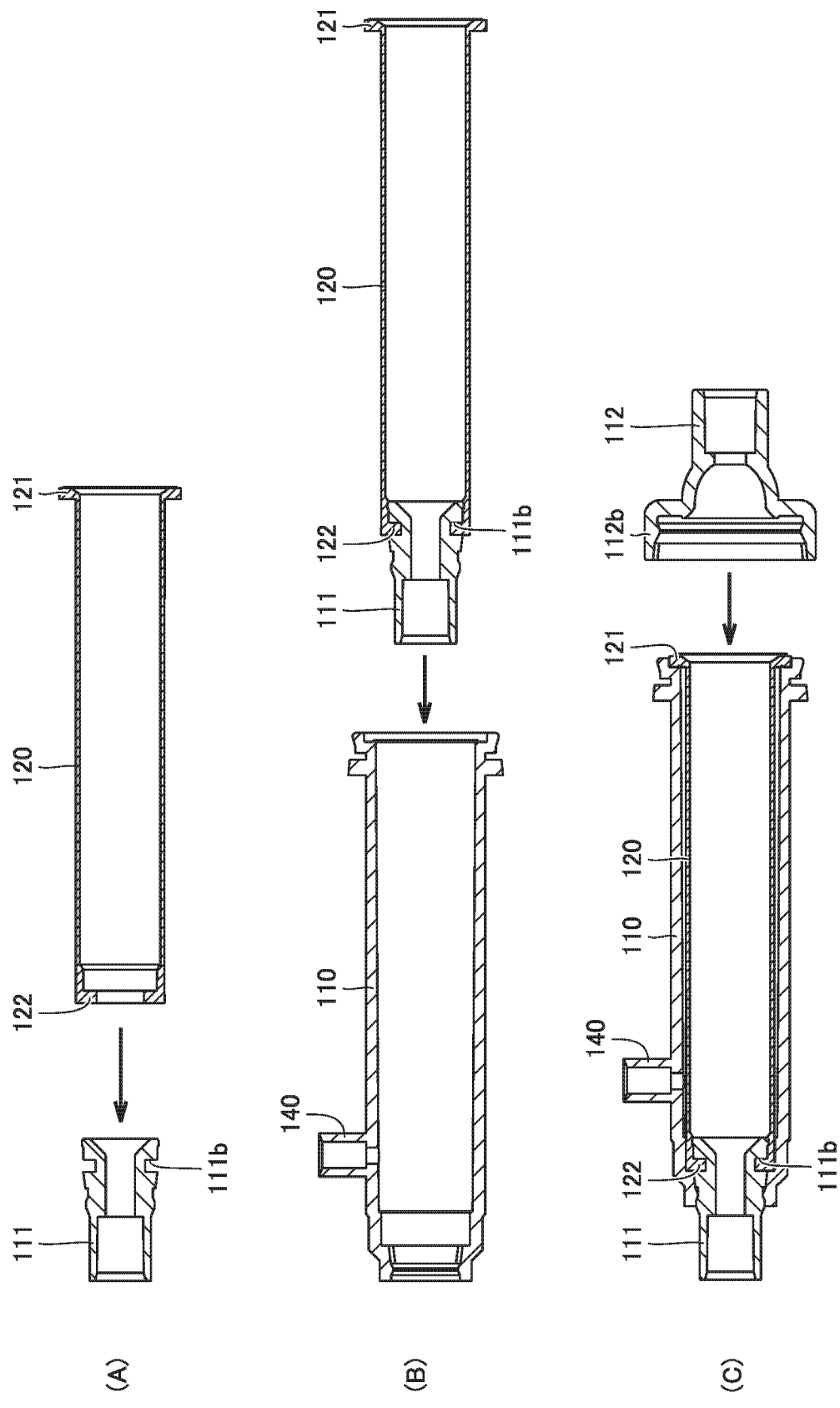
FIGS. 88 (A) to (C) are schematic views for illustrating a method for assembling the pressure measurement portion for measuring negative pressure shown in FIG. 81.

Specifically, first, as shown in FIG. 88 (A), joint component 111 is attached to flexible membrane 120 by engaging rib 122 of flexible membrane 120 with groove 111b of joint component 111, and then they are inserted into housing 110 as shown in FIG. 88 (B). In doing so, flexible membrane 120 and joint component 111 are pressed into the one end of housing 110 from inside the housing.

On this occasion, the irregularities of the knurling serving as rotation prevention mechanism 170 are engaged with each other, and projection 110c having the annular shape is engaged with recess 111c having the annular shape, whereby joint component 111 is fixed to housing 110.

Next, as shown in FIG. 88 (C), joint component 112 is engaged with the other end of housing 110 to sandwich thick membrane portion 121 of flexible membrane 120 between the end surface of the other end of housing 110 and joint component 112.

On this occasion, the irregularities of the knurling serving as rotation prevention mechanism 180 are engaged with each other and projection 110d having the annular shape is engaged with recess 112d having the annular shape, whereby joint component 112 is fixed to housing 110 without positional deviation of flexible membrane 120. In this way, the manufacturing of pressure measurement portion 100 is completed.

By thus employing the attachment structure such as pressure measurement portion 100 in the present embodiment, pressure measurement portion 100 can be manufactured through such a very simple assembly method, thereby reducing the manufacturing cost.

Although it has been described in the present embodiment that rotation prevention mechanism 180 is provided axially inwardly of the engagement portion of housing 110 and joint component 112 as described above, rotation prevention mechanism 180 can be provided axially outwardly of the engagement portion of housing 110 and joint component 112. An exemplary configuration in that case is shown in FIG. 89 and FIG. 90 as a modification.

Figure 89:
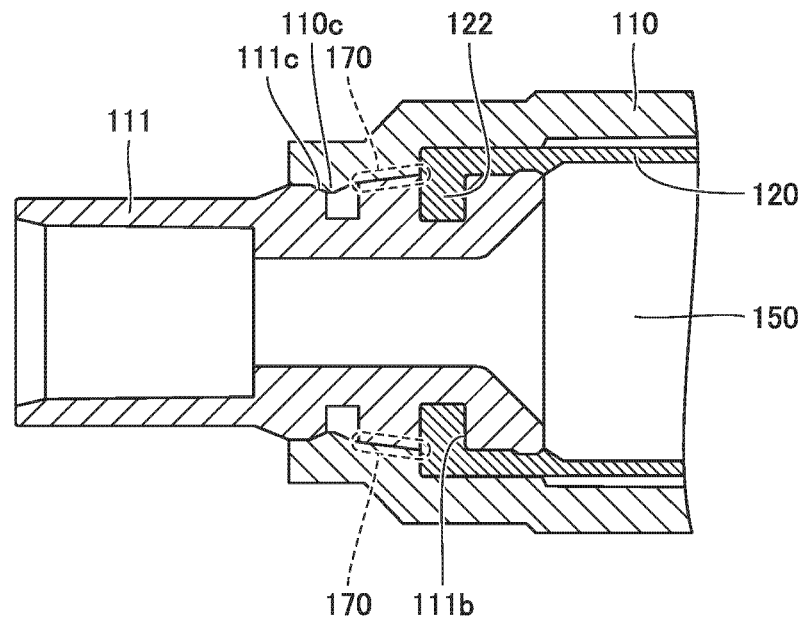
FIG. 89 is a cross sectional view showing an attachment structure at one end side of a pressure measurement portion for measuring negative pressure according to a modification of the twenty-first embodiment.

As shown in FIG. 89, in the present modification, the attachment structure at the one end side of housing 110 is substantially the same as the attachment structure shown in FIG. 86.

Figure 90:
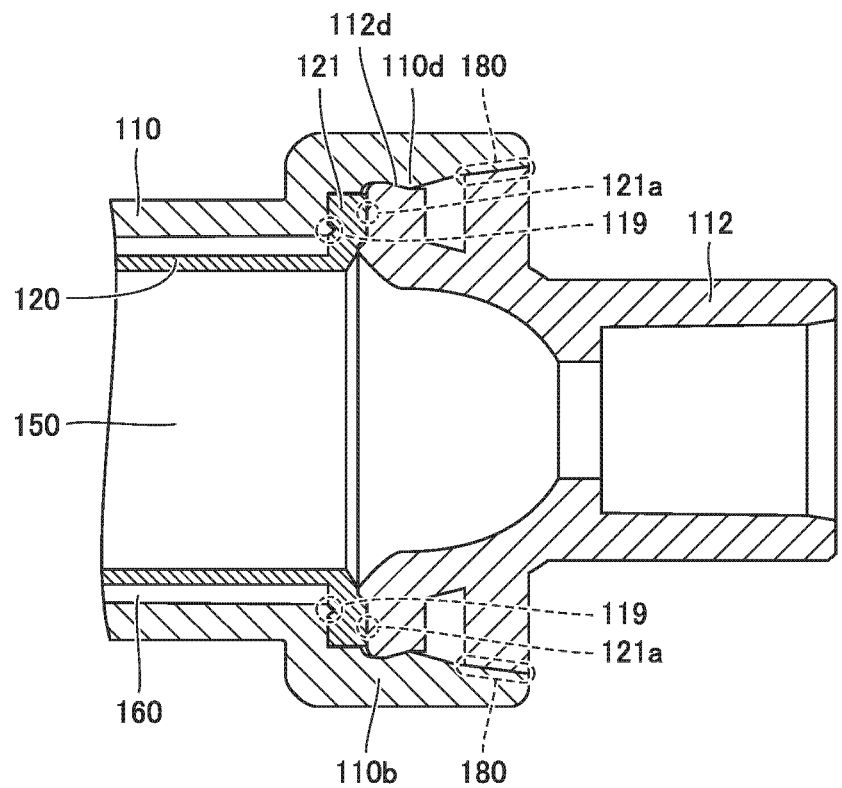
FIG. 90 is a cross sectional view showing an attachment structure at the other end side of the pressure measurement portion for measuring negative pressure according to the modification of the twenty-first embodiment.

On the other hand, as shown in FIG. 90, in the present modification, covering portion 110b is provided at the other end of housing 110 (i.e., end portion at the blood discharging side) to overlap with the outer circumferential surface of outlet side joint component 112 and cover the inlet side end surface of joint component 112. At the other end portion of flexible membrane 120 (i.e., end portion at the blood discharging side), thick membrane portion 121 having an annular shape is provided to project radially outwardly and extend along the circumferential direction.

Here, joint component 112 is engaged with covering portion 110*b* of housing 110. Accordingly, thick membrane portion 121 of flexible membrane 120 is in abutment with the axial end surface of housing 110 located inwardly of covering portion 110*b* and in abutment with the inlet side end surface of joint component 112, and is sandwiched between housing 110 and joint component 112.

Moreover, projection 110*d* having an annular shape is provided at the predetermined position of the inner circumferential surface of covering portion 110*b* of housing 110 to project radially inwardly. Recess 112*d* having the annular shape is provided at the predetermined position of the outer circumferential surface of outlet side joint component 112. Projection 110*d* having the annular shape and provided in housing 110 is engaged with recess 112*d* having the annular shape and provided in joint component 112. Accordingly, housing 110 and joint component 112 are restricted from being relatively moved in the axial direction, thereby preventing detachment thereof.

Further, a rotation prevention mechanism 180 is provided at a portion axially outwardly of a portion at which the engagement portion including projection 110*d* having the annular shape and recess 112*d* having the annular shape is located. Rotation prevention mechanism 180 is constituted of knurling including: an irregularity provided at the inner circumferential surface of housing 110; and an irregularity provided at the outer circumferential surface of joint component 112 to be engaged with the foregoing irregularity. In each of these irregularities, recesses and projections extend along the axial direction and are disposed alternately along the circumferential direction, whereby the irregularities are engaged with each other to restrict relative rotation of housing 110 and joint component 112.

Also when configured in this way, there can be obtained an effect similar to the above-described effect of facilitating the assembly operation.

Twenty-Second Embodiment

A pressure measurement portion in the present embodiment is suitably provided in PD (Pre-dialyzer) pressure measurement site 5 or venous pressure measurement site 11 illustrated in FIG. 1 and serving as a positive pressure site.

Figure 91:
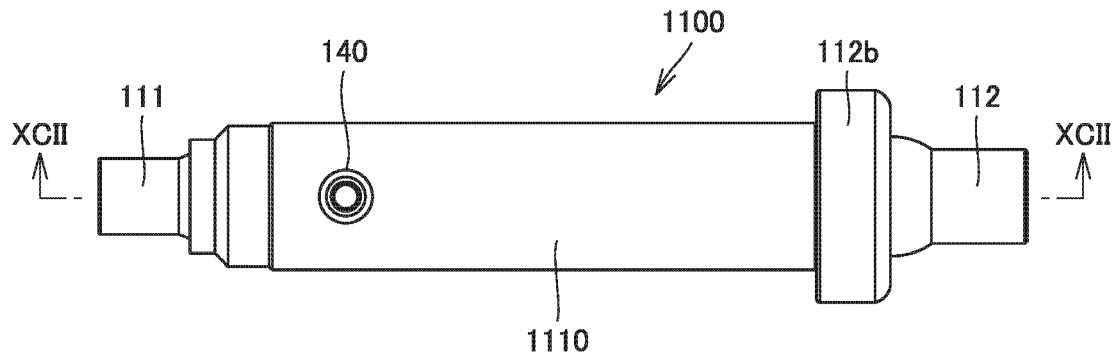
FIG. 91 is a plan view of a pressure measurement portion for measuring positive pressure according to a twenty-second embodiment.
Figure 92:
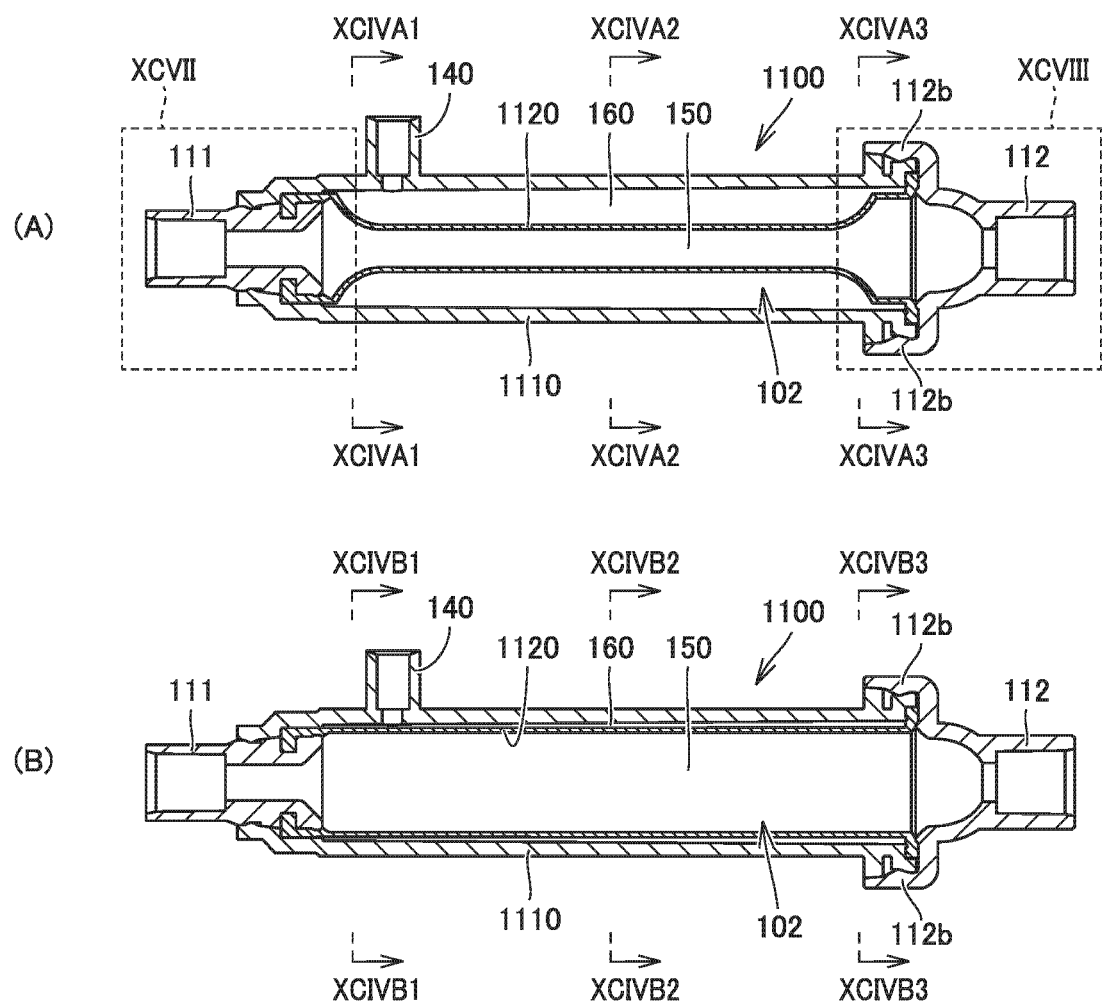
FIG. 92 (A) is a cross sectional view taken along a XCII-XCII line in FIG. 91 in an initial state, and FIG. 92 (B) is a cross sectional view taken along a XCII-XCII line in FIG. 91 during measurement of pressure.

As shown in FIG. 91 and FIG. 92, a pressure measurement portion 1100 includes a housing 1110, a joint component 111 serving as the first joint component, a joint component 112 serving as the second joint component, and a flexible membrane 1120. Housing 1110 is provided with a pressure measurement port 140. Joint component 111 is attached to one end of housing 1110 in the axial direction, i.e., an end portion thereof via which blood is introduced. Joint component 112 is attached to the other end of housing 1110 in the axial direction, i.e., an end portion thereof via which blood is discharged.

Also in the present embodiment, as with the twelfth embodiment above, housing 1110 has a substantially cylindrical shape, and flexible membrane 1120 has a tubular shape with a surface in which three recesses 127 are formed to extend in parallel with one another.

As shown in FIG. 92, housing 1110 is hollow. The hollow space of housing 1110 extends from inlet side joint component 111 to outlet side joint component 112. Flexible membrane 1120 is disposed in the space within housing 1110.

Flexible membrane 1120 has one end portion sandwiched between housing 1110 and joint component 111, and has the other end portion sandwiched between housing 1110 and joint component 112. Accordingly, flexible membrane 1120 divides the inside of housing 1110 into a blood chamber 150 and an air chamber 160, and can be deformed in the tube outward direction according to pressure of blood flowing in blood chamber 150.

As shown in FIG. 92 (A) and FIG. 93 (A), flexible membrane 1120 has a tubular shape with a surface in which three recesses 127 are formed to extend in parallel with one another as described above in an initial state before permitting blood to flow, and includes: a tubular portion 120*b* that can be deformed according to flow of blood; a rib 122 (see FIG. 97) provided at one end portion thereof; and a thick membrane portion 121 provided at the other end portion thereof. Thick membrane portion 121 has an end surface provided with an annular protrusion 121*a* protruding along the axial direction of flexible membrane 1120. It should be noted that flexible membrane 1120 can be formed using various types of materials as described below; however, flexible membrane 120 is suitably formed through injection molding using a resin material. As the resin material, a styrene-based elastomer can be used particularly suitably.

As shown in FIG. 92 (B) and FIG. 93 (B), flexible membrane 1120 is deformed in the tube outward direction due to such a pressure difference that the pressure of blood chamber 150 becomes higher than the pressure of air chamber 160 due to a function of blood pump 4 (see FIG. 1) serving as a pumping segment when blood pump 4 operates to cause blood to flow into a blood chamber 150, which is an inner space of flexible membrane 1120. On this occasion, tubular portion 120*b* is changed in shape to decrease or eliminate three recesses 127 extending in parallel with one another such that tubular portion 120*b* is deformed into a shape closer to a cylindrical shape. It should be noted that for ease of understanding, the following particularly illustrates a case where the shape is changed to eliminate three recesses 127 extending in parallel with one another.

Figure 94:
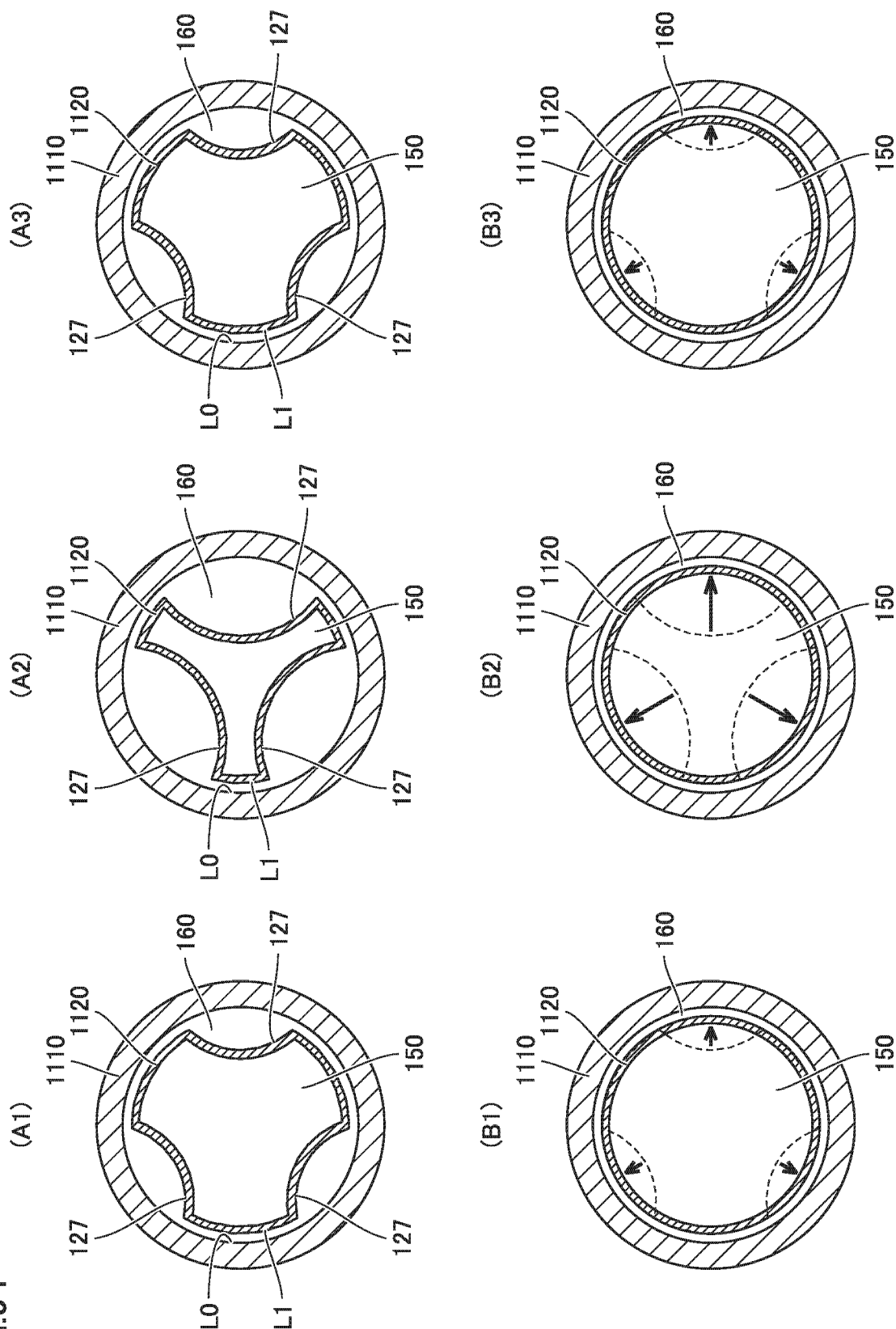
FIGS. 94 (A1) to (A3) are respective cross sectional views taken along a XCIVA1-XCIVA1 line to a XCIVA3-XCIVA3 line in FIG. 92 (A), and FIGS. 94 (B1) to (B3) are respective cross sectional views taken along a XCIVB1-XCIVB1 line to a XCIVB3-XCIVB3 line in FIG. 92 (B).

When three recesses 127 are eliminated, the shape of flexible membrane 1120 is changed as shown in FIG. 92. Here, FIGS. 94 (A1) and (B1) show a change in shape in the vicinity of the one end portion of the flexible membrane (i.e., in the vicinity of the blood introduction side) before and after blood flows therein. FIGS. 94 (A2) and (B2) show a change in shape at the central portion of the flexible membrane in the axial direction before and after blood flows therein. FIGS. 94 (A3) and (B3) show a change in shape in the vicinity of the other end portion of the flexible membrane (i.e., in the vicinity of the blood discharging side) before and after blood flows therein.

As shown in FIGS. 94 (A1) to (A3), before blood flows therein, flexible membrane 1120 has a substantially triangular cross section in which respective sides are recessed. Here, as shown in FIG. 92 (A), FIG. 93 (A), and FIGS. 94 (A1) to (A3), each of cross sectional areas in the tube of flexible membrane 1120 at the both end portions of tubular portion 120*b* of flexible membrane 1120 is larger than the cross sectional area in the tube of flexible membrane 1120 at the central portion of tubular portion 120*b* of flexible membrane 1120. Moreover, the cross sectional area in the tube of flexible membrane 1120 gradually becomes smaller in a direction from each of the end portions to the central portion.

With such a configuration, no excessive change occurs in cross sectional area within flexible membrane 1120 along the axial direction, thereby preventing occurrence of retention of blood.

Flexible membrane 1120 having the tubular shape with three recesses 127 extending in parallel with one another in the initial state before permitting the blood to flow therein as shown in FIGS. 94 (A1) to (A3) is deformed in such a direction that a portion defining these three recesses is expanded in the tube outward direction (i.e., in an arrow direction shown in the figure) during measurement of pressure after blood flows therein as shown in FIGS. 94 (B1) to (B3). Accordingly, the volume of blood chamber 150 is increased and the volume of air chamber 160 is decreased. On this occasion, large margin for the deformation of flexible membrane 1120 can be secured because three recesses 127 are formed in flexible membrane 1120 in the initial state before permitting the blood to flow therein. Accordingly, a large variable volume of blood chamber 150 can be secured.

Here, as shown in FIGS. 94 (A1) to (A3), in an appropriate cross section orthogonal to the axial direction of housing 1110 and including tubular portion 120*b* serving as the deformable portion of flexible membrane 1120, the length (length indicated by a reference character L1 in the figures) of the outer circumferential edge of tubular portion 120*b* of flexible membrane 1120 is equal to or less than the length (length indicated by a reference character L0 in the figures) of the inner circumferential edge of housing 1110 (i.e., L1≤L0).

With such a configuration, the deformation of flexible membrane 1120 can be prevented from being blocked by flexible membrane 1120 itself and housing 1110. Hence, flexible membrane 1120 is smoothly deformed into the substantially cylindrical shape, with the result that retention of blood can be prevented. In other words, if length L1 of the outer circumferential edge of tubular portion 120*b* and length L0 of the inner circumferential edge of housing 1110 satisfy a condition of L1>L0, an excessively expanded portion is formed in flexible membrane 1120 during the pressure measurement to interfere with other portions of flexible membrane 1120 and housing 1110. Accordingly, the shape of flexible membrane 1120 is distorted to increase blood flow resistance, thus resulting in retention of blood.

In order to secure the variable volume of blood chamber 150 while preventing the deformation of flexible membrane 1120 from being thus blocked by flexible membrane 1120 itself and housing 1110, it is preferable that the number of recesses 127 formed in flexible membrane 1120 in the initial state and extending in parallel with one another is 2 to 4.

Figure 95:
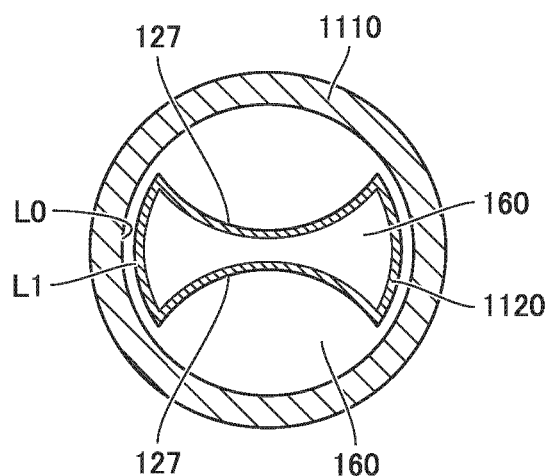
FIG. 95 is a cross sectional view of a pressure measurement portion for measuring positive pressure according to a first modification of the twenty-second embodiment.
Figure 96:
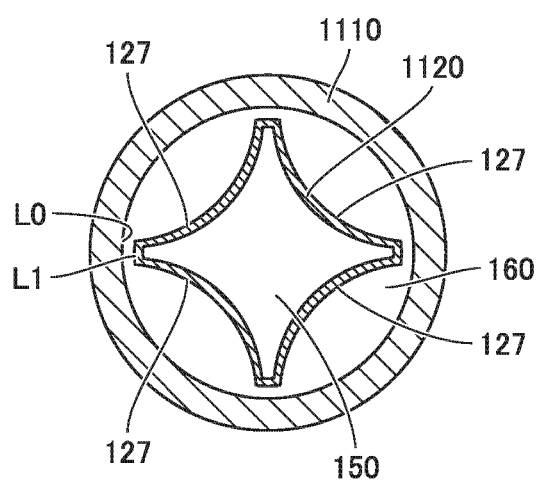
FIG. 96 is a cross sectional view of a pressure measurement portion for measuring positive pressure according to a second modification of the twenty-second embodiment.

A first modification shown in FIG. 95 shows a case where the number of recesses 127 is 2. A second modification shown in FIG. 96 shows a case where the number of recesses 127 is 4. Also in the case of these first and second modifications, when the condition of L1≤L0 is satisfied, retention of blood can be prevented while securing the variable volume of blood chamber 150.

It should be noted that when the number of recesses 127 formed in flexible membrane 1120 in the initial state and extending in parallel with one another is 5 or more, it becomes difficult to sufficiently secure the variable volume of blood chamber 150 while satisfying the condition of L1≤L0. Accordingly, it becomes difficult to sufficiently prevent retention of blood.

With reference to FIGS. 94 (A) to (C), FIG. 95, and FIG. 96, flexible membrane 1120 in the initial state is configured to have an inner circumferential surface not contacted at any portion. Specifically, when forming recesses 127 extending in parallel with one another in flexible membrane 1120 having the tubular shape, it is possible to configure such that a portion of the inner circumferential surface of flexible membrane 1120 is in contact with a different portion of the inner circumferential surface; however, such a configuration is not preferable. This is due to the following reason: if the inner circumferential surface of flexible membrane 1120 is in contact with itself at a certain portion, retention of blood may occur at that portion.

Therefore, a distance of a space at the portion located between recesses 127 formed in flexible membrane 1120 and extending in parallel with one another is preferably secured to be about 0.5 to 2.0 mm. In the present embodiment, the distance is secured to be 1.0 mm.

Figure 97:
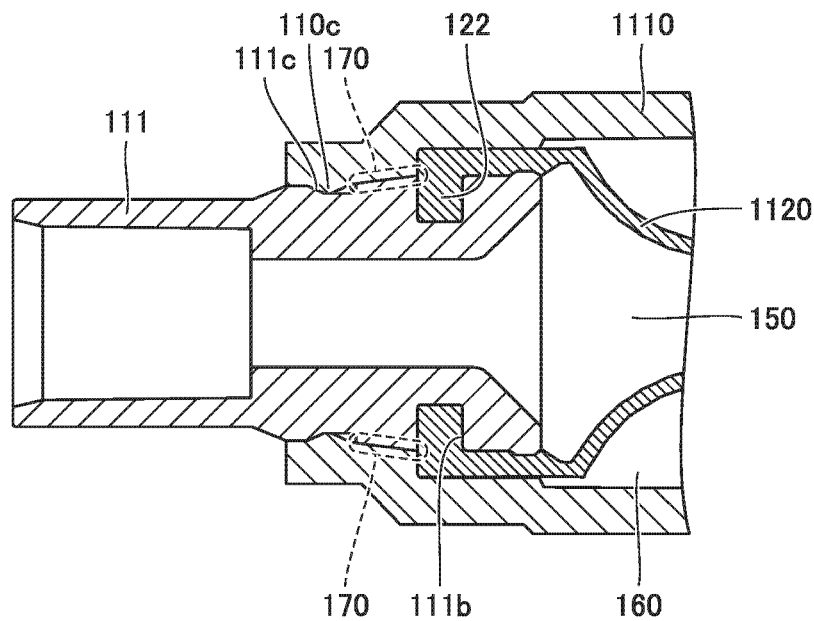
FIG. 97 is an enlarged cross sectional view showing a portion surrounded by XCVII in FIG. 92 (A).
Figure 98:
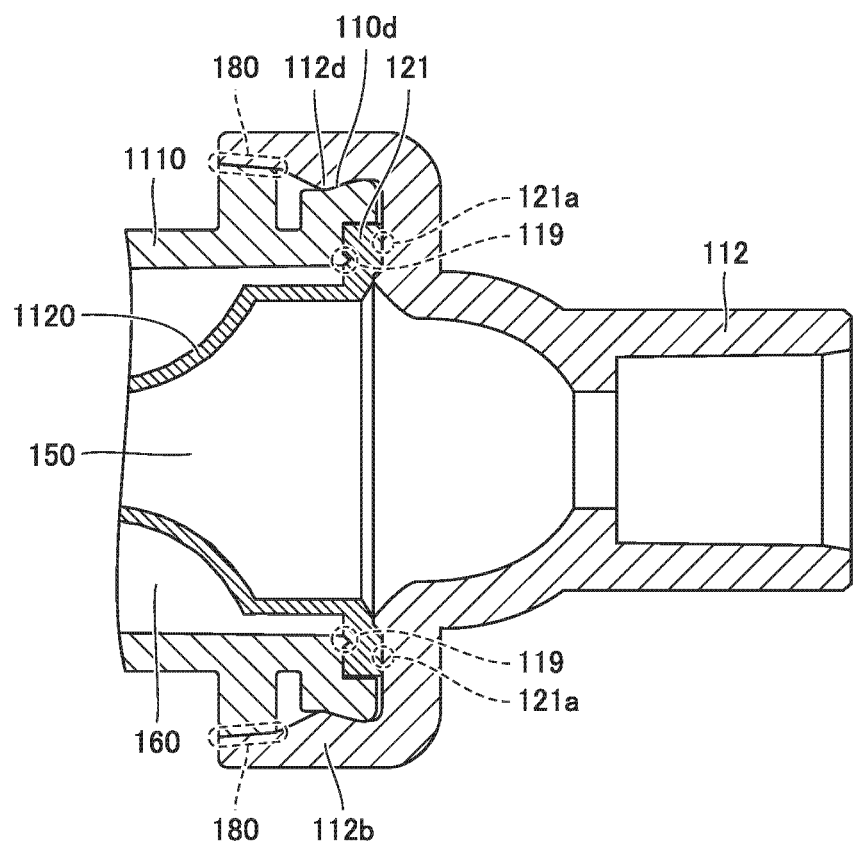
FIG. 98 is an enlarged cross sectional view showing a portion surrounded by XCIVII in FIG. 92 (A).

As shown in FIG. 97 and FIG. 98, in the pressure measurement portion in the present embodiment, an attachment structure described below is employed.

As shown in FIG. 97, an annular groove 111*b* is provided at a predetermined position of the outer circumferential surface of inlet side joint component 111 to extend along the circumferential direction, and an annular rib 122 is provided at the one end portion (i.e., end portion at the blood introduction side) of flexible membrane 1120 to project radially inwardly and extend along the circumferential direction. Rib 122 of flexible membrane 1120 is engaged with groove 111*b* of joint component 111.

Here, joint component 111 is engaged with the one end of housing 1110 (i.e., the end portion at the blood introduction side). Accordingly, the vicinity of the one end portion of flexible membrane 1120 is in abutment with the inner circumferential surface of housing 1110 and the outer circumferential surface of joint component 111, and is sandwiched between housing 1110 and joint component 111.

Moreover, a projection 110*c* having an annular shape is provided at a predetermined position of the inner circumferential surface of housing 1110 to project radially inwardly. A recess 111*c* having an annular shape is provided at a predetermined position of the outer circumferential surface of inlet side joint component 111. Projection 110*c* having the annular shape and provided in housing 1110 is engaged with recess 111*c* having an annular shape and provided in joint component 111. Accordingly, housing 1110 and joint component 111 are restricted from being relatively moved in the axial direction, thereby preventing detachment thereof.

Further, a rotation prevention mechanism 170 is provided at a portion axially inwardly of a portion at which the engagement portion including projection 110*c* having the annular shape and recess 111*c* having the annular shape is located. Rotation prevention mechanism 170 is constituted of knurling including: an irregularity provided at the inner circumferential surface of housing 1110; and an irregularity provided at the outer circumferential surface of joint component 111 to be engaged with the foregoing irregularity. In each of these irregularities, recesses and projections extend along the axial direction and are disposed alternately along the circumferential direction, whereby the irregularities are engaged with each other to restrict relative rotation of housing 1110 and joint component 111.

Moreover, as shown in FIG. 98, outlet side joint component 112 is provided with a covering portion 112*b* that overlaps with the outer circumferential surface of the other end of housing 1110 (i.e., end portion at the blood discharging side) and that covers the end surface of the other end of housing 1110. A thick membrane portion 121 having an annular shape is provided at the other end portion of flexible membrane 1120 (i.e., end portion at the blood discharging side) to project radially outwardly and extend along the circumferential direction.

Here, covering portion 112*b* of joint component 112 is engaged with the other end of housing 1110. Accordingly, thick membrane portion 121 of flexible membrane 1120 is in abutment with the end surface of the other end of housing 1110 and the inner surface of covering portion 112*b* of joint component 112, and is sandwiched between housing 1110 and joint component 112.

Moreover, a projection 110*d* having an annular shape is provided at a predetermined position of the inner circumferential surface of housing 1110 to project radially inwardly. A recess 112*d* having an annular shape is provided at a predetermined position of the outer circumferential surface of outlet side joint component 112. Projection 110*d* having the annular shape and provided in housing 1110 is engaged with recess 112*d* having the annular shape and provided in joint component 112. Accordingly, housing 1110 and joint component 112 are restricted from being relatively moved in the axial direction, thereby preventing detachment thereof.

Further, a rotation prevention mechanism 180 is provided at a portion axially inwardly of a portion at which the engagement portion including projection 110*d* having the annular shape and recess 112*d* having the annular shape is located. Rotation prevention mechanism 180 is constituted of knurling including: an irregularity provided at the inner circumferential surface of housing 1110; and an irregularity provided at the outer circumferential surface of joint component 112 to be engaged with the foregoing irregularity. In each of these irregularities, recesses and projections extend along the axial direction and are disposed alternately along the circumferential direction, whereby the irregularities are engaged with each other to restrict relative rotation of housing 1110 and joint component 112.

As described above, the one end portion of flexible membrane 1120 is fixed by sandwiching the one end portion of flexible membrane 1120 between housing 1110 and joint component 111 in the radial direction, and the other end portion of flexible membrane 1120 is fixed by sandwiching the other end portion of flexible membrane 1120 between housing 1110 and joint component 112 in the axial direction.

It should be noted that annular protrusion 121*a* (see FIG. 93) provided in thick membrane portion 121 of flexible membrane 1120 is pressed to be collapsed by the inner surface of covering portion 112*b* of joint component 112. Accordingly, the sealing property of this portion is secured. Moreover, as shown in FIG. 98, a rib 119 having the annular shape is provided at the end surface of the other end of housing 1110 to project axially outwardly. Rib 119 fits in thick membrane portion 121 of flexible membrane 1120, thereby securing the sealing property of this portion.

By employing the attachment structure described above, there is provided an effect of facilitating an assembly operation as describe below.

Figure 99:
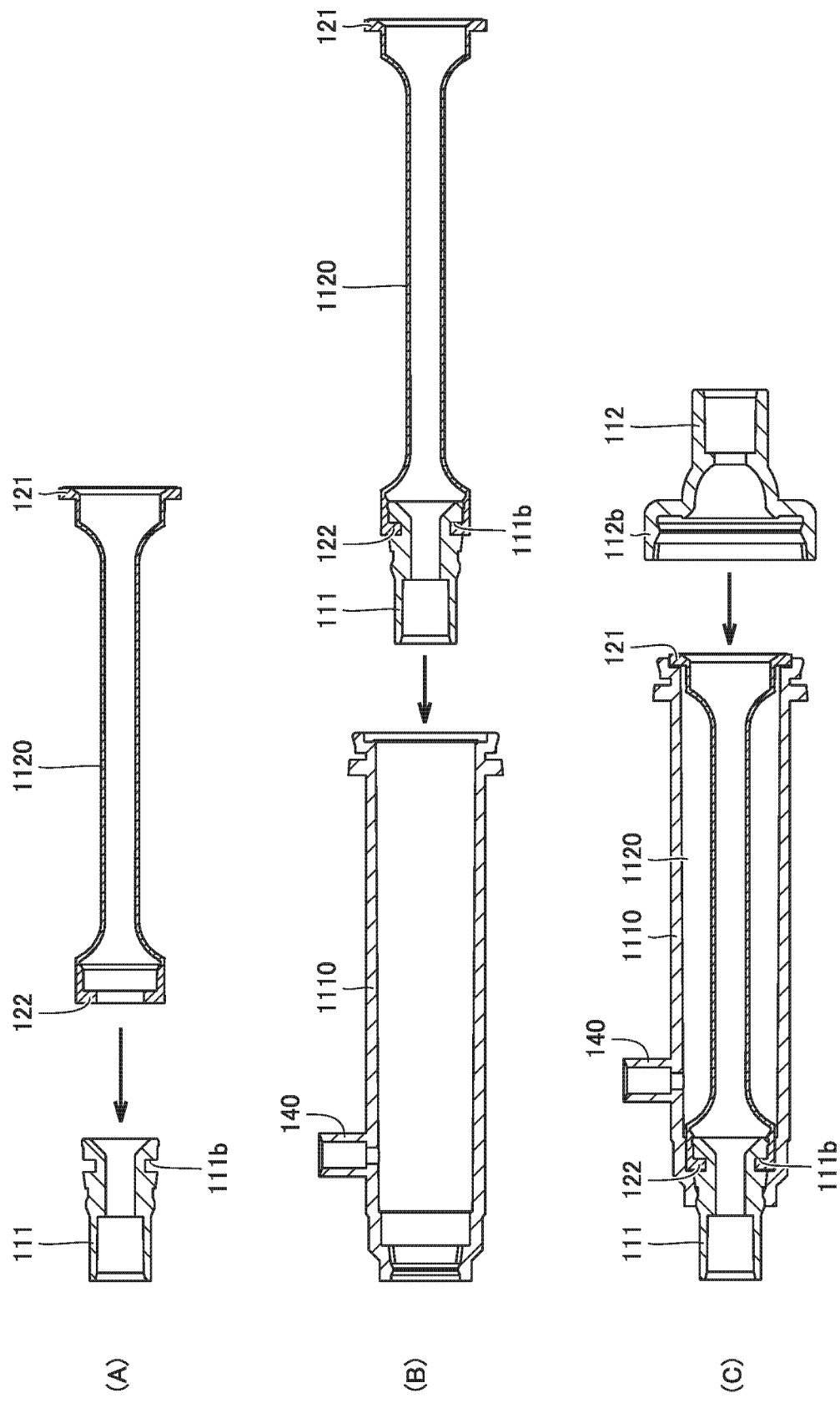
FIGS. 99 (A) to (C) are schematic views for illustrating a method for assembling the pressure measurement portion for measuring positive pressure shown in FIG. 92.

Specifically, first, as shown in FIG. 99 (A), joint component 111 is attached to flexible membrane 1120 by engaging rib 122 of flexible membrane 1120 with groove 111*b* of joint component 111, and then they are inserted into housing 1110 as shown in FIG. 99 (B). In doing so, flexible membrane 1120 and joint component 111 are pressed into the one end of housing 1110 from inside the housing.

On this occasion, the irregularities of the knurling serving as rotation prevention mechanism 170 are engaged with each other, and projection 110*c* having the annular shape is engaged with recess 111*c* having the annular shape, whereby joint component 111 is fixed to housing 1110.

Next, as shown in FIG. 99 (C), joint component 112 is engaged with the other end of housing 1110 to sandwich thick membrane portion 121 of flexible membrane 1120 between the end surface of the other end of housing 1110 and joint component 112.

On this occasion, the irregularities of the knurling serving as rotation prevention mechanism 180 are engaged with each other and projection 110*d* having the annular shape is engaged with recess 112*d* having the annular shape, whereby joint component 112 is fixed to housing 1110 without positional deviation of flexible membrane 1120. In this way, the manufacturing of pressure measurement portion 1100 is completed.

By thus employing the attachment structure such as pressure measurement portion 1100 in the present embodiment, pressure measurement portion 1100 can be manufactured through such a very simple assembly method, thereby reducing the manufacturing cost.

Although it has been described in the present embodiment that rotation prevention mechanism 180 is provided axially inwardly of the engagement portion of housing 1110 and joint component 112 as described above, rotation prevention mechanism 180 can be provided axially outwardly of the engagement portion of housing 1110 and joint component 112. An exemplary configuration in that case is shown in FIG. 100 and FIG. 101 as a modification.

Figure 100:
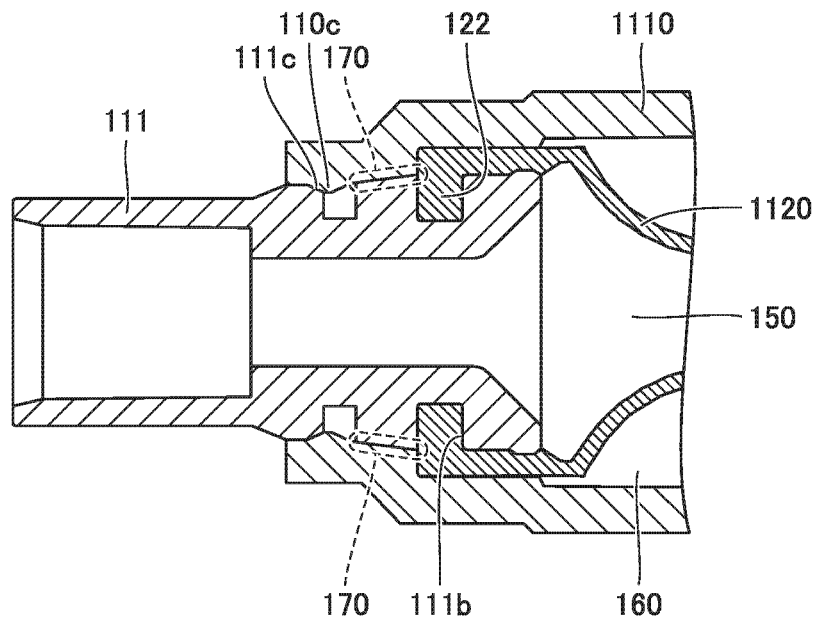
FIG. 100 is a cross sectional view showing an attachment structure at one end side of a pressure measurement portion for measuring positive pressure according to a modification of the twenty-second embodiment.

As shown in FIG. 100, in the present modification, the attachment structure at the one end side of housing 1110 is substantially the same as the attachment structure shown in FIG. 97.

Figure 101:
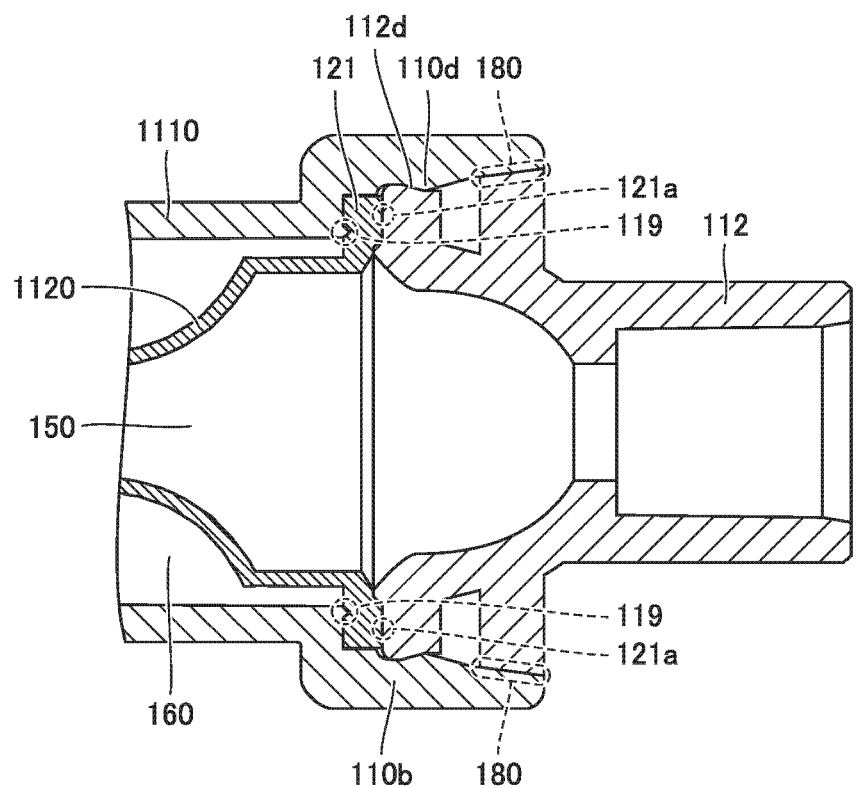
FIG. 101 is a cross sectional view showing an attachment structure at the other end side of the pressure measurement portion for measuring positive pressure according to the modification of the twenty-second embodiment.

On the other hand, as shown in FIG. 101, in the present modification, a covering portion 110*b* is provided at the other end of housing 1110 (i.e., end portion at the blood discharging side) to overlap with the outer circumferential surface of outlet side joint component 112 and cover the inlet side end surface of joint component 112. At the other end portion of flexible membrane 120 (i.e., the end portion at the blood discharging side), thick membrane portion 121 having an annular shape is provided to project radially outwardly and extend along the circumferential direction.

Here, joint component 112 is engaged with covering portion 110*b* of housing 1110. Accordingly, thick membrane portion 121 of flexible membrane 120 is in abutment with the axial end surface of housing 1110 located inwardly of covering portion 110*b* and in abutment with the inlet side end surface of joint component 112, and is sandwiched between housing 1110 and joint component 112.

Moreover, a projection 110*d* having an annular shape is provided at a predetermined position of the inner circumferential surface of covering portion 110*b* of housing 1110 to project radially inwardly. A recess 112*d* having an annular shape is provided at a predetermined position of the outer circumferential surface of outlet side joint component 112. Projection 110*d* having the annular shape and provided in housing 1110 is engaged with recess 112*d* having the annular shape and provided in joint component 112. Accordingly, housing 1110 and joint component 112 are restricted from being relatively moved in the axial direction, thereby preventing detachment thereof.

Further, a rotation prevention mechanism 180 is provided at a portion axially outwardly of a portion at which the engagement portion including projection 110*d* having the annular shape and recess 112*d* having the annular shape is located. Rotation prevention mechanism 180 is constituted of knurling including: an irregularity provided at the inner circumferential surface of housing 1110; and an irregularity provided at the outer circumferential surface of joint component 112 to be engaged with the foregoing irregularity. In each of these irregularities, recesses and projections extend along the axial direction and are disposed alternately along the circumferential direction, whereby the irregularities are engaged with each other to restrict relative rotation of housing 1110 and joint component 112.

Also when configured in this way, there can be obtained an effect similar to the above-described effect of facilitating the assembly operation.

It should be noted that in the above-described embodiments, pressure measurement portion 100 for measuring negative pressure and pressure measurement portion 1100 for measuring positive pressure have been illustrated individually; however, pressure measurement portions 100, 1100 in the present application may be provided in one blood circuit. In that case, the blood circuit includes both: pressure measurement portion 1100 (the eleventh to seventeenth, twentieth, and twenty-second embodiments) serving as the first measurement portion provided downstream of the pumping segment for applying pressure to blood; and pressure measurement portion 100 (the first to tenth, eighteenth, nineteenth, and twenty-first embodiments) serving as the second measurement portion provided upstream of the pumping segment. When blood does not flow in the initial state before permitting the blood to flow, the space between flexible membrane 1120 and housing 1110 is larger than the space between flexible membrane 120 and housing 110.

Each of flexible membranes 120, 1120 preferably has a Shore A hardness of not more than 80. Examples of the material thereof include, but not particularly limited to, various rubber materials such as a natural rubber, a butyl rubber, an isoprene rubber, a butadiene rubber, a styrene-butadiene rubber, and a silicone rubber, as well as various types of resins such as: various types of thermoplastic elastomers such as a polyurethane-based elastomer, a polyester-based elastomer, a polyamide-based elastomer, an olefin-based elastomer, and a styrene-based elastomer; polyvinyl chloride; polyolefin such as polyethylene, polypropylene, ethylene-propylene copolymer, ethylene-vinylacetate copolymer, and crosslinked ethylene-vinylacetate copolymer; polyester such as polyethylene terephthalate; polyurethane; and polyamide. These may be used solely or in combination appropriately. A molding method is not particularly limited and an appropriate method is used such as injection molding, extrusion molding, compression molding, or transfer molding. In the case of the extrusion molding, the manufacturing is facilitated by using the silicone rubber. In the case of the injection molding, the manufacturing is facilitated by using the styrene-based elastomer.

The negative pressure tube (flexible membrane 120) is a tube to be deformed in the tube inward direction unlike the positive pressure tube (flexible membrane 1120). In comparison between the deformation in the tube outward direction and the deformation in the tube inward direction, elastic force is less likely to be generated in the case of the deformation in the tube inward direction. Hence, even when the negative pressure tube has a cylindrical shape having a circular cross section, measurement can be performed with precision.

Regarding the negative pressure tube, the negative pressure tube according to each of the embodiments has a circular cross sectional shape. In the case of the present embodiment, only negative pressure is measured using the negative pressure tube. Since the conventional tube is employed for measurement of negative pressure and positive pressure, the conventional tube needs to expand in the tube outward direction during measurement of positive pressure. If the diameter of the conventional tube is small, the conventional tube cannot be sufficiently expanded. Accordingly, the diameter becomes large, disadvantageously. In contrast, the negative pressure tube according to each of the embodiments can be reduced in size. At various positions, turbulent flow of fluid can be prevented, interference of the fluid can be suppressed, and pressure loss can be reduced.

In addition to the size reduction, the pressure measurement portion for measuring negative pressure according to each of the embodiments has the following effects more excellent than those of Patent Document 1.

First, since there is no large space between the housing and the membrane, a negative pressure measurement range is large.

Second, the pressure measurement portion according to each of the embodiments is not shaped such that its central portion is expanded unlike the housing of Patent Document 1, so that retention of blood is unlikely to occur.

Third, since a flow path in the measurement portion has a cylindrical shape, air bubbles can be removed during priming more excellently than in Patent Document 6.

The embodiments disclosed herein are illustrative and non-restrictive in any respect. The scope of the present invention is defined by the terms of the claims, rather than the embodiments described above, and is intended to include any modifications within the scope and meaning equivalent to the terms of the claims.

REFERENCE SIGNS LIST

1: blood inlet; 2: extracted blood pressure measurement site; 3, 6, 12: pressure transducer; 4: blood pump; 5: pressure measurement site; 7*a*: dialyzer blood inlet; 7*b*: dialyzer blood outlet; 8: dialyzer; 9*a*: dialyzing fluid outlet; 9*b*: dialyzing fluid inlet; 10: dialyzing device body; 11: venous pressure measurement site; 13: blood outlet; 100, 1100: pressure measurement portion; 102: chamber; 110, 1110: housing; 110*b*: covering portion; 110*c*, 110*d*: projection; 111, 112: joint component; 111*a*: line; 111*b*: groove; 111*c*: recess; 111*h*: through hole; 111*w*: separation wall; 112*b*: covering portion; 112*d*: recess; 113, 114: engagement portion; 115: closure suppression member; 115*a*: wall surface; 116: plate-like member; 119: rib; 120, 1120: flexible membrane; 120*a*: cylindrical portion; 120*b*: tubular portion; 121: thick membrane portion; 121*a*: annular protrusion; 122: rib; 126: projection; 127: recess; 128: depression portion; 140: pressure measurement port; 141: fluid level adjustment port; 150: blood chamber; 160: air chamber; 170, 180: rotation prevention mechanism; 210, 220: blood line; 240: pressure monitor line; 241, 251: connector; 242, 252: clip; 250: fluid level adjustment line.

The invention claimed is:

1. A blood circuit, comprising:
 a pressure measurement portion connected to a pressure measurement device, the pressure measurement portion including a negative pressure measurement portion, wherein the negative pressure measurement portion includes:
a housing having a tubular shape; and
a flexible membrane having a tubular shape and provided within the housing having the tubular shape, the flexible membrane being provided close to the housing,
wherein pressure fluctuation of blood is able to be measured by permitting the blood to flow in a tube of the flexible membrane to deform the flexible membrane in a tube inward direction according to pressure of the blood to increase a space between the flexible membrane and the housing,
wherein the flexible membrane has a cylindrical shape having a circular cross section to have an inner diameter and an outer diameter each constant in an axial direction in an initial state before permitting the blood to flow,
wherein when X represents an axial length of a deformable portion of the flexible membrane in the initial state before permitting the blood to flow and Y represents an outer diameter of the deformable portion of the flexible membrane in the initial state before permitting the blood to flow, the axial length X and the outer diameter Y satisfy $4.0 \leq X/Y \leq 8.0$,
wherein when T represents a thickness of the deformable portion of the flexible membrane in the initial state before permitting the blood to flow, the thickness T satisfies $0.2 \text{ mm} \leq T \leq 0.6 \text{ mm}$,
wherein the flexible membrane has a Shore A hardness of not less than 20 and not more than 60, and
wherein when the blood is permitted to flow in the tube of the flexible membrane, three depression portions are formed at substantially equal positions along a circumferential direction of the deformable portion of the flexible membrane so as to extend in parallel with one another along the axial direction of the flexible membrane.

2. The blood circuit having the pressure measurement portion according to claim 1,
wherein the housing has a cylindrical shape to have a cross section with a circular shape to have an inner diameter and an outer diameter each constant in the axial direction.

3. A blood circuit, comprising:
a pressure measurement portion connected to a pressure measurement device, the pressure measurement portion including a positive pressure measurement portion,
wherein the positive pressure measurement portion includes:
a housing having a tubular shape; and
a flexible membrane having a tubular shape and provided in the housing having the tubular shape with a space being formed between the housing and the flexible membrane, the flexible membrane having a cross section at least a portion of which is non-circular in an initial state before permitting blood to flow, the cross section being orthogonal to an axial direction of the housing, and
wherein pressure fluctuation of blood is able to be measured by permitting the blood to flow in a tube of the flexible membrane to deform a non-circular portion of the flexible membrane in a tube outward direction according to pressure of the blood to decrease the space between the housing and the flexible membrane.

4. The blood circuit having the pressure measurement portion according to claim 3, wherein a plurality of recesses are formed in a surface of the flexible membrane and extend in parallel with one another.

5. The blood circuit having the pressure measurement portion according to claim 4, wherein in the initial state before permitting the blood to flow, in a cross section of a deformable portion of the flexible membrane, an outer circumferential edge of the flexible membrane has a length equal to or less than a length of an inner circumferential edge of the housing, the cross section being orthogonal to an axial direction of the housing.

6. The blood circuit having the pressure measurement portion according to claim 5, wherein the flexible membrane is configured to have an inner circumferential surface not contacted at any portion in the initial state before peiinitting the blood to flow.

7. The blood circuit having the pressure measurement portion according to claim 4, wherein the number of the recesses is 2 to 4.

8. The blood circuit having the pressure measurement portion according to claim 3, wherein in the initial state before permitting the blood to flow, each of cross sectional areas in the tube of the flexible membrane at both end portions of a deformable portion of the flexible membrane is larger than a cross sectional area in the tube of the flexible membrane at a central portion of the deformable portion of the flexible membrane.

9. The blood circuit having the pressure measurement portion according to claim 8, wherein in the initial state, a cross sectional area in the tube of the flexible membrane becomes gradually smaller in a direction from each of the both end portions to the central portion.

10. A blood circuit, comprising:
a pressure measurement portion connected to a pressure measurement device,
wherein the pressure measurement portion includes:
a housing having a tubular shape and having one end and the other end in an axial direction;
a flexible membrane having a tubular shape and provided in the housing having the tubular shape;
a first joint component attached to the one end of the housing; and
a second joint component attached to the other end of the housing,
wherein pressure fluctuation of blood is able to be measured by permitting the blood to flow in a tube of the flexible membrane to displace the flexible membrane according to pressure of the blood,
wherein at least a portion of the first joint component is engaged with a radially inward side of the one end of the housing to radially sandwich and fix one end portion of the flexible membrane having the tubular shape by bringing the one end portion of the flexible membrane having the tubular shape into abutment with an inner circumferential surface of the housing and an outer circumferential surface of the first joint component, and
wherein the other end portion of the flexible membrane having the tubular shape is axially sandwiched and fixed by the second joint component and the housing.

* * * * *